United States Patent
Garibay et al.

(10) Patent No.: US 8,859,493 B2
(45) Date of Patent: Oct. 14, 2014

(54) INSULIN DERIVATIVES

(75) Inventors: Patrick William Garibay, Holte (DK); Thomas Hoeg-Jensen, Klampenborg (DK); Ib Jonassen, Valby (DK); Svend Havelund, Bagsværd (DK); Peter Madsen, Bagsværd (DK); Palle Jakobsen, Værløse (DK)

(73) Assignee: Novo Nordisk A/S, Bagsvaerd (DK)

(*) Notice: Subject to any disclaimer, the term of this patent is extended or adjusted under 35 U.S.C. 154(b) by 154 days.

(21) Appl. No.: 13/506,292

(22) Filed: Apr. 9, 2012

(65) Prior Publication Data

US 2012/0208749 A1 Aug. 16, 2012

Related U.S. Application Data

(63) Continuation of application No. 12/781,134, filed on May 17, 2010, now abandoned, which is a continuation of application No. 11/814,374, filed as application No. PCT/EP2006/050594 on Feb. 1, 2006, now abandoned.

(60) Provisional application No. 60/651,271, filed on Feb. 8, 2005.

(30) Foreign Application Priority Data

Feb. 2, 2005 (DK) .................. 2005 00156

(51) Int. Cl.
*A61K 38/28* (2006.01)
*C07K 14/62* (2006.01)
*A61K 47/48* (2006.01)
*A61K 38/00* (2006.01)

(52) U.S. Cl.
CPC ........... *A61K 47/48215* (2013.01); *A61K 38/00* (2013.01); *C07K 14/62* (2013.01)
USPC ................ 514/5.9; 514/6.2; 514/6.3; 514/6.9

(58) Field of Classification Search
None
See application file for complete search history.

(56) References Cited

U.S. PATENT DOCUMENTS

| | | |
|---|---|---|
| 3,528,960 A | 9/1970 | Haas |
| 5,179,189 A | 1/1993 | Domb et al. |
| 5,359,030 A | 10/1994 | Ekwuribe |
| 5,922,675 A | 7/1999 | Baker et al. |
| 6,251,856 B1 | 6/2001 | Markussen et al. |
| 6,335,316 B1 | 1/2002 | Hughes et al. |
| 2003/0027748 A1 | 2/2003 | Ekwuribe et al. |
| 2003/0199672 A1 | 10/2003 | Knudsen et al. |
| 2004/0038867 A1 | 2/2004 | Still et al. |
| 2004/0198949 A1 | 10/2004 | Ekwuribe et al. |
| 2004/0254119 A1 | 12/2004 | West et al. |
| 2009/0239785 A1 | 9/2009 | Hubalek et al. |

FOREIGN PATENT DOCUMENTS

| | | |
|---|---|---|
| EP | 0894095 | 5/2003 |
| GB | 1492997 | 11/1977 |
| JP | 1254699 | 5/1979 |
| JP | 57-067548 A | 4/1982 |
| JP | H09502867 A | 3/1997 |
| JP | 2002-528562 A | 9/2002 |
| JP | 2003-113113 A | 4/2003 |
| WO | 95/07931 A1 | 3/1995 |
| WO | 96/29344 | 9/1996 |
| WO | 97/31022 A1 | 8/1997 |
| WO | 98/02460 A1 | 1/1998 |
| WO | 00/78302 A1 | 12/2000 |
| WO | 02/20033 A1 | 3/2002 |
| WO | 02/094200 | 11/2002 |
| WO | 02098232 | 12/2002 |
| WO | 03/013573 | 2/2003 |
| WO | 03/022208 A2 | 3/2003 |
| WO | 2005/005477 A2 | 1/2005 |
| WO | 2005/012346 A1 | 2/2005 |
| WO | 2005/012347 A2 | 2/2005 |
| WO | 2007/074133 A2 | 7/2007 |
| WO | 2007/096431 A1 | 8/2007 |
| WO | 2007/104737 A1 | 9/2007 |
| WO | 2007/128815 A1 | 11/2007 |
| WO | 2007/128817 A2 | 11/2007 |

OTHER PUBLICATIONS

Hinds, K. et al., "Synthesis and Characterization of Poly(ethylene glycol)-Insulin Conjugates", Bioconjugate Chemistry, vol. 11, pp. 195-201, 2000.
Kochendoerfer, G. et al., "Design and Chemical Synthesis of a Homogeneous Polymer-Modified Erythropoiesis Protein", Science, vol. 299, pp. 884-887, 2003.
Uchio, T. et al, "Site-specific Insulin Conjugates with Enhanced Stability and Extended Action Profile", Advanced Drug Delivery Reviews, vol. 35, pp. 289-306, 1999.

*Primary Examiner* — Gyan Chandra
(74) *Attorney, Agent, or Firm* — Jianjie Hu

(57) ABSTRACT

The present invention is related to insulin derivatives having a side chain attached either to the α-amino group of the N-terminal amino acid residue of B chain or to an ε-amino group of a Lys residue present in the B chain of the parent insulin molecule via an amide bond which side chain comprises one or more residues of ethyleneglycol, propyleneglycol and/or butyleneglycol containing independently at each termini a group selected from —$NH_2$ and —COOH; a fatty diacid moiety with 4 to 22 carbon atoms, at least one free carboxylic acid group or a group which is negatively charged at neutral pH; and possible linkers which link the individual components in the side chain together via amide or ether bonds, said linkers optionally comprising a free carboxylic acid group.

15 Claims, No Drawings

INSULIN DERIVATIVES

CROSS REFERENCE TO RELATED APPLICATIONS

This application is a continuation of U.S. application Ser. No. 12/781,134, filed May 17, 2010 now abandoned, which is a continuation of U.S. application Ser. No. 11/814,374, filed Jan. 29, 2008 now abandoned, which is a 35 U.S.C. §371 national stage application of International Patent Application PCT/EP2006/050594 (published as WO 2006/082205), filed Feb. 1, 2006, which claimed priority of Danish Patent Application PA 2005 00156, filed Feb. 2, 2005; this application further claims priority under 35 U.S.C. §119 of U.S. Provisional Application 60/651,271, filed Feb. 8, 2005.

FIELD OF THE INVENTION

The present invention relates to novel human insulin derivatives which are soluble at physiological pH values and have a prolonged profile of action. The invention also relates to methods of providing such derivatives, to pharmaceutical compositions containing them, to a method of treating diabetes and hyperglycaemia using the insulin derivatives of the invention and to the use of such insulin derivatives in the treatment of diabetes and hyperglycaemia.

BACKGROUND OF THE INVENTION

Currently, the treatment of diabetes, both type 1 diabetes and type 2 diabetes, relies to an increasing extent on the so-called intensive insulin treatment. According to this regimen, the patients are treated with multiple daily insulin injections comprising one or two daily injections of long acting insulin to cover the basal insulin requirement supplemented by bolus injections of a rapid acting insulin to cover the insulin requirement related to meals.

Long acting insulin compositions are well known in the art. Thus, one main type of long acting insulin compositions comprises injectable aqueous suspensions of insulin crystals or amorphous insulin. In these compositions, the insulin compounds utilized typically are protamine insulin, zinc insulin or protamine zinc insulin.

Certain drawbacks are associated with the use of insulin suspensions. Thus, in order to secure an accurate dosing, the insulin particles must be suspended homogeneously by gentle shaking before a defined volume of the suspension is withdrawn from a vial or expelled from a cartridge. Also, for the storage of insulin suspensions, the temperature must be kept within more narrow limits than for insulin solutions in order to avoid lump formation or coagulation.

Another type of long acting insulin compositions are solutions having a pH value below physiological pH from which the insulin will precipitate because of the rise in the pH value when the solution is injected. A drawback with these solutions is that the particle size distribution of the precipitate formed in the tissue on injection, and thus the release profile of the medication, depends on the blood flow at the injection site and other parameters in a somewhat unpredictable manner. A further drawback is that the solid particles of the insulin may act as a local irritant causing inflammation of the tissue at the site of injection.

Human insulin has three primary amino groups: the N-terminal group of the A-chain and of the B-chain and the ε-amino group of LysB29. Several insulin derivatives which are substituted in one or more of these groups are known in the prior art. Thus, U.S. Pat. No. 3,528,960 (Eli Lilly) relates to N-carboxyaroyl insulins in which one, two or three primary amino groups of the insulin molecule has a carboxyaroyl group.

According to GB Patent No. 1.492.997 (Nat. Res. Dev. Corp.), it has been found that insulin with a carbamyl substitution at $N^{\epsilon B29}$ has an improved profile of hypoglycemic effect.

JP laid-open patent application No. 1-254699 (Kodama Co., Ltd.) discloses insulin wherein a fatty acid is bound to the amino group of PheB1 or to the ε-amino group of LysB29 or to both of these. The stated purpose of the derivatisation is to obtain a pharmacologically acceptable, stable insulin preparation.

Insulins, which in the B30 position have an amino acid having at least five carbon atoms which cannot necessarily be coded for by a triplet of nucleotides, are described in JP laid-open patent application No. 57-067548 (Shionogi). The insulin analogues are claimed to be useful in the treatment of diabetes mellitus, particularly in patients who are insulin resistant due to generation of bovine or porcine insulin antibodies.

WO 95/07931 (Novo Nordisk A/S) discloses human insulin derivatives wherein the ε-amino group of LysB29 has a lipophilic substituent. These insulin derivatives have a prolonged profile of action and are soluble at physiological pH values.

EP 894095 discloses insulin derivatives wherein the N-terminal group of the B-chain and/or the ε-amino group of Lys in position B28, B29 or B30 has a substituent of the formula —CO—W—COOH where W can be a long chain hydrocarbon group. These insulin derivatives have a prolonged profile of action and are soluble at physiological pH values.

Unfortunately, many diabetics are unwilling to undertake intensive therapy due to the discomfort associated with the many injections required to maintain close control of glucose levels. This type of therapy can be both psychologically and physically painful. Upon oral administration, insulin is rapidly degraded in the gastro intestinal tract and is not absorbed into the blood stream. Therefore, many investigators have studied alternate routes for administering insulin, such as oral, rectal, transdermal, and nasal routes. Thus far, however, these routes of administration have not resulted in effective insulin absorption.

Efficient pulmonary delivery of a protein is dependent on the ability to deliver the protein to the deep lung alveolar epithelium. Proteins that are deposited in the upper airway epithelium are not absorbed to a significant extent. This is due to the overlying mucus which is approximately 30-40 μm thick and acts as a barrier to absorption. In addition, proteins deposited on this epithelium are cleared by mucociliary transport up the airways and then eliminated via the gastrointestinal tract. This mechanism also contributes substantially to the low absorption of some protein particles. The extent to which proteins are not absorbed and instead eliminated by these routes depends on their solubility, their size, as well as other less understood characteristics.

It is however well recognised that the properties of peptides can be enhanced by grafting organic chain-like molecules onto them. Such grafting can improve pharmaceutical properties such as half life in serum, stability against proteolytical degradation, and reduced immunogenicity.

The organic chain-like molecules often used to enhance properties are polyethylene glycol-based or polyethylene based chains, i.e., chains that are based on the repeating unit —$CH_2CH_2O$—. Hereinafter, the abbreviation "PEG" is used for polyethyleneglycol.

Classical PEG technology takes advantage of providing polypeptides with increased size (Stoke radius) by attaching a soluble organic molecule to the polypeptide (Kochendoerfer, G., et al., Science (299) 884-, 2003). This technology leads to reduced clearance in man and animals of a hormone polypeptide compared to the native polypeptide. However this technique is often hampered by reduced potency of the hormone polypeptides subjected to this technique (Hinds, K., et al., Bioconjugate Chem. (11), 195-, 2000). WO 02/20033 discloses a general method for the synthesis of well defined polymer modified peptides.

However, there is still a need for insulins having a more prolonged profile of action than the insulin derivatives known up till now and which at the same time are soluble at physiological pH values and have a potency which is comparable to that of human insulin. Furthermore, there is need for further insulin formulations which are well suited for pulmonary application.

SUMMARY OF THE INVENTION

The present invention is based on the recognition that acylation of insulin with one or more residues of ethyleneglycol, propyleneglycol and/or butyleneglycol in combination with fatty diacid residues has surprisingly shown a good bioavailability.

Organic chain-like molecules, which can be used to enhance properties, are polyethyleneglycol based, polypropyleneglycol based or polybutyleneglycol based chains, i.e., chains that are based on the repeating unit $CH_2CH_2O$—, $CH_2CH_2CH_2O$— or $CH_2CH_2CH_2CH_2O$—. Hereinafter, the abbreviation "PEG" is used for polyethyleneglycol, "PPG" is used for polypropyleneglycol and "PBG" is used for polybutyleneglycol.

In one aspect the present invention is related to insulin derivatives having a side chain attached either to the α-amino group of the N-terminal amino acid residue of the B chain or to an ε-amino group of a Lys residue present in the B chain of the parent insulin molecule via an amide bond which side chain comprises one or more residues of ethyleneglycol, propyleneglycol and/or butyleneglycol containing independently at each termini a group selected from —$NH_2$ and —COOH; a fatty diacid moiety with 4 to 22 carbon atoms; at least one free carboxylic acid group or a group which is negatively charged at neutral pH; and possible linkers which link the individual components in the side chain together via amide, ether or amine bonds, said linkers optionally comprising a free carboxylic acid group.

In one aspect the insulin derivatives contain a difunctional PEG, PPG or PBG group that has from 2 to 20; from 2 to 10 or from 2 to 5 residues of ethyleneglycol, propyleneglycol or butyleneglycol, respectively.

In one aspect the side chain of the insulin derivative comprise one single residue of ethyleneglycol.

In one aspect the side chain of the insulin derivative comprise one single residue of propyleneglycol.

In one aspect the side chain of the insulin derivative comprise one single residue of butyleneglycol.

In one aspect the side chain of the insulin derivative has single residues of ethyleneglycol, propyleneglycol or butyleneglycol alone or in combination.

In one aspect the side chain of the insulin derivative has one residue of propyleneglycol and one residue of butyleneglycol.

In one aspect the fatty diacid comprises from 4 to 22 carbon atoms in the carbon chain.

In one aspect the fatty diacid comprises from 6 to 22, from 8 to 20, from 8 to 18, from 4 to 18, from 6 to 18, from 8 to 16, from 8 to 22, from 8 to 17 or from 8 to 15 carbon atoms in the carbon chain.

In one aspect the linker is an amino acid residue, a peptide chain of 2-4 amino acid residues or has the motif is α-Asp; β-Asp; α-Glu; γ-Glu; α-hGlu; δ-hGlu; —N($CH_2$COOH)$CH_2$CO—; —N($CH_2CH_2$COOH)$CH_2CH_2$CO—; —N($CH_2$COOH)$CH_2CH_2$CO— or —N($CH_2CH_2$COOH)$CH_2$CO—.

In one aspect the Lys residue in the B chain will be position B3, B29 or in one of positions B23-B30.

In another aspect the invention is related to an insulin derivative having the formula

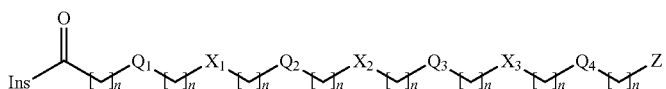

wherein Ins is the parent insulin moiety which via the α-amino group of the N-terminal amino acid residue of the B chain or an ε-amino group of a Lys residue present in the B chain of the insulin moiety is bound to the CO— group in the side chain via an amide bond; each n is independently 0, 1, 2, 3, 4, 5 or 6;

$Q_1$, $Q_2$, $Q_3$, and $Q_4$ independently of each other can be
 $(CH_2CH_2O)_s$—; $(CH_2CH_2CH_2O)_s$—;
 $(CH_2CH_2CH_2CH_2O)_s$—;
 $(CH_2CH_2OCH_2CH_2CH_2CH_2O)_s$— or
 $(CH_2CH_2CH_2OCH_2CH_2CH_2CH_2CH_2O)_s$— where s is 1-20
—$(CH_2)_r$— where r is an integer from 4 to 22; or a divalent hydrocarbon chain comprising 1, 2 or 3-CH=CH— groups and a number of —$CH_2$— groups sufficient to give a total number of carbon atoms in the chain in the range of 4 to 22;
—$(CH_2)_t$— or —$(CH_2OCH_2)_t$—, where t is an integer from 1 to 6;
—$(CR_1R_2)_q$—, where $R_1$ and $R_2$ independently of each other can be H, —COOH, $(CH_2)_{1-6}$COOH and $R_1$ and $R_2$ can be different at each carbon, and q is 1-6,
—$((CR_3R_4)_{q1})_1$—(NHCO—$(CR_3R_4)_{q1}$—NHCO$)_{1-2}$— $((CR_3R_4)_{q1})_1$ or —$((CR_3R_4)_{q1})_1$—(CONH— $(CR_3R_4)_{q1}$—CONH$)_{1-2}$—$((CR_3R_4)_{q1})_1$—,
—$((CR_3R_4)_{q1})_1$—(NHCO—$(CR_3R_4)_{q1}$—CONH$)_{1-2}$— $((CR_3R_4)_{q1})_1$ or —$((CR_3R_4)_{q1})_1$—(CONH— $(CR_3R_4)_{q1}$—NHCO$)_{1-2}$—$((CR_3R_4)_{q1})_1$ where $R_3$ and $R_4$ independently of each other can be H, —COOH, and $R_3$ and $R_4$ can be different at each carbon, and $q_1$ is 1-6-, or
a bond;
with the proviso that $Q_1$-$Q_4$ are different;
$X_1$, $X_2$ and $X_3$ are independently
O;
a bond; or

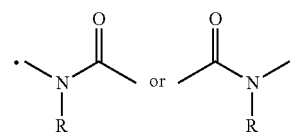

where R is hydrogen or —$(CH_2)_p$—COOH, —$(CH_2)_p$—$SO_3H$, —$(CH_2)_p$—$PO_3H_2$, —$(CH_2)_p$—O—$SO_3H$; —$(CH_2)_p$—O—$PO_3H_2$; or —$(CH_2)_p$-tetrazol-5-yl, where each p independently of the other p's is an integer in the range of 1 to 6; and Z is:
—COOH;
—CO— Asp;
—CO— Glu;
—CO— Gly;
—CO— Sar;
—CH(COOH)$_2$,
—N(CH$_2$COOH)$_2$;
—SO$_3$H
—OSO$_3$H
—OPO3H$_2$
—PO$_3$H$_2$ or
-tetrazol-5-yl
and any Zn$^{2+}$ complex thereof.

Where mentioned that $R_1$, $R_2$, $R_3$ and $R_4$ can be different at each carbon is meant that $R_1$, $R_2$, $R_3$ and $R_4$ can be different for each value of q or $q_1$.

In one aspect r is from 6 to 22, from 8 to 20, from 8 to 18, from 4 to 18, from 6 to 18 from 8 to 16 from 8 to 22 from 8 to 17 from 8 to 15.

In another aspect s is in the range of 2-12, 2-4 or 2-3.

In another aspect s is 1.

In one aspect n is from 1-6, from 2-6, from 2-5, from 2-4, from 0-2 or from 2-3.

In one aspect q is from 1-5, from 1-4, from 1-3 or from 1-2.

In one aspect $q_1$ is from 1-5, from 1-4, from 1-3 or from 1-2.

In one aspect t is from 1-6, from 1-5, from 1-4, from 1-3 or from 1-2.

In one aspect Z is —COOH.
In one aspect Z is —CO— Asp.
In another aspect Z is —CO— Glu.
In another aspect Z is —CO— Gly.
In another aspect Z is —CO— Sar.
In another aspect Z is —CH(COOH)$_2$.
In another aspect Z is —N(CH$_2$COOH)$_2$.
In another aspect Z is —SO$_3$H.
In another aspect Z is —PO$_3$H.
In another aspect Z is O—SO$_3$H;
In another aspect Z is O—PO$_3$H$_2$;
In another aspect Z is tetrazol-5-yl.

In a further aspect the parent insulin is a desB30 human insulin analogue.

Non limiting examples of parent insulins are human insulin; desB1 human insulin; desB30 human insulin; GlyA21 human insulin; GlyA21 desB30 human insulin; AspB28 human insulin; porcine insulin; LysB28 ProB29 human insulin; GlyA21 ArgB31 ArgB32 human insulin; LysB3 GluB29 human insulin or AspB28 desB30 human insulin.

In a still further aspect the insulin derivative are selected from the group consisting of N$^{\epsilon B29}$-(3-[2-{2-[ω-carboxy-pentadecanoyl-γ-glutamyl-(2-amino-ethoxy)]-ethoxy}-ethoxy]-propionyl) desB30 human insulin, N$^{\epsilon B29}$-(3-[2-{2-[2-[ω-carboxy-heptadecanoyl-γ-glutamyl-(2-amino-ethoxy)]-ethoxy-ethoxy}-ethoxy]-propionyl) desB30 human insulin, N$^{\epsilon B29}$-{3-[2-(2-{2-[2-(ω-carboxy-pentadecanoylamino)-ethoxy]-ethoxy}-ethoxy)-ethoxy]-propionyl-γ-glutamyl desB30 human insulin, N$^{\epsilon B29}$-(ω-[2-(2-{2-[2-(2-carboxy-ethoxy]-ethoxy}ethoxy)-ethoxy)-ethylcarbamoyl]-heptadecanoyl-α-glutamyl) desB30 human insulin, N$^{\epsilon B29}$-(ω-[2-(2-{2-[2-(2-carboxy-ethoxy)-ethoxy]-ethoxy}-ethoxy)-ethylcarbamoyl]-heptadecanoyl-γ-glutamyl) desB30 human insulin, N$^{\epsilon B29}$-3-[2-(2-{2-[2-(ω-carboxy-heptadecanoylamino)-ethoxy]-ethoxy}-ethoxy)-ethoxy]-propionyl-γ-glutamyl desB30 human insulin, N$^{\epsilon B29}$-(3-(3-{2-[2-(3-[7-carboxyheptanoylamino]propoxy)ethoxy]ethoxy}propylcarbamoyl)propionyl) desB30 human insulin, N$^{\epsilon B29}$-(3-(3-{4-[3-(7-Carboxyheptanoylamino)propoxy]butoxy}propylcarbamoyl)-propionyl-γ-glutamyl) desB30 human insulin, N$^{\epsilon B29}$-(3-(3-{2-[2-(3-[9-Carboxynonanoylamino]propoxy)ethoxy]ethoxy}-propylcarbamoyl)propionyl) desB30 human insulin, N$^{\epsilon B29}$-(3-(2-{2-[2-(9-carboxynonanoylamino)ethoxy]ethoxy}ethylcarbamoyl)propionyl-γ-glutamyl) desB30 human insulin, N$^{\epsilon B29}$-(3-(3-{4-[3-(9-Carboxynonanoylamino)propoxy]butoxy}-propylcarbamoyl)propionyl-γ-glutamyl) desB30 human insulin, N$^{\epsilon B29}$-(2-[3-(2-(2-{2-(7-carboxyheptanoylamino)ethoxy}ethoxy)-ethylcarbamoyl]propionyl-γ-glutamyl) desB30 human insulin, N$^{\epsilon B29}$-(3-[2-(2-{2-[2-(ω-carboxy-pentadecanoylamino)ethoxy]ethoxy}ethoxy)ethoxy]propionyl)) desB30 human insulin, N$^{\epsilon B29}$-(3-(2-{2-[2-(2-{2-[2-(2-{2-[2-(ω-carboxy-tridecanoylamino)-ethoxy]-ethoxy}-ethoxy)-ethoxy]-ethoxy}-ethoxy)-ethoxy]-ethoxy}-ethoxy)-propionoyl-γ-glutamyl) desB30 human insulin, N$^{\epsilon B29}$-(3-[2-(2-{2-[2-(ω-Carboxy-tridecanoylamino)-ethoxy]-ethoxy}-ethoxy)-ethoxy]-propionoyl-γ-glutamyl) desB30 human insulin, N$^{\epsilon B29}$-(3-[2-(2-{2-[2-(2-{2-[2-(ω-carboxy-tridecanoylamino)-ethoxy]-ethoxy}-ethoxy)-ethoxy]-ethoxy}-ethoxy)-ethoxy]-ethoxy}-propionoyl-γ-glutamyl) desB30 human insulin, N$^{\epsilon B29}$-(3-(2-{2-[2-(ω-Carboxy-pentadecanoylamino)-ethoxy]-ethoxy}-ethylcarbamoyl)-propionyl-γ-glutamyl) desB30 human insulin, N$^{\epsilon B29}$-(3-(3-{2-[2-(3-[ω-Carboxypentadecanoylamino]propoxy)ethoxy]-ethoxy}propylcarbamoyl)propionyl-γ-glutamyl) desB30 human insulin, N$^{\epsilon B29}$-(3-(3-{4-[3-(ω-Carboxyundecanoylamino)propoxy]butoxypropylcarbamoyl)propionyl-γ-glutamyl) desB30 human insulin, N$^{\epsilon B29}$-(3-(3-{4-[3-(ω-carboxytridecanoylamino)propoxy]butoxypropyl-carbamoyl) propionyl-γ-glutamyl) desB30 human insulin, N$^{\epsilon B29}$-(3-(2-{2-[2-(ω-Carboxyundecanoylamino)ethoxy]ethoxy}ethylcarbamoyl)propionyl-γ-glutamyl) desB30 human insulin, N$^{\epsilon B29}$-(3-(2-{2-[2-(ω-carboxytridecanoylamino)ethoxy]ethoxy}ethylcarbamoyl)-propionyl-γ-glutamyl) desB30 human insulin, N$^{\epsilon B29}$-{3-[2-(2-{2-[2-(ω-carboxy-pentadecanoylamino)ethoxy]ethoxy}ethoxy)ethoxy]propionyl-gamma-γ-D-glutamyl) desB30 human insulin, N$^{\epsilon B29}$-{3-[2-(2-{2-[2-(7-carboxyheptanoylamino)ethoxy]ethoxy}ethoxy)ethoxy]-propionyl-γ-glutamyl} desB30 human insulin, N$^{\epsilon B29}$-{3-[2-(2-{2-[2-(9-carboxynonanoylamino)ethoxy]ethoxy}ethoxy)ethoxy]propionyl-γ-glutamyl} desB30 human insulin, N$^{\epsilon B29}$-{3-[2-(2-{2-[2-(ω-carboxyundecanoylamino)ethoxy]ethoxy}ethoxy)ethoxy]-propionyl-γ-glutamyl} desB30 human insulin, N$^{\epsilon B29}$-{3-[2-(2-{2-[2-(ω-carboxytridecanoylamino)ethoxy]ethoxy}ethoxy)ethoxy]propionyl-γ-glutamyl} desB30 human insulin.

Insulin derivatives according to the invention may be provided in the form of essentially zinc free compounds or in the form of zinc complexes. When zinc complexes of an insulin derivative according to the invention are provided, two Zn$^{2+}$ ions, three Zn$^{2+}$ ions or four Zn$^{2+}$ ions can be bound to each insulin hexamer. Solutions of zinc complexes of the insulin derivatives will contain mixtures of such species.

In a further aspect the invention is related to a pharmaceutical composition comprising a therapeutically effective amount of an insulin derivative according to the invention together with a pharmaceutically acceptable carrier can be provided for the treatment of type 1 diabetes, type 2 diabetes and other states that cause hyperglycaemia in patients in need of such a treatment. An insulin derivative according to the invention can be used for the manufacture of a pharmaceutical composition for use in the treatment of type 1 diabetes, type 2 diabetes and other states that cause hyperglycaemia.

In a further aspect of the invention, there is provided a pharmaceutical composition for treating type 1 diabetes, type 2 diabetes and other states that cause hyperglycaemia in a patient in need of such a treatment, comprising a therapeutically effective amount of an insulin derivative according to the invention in mixture with an insulin or an insulin analogue which has a rapid onset of action, together with pharmaceutically acceptable carriers and additives.

In a further aspect the invention is related to a pulmonary application for treating type 1 diabetes, type 2 diabetes and other states that cause hyperglycaemia in a patient in need of such a treatment, comprising a therapeutically effective amount of an insulin derivative according to the invention optionally in mixture with an insulin or an insulin analogue which has a rapid onset of action, together with pharmaceutically acceptable carriers and additives.

In one aspect the invention provides a pharmaceutical composition being a mixture of an insulin derivative according to the invention and a rapid acting insulin analogue selected group consisting of AspB28 human insulin; LysB28 ProB29 human insulin and LysB3 GluB29 human insulin.

The insulin derivative according to the invention and the rapid acting insulin analogue can be mixed in a ratio from about 90/10%; about 70/30% or about 50/50%.

In a further aspect of the invention, there is provided a method of treating type 1 diabetes, type 2 diabetes and other states that cause hyperglycaemia in a patient in need of such a treatment, comprising administering to the patient a therapeutically effective amount of an insulin derivative according to the invention together with a pharmaceutically acceptable carrier and pharmaceutical acceptable additives.

In a further aspect of the invention, there is provided a method of treating type 1 diabetes, type 2 diabetes and other states that cause hyperglycaemia in a patient in need of such a treatment, comprising administering to the patient a therapeutically effective amount of an insulin derivative according to the invention in mixture with an insulin or an insulin analogue which has a rapid onset of action, together with a pharmaceutically acceptable carrier and pharmaceutical acceptable additives.

In another aspect of the invention the insulin derivatives has a side chain attached either to the α-amino group of the N-terminal amino acid residue of B chain or to an ε-amino group of a Lys residue present in the B chain of the parent insulin molecule via an amide bond which side chain comprises a monodisperse, diffunctionel PEG group containing independently at each termini a group selected from —OH; —NH$_2$ and —COOH; a fatty diacid moiety with 4 to 22 carbon atoms, at least one free carboxylic acid group or a group which is negatively charged at neutral pH; and possible linkers which link the individual components in the side chain together via amide, ether or amine bonds, said linkers optionally comprising a free carboxylic acid group.

In another aspect of the invention the PEG group of the insulin derivative has from 1 to 20; from 1 to 10 or from 1 to 5 ethylene residues.

In another aspect of the invention the insulin derivatives has a side chain attached either to the α-amino group of the N-terminal amino acid residue of B chain or to an ε-amino group of a Lys residue present in the B chain of the parent insulin molecule via an amide bond which side chain comprises a monodisperse, diffunctionel PEG group containing independently at each termini a group selected from —OH; —NH$_2$ and —COOH; a fatty diacid moiety with 4 to 22 carbon atoms, at least one free carboxylic acid group or a group which is negatively charged at neutral pH; and possible linkers which link the individual components in the side chain together via amide, ether or amine bonds, said linkers optionally comprising a free carboxylic acid group.

In a further aspect of the invention the insulin derivatives comprises a difunctional PEG group which has from 1 to 20; from 1 to 10 or from 1 to 5 ethylene units.

In a further aspect of the invention the insulin derivatives comprises a fatty diacid which comprises from 4 to 22 carbon atoms in the carbon chain.

In a further aspect of the invention the insulin derivatives comprises a fatty acid, wherein the fatty diacid comprises from 6 to 22, from 8 to 20, from 8 to 18, from 4 to 18, from 6 to 18, from 8 to 16, from 8 to 22, from 8 to 17 or from 8 to 15 carbon atoms in the carbon chain.

In a further aspect of the invention the insulin derivatives comprises a linker wherein the linker is an amino acid residue, a peptide chain of 2-4 amino acid residues or has the motif α-Asp, β-Asp, α-Glu, γ-Glu, α-hGlu, δ-hGlu, —N(CH$_2$COOH)CH$_2$CO—, —N(CH$_2$CH$_2$COOH)CH$_2$CH$_2$CO—, —N(CH$_2$COOH)CH$_2$CH$_2$CO— or —N(CH$_2$CH$_2$COOH)CH$_2$CO—

In a further aspect of the invention the insulin derivatives comprises a Lys residue wherein the Lys residue in the B chain of the parent insulin in either position B3 or in one of positions B23-30.

In a further aspect of the invention the insulin derivatives has the formula

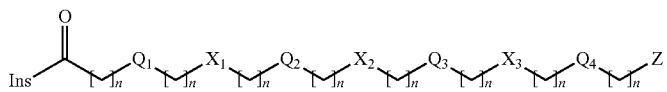

wherein Ins is the parent insulin moiety which via the α-amino group of the N-terminal amino acid residue of the B chain or an ε-amino group of a Lys residue present in the B chain of the insulin moiety is bound to the CO— group in the side chain via an amide bond;

each n is independently 0, 1, 2, 3, 4, 5 or 6;

Q$_1$, Q$_2$, Q$_3$, and Q$_4$ independently of each other can be
—(CH$_2$CH$_2$O)$_s$— where s is 1-20,
—(CH$_2$)$_r$— where r is an integer from 4 to 22; or a divalent hydrocarbon chain comprising 1, 2 or 3 -CH=CH— groups and a number of —CH$_2$ groups sufficient to give a total number of carbon atoms in the chain in the range of 4 to 22;
—(CH$_2$)$_t$— or —(CH$_2$OCH$_2$)$_t$—, where t is an integer from 1 to 6;
—(CR$_1$R$_2$)$_q$—, where R$_1$ and R$_2$ independently of each other can be H, —COOH, and R$_1$ and R$_2$ can be different at each carbon, and q is 1-6,
—((CR$_3$R$_4$)$_{q1}$)$_1$—(NHCO—(CR$_3$R$_4$)$_{q1}$)$_1$—NHCO)$_{1-2}$—((CR$_3$R$_4$)$_{q1}$)$_1$ or —((CR$_3$R$_4$)$_{q1}$)$_1$—(CONH—(CR$_3$R$_4$)$_{q1}$—CONH)$_{1-2}$—((CR$_3$R$_4$)$_{q1}$—)—, where R$_3$ and $R_4$ independently of each other can be H, —COOH, and $R_3$ and $R_4$ can be different at each carbon, and $q_1$ is 1-6-, or a bond;

with the proviso that $Q_1$-$Q_4$ are different;

X and V and G are independently

O;

a bond; or

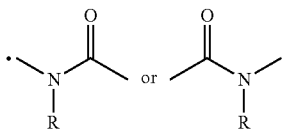

where R is hydrogen or —$(CH_2)_p$—COOH, —$(CH_2)_p$—$SO_3H$, —$(CH_2)_p$—$PO_3H_2$, —$(CH_2)_p$—O—$SO_3H$; —$(CH_2)_p$—O—$PO_3H_2$; or —$(CH_2)_p$-tetrazolyl, where each p independently of the other p's is an integer in the range of 1 to 6; and Z is:
—COOH;
—CO-Asp;
—CO-Glu;
—CO-Gly;
—CO-Sar;
—CH(COOH)$_2$;
—N(CH$_2$COOH)$_2$;
—SO$_3$H
—OSO$_3$H
—OPO3H$_2$
—PO$_3$H$_2$ or
-tetrazolyl.

In a further aspect of the invention the insulin derivatives according to the formula, s is from 6 to 22, from 8 to 20, from 8 to 18, from 4 to 18, from 6 to 18, from 8 to 16, from 8 to 22, from 8 to 17 or from 8 to 15.

In a further aspect of the invention the insulin derivatives according to the formula s is from 1-20, from 1-10 or from 1-5.

In a further aspect of the invention the insulin derivative according to the formula, Z is —COOH.

In a further aspect of the invention the insulin derivative according to the invention, the parent insulin is a desB30 human insulin analogue.

In a further aspect of the invention the insulin derivative according to the invention, the parent insulin is selected from the group consisting of human insulin; desB1 human insulin; desB30 human insulin; GlyA21 human insulin; GlyA21 desB30 human insulin; AspB28 human insulin; porcine insulin; LysB28ProB29 human insulin; GlyA21ArgB31ArgB32 human insulin; and LysB3GluB29 human insulin.

In a further aspect of the invention the insulin derivative according the invention is selected from the group consisting of $N^{\epsilon B29}$—($N^{\alpha}$—(HOOC(CH$_2$)$_{14}$CO)-γ-L-Glu-HN (CH$_2$CH$_2$O)$_4$—CH$_2$CH$_2$CO) desB30 human insulin; $N^{\epsilon B29}$—($N^{\alpha}$—(HOOC(CH$_2$)$_{16}$CO)-γ-L-Glu-HN (CH$_2$CH$_2$O)$_4$—CH$_2$CH$_2$CO) des(B30) human insulin; $N^{\epsilon B29}$—($N^{\alpha}$—(HOOC(CH$_2$CH$_2$O)$_4$—CH$_2$CH$_2$NH—OC (CH$_2$)$_{16}$CO)-α-L-Glu-) des(B30) human insulin; $N^{\epsilon B29}$-{3-[2-(2-{2-[2-(15-Carboxy-pentadecanoylamino)-ethoxy]-ethoxy}-ethoxy)-ethoxy]-propionyl-gamma-Glu desB30 insulin; and $N^{\epsilon B29}$-3-[2-(2-{2-[2-(17-Carboxy-heptadecanoylamino)-ethoxy]-ethoxy}-ethoxy)-ethoxy]-propionyl γ-Glu desB30 insulin In a further aspect of the invention there is provided a pharmaceutical composition for the treatment of diabetes in a patient in need of such treatment, comprising a therapeutically effective amount of an insulin derivative according to the invention together with a pharmaceutically acceptable carrier.

In a further aspect of the invention there is provided a pharmaceutical composition for the treatment of diabetes in a patient in need of such treatment, comprising a therapeutically effective amount of an insulin derivative according to the invention in mixture with an insulin or an insulin analogue which has a rapid onset of action, together with a pharmaceutically acceptable carrier.

In a further aspect of the invention there is provided a pharmaceutical composition according to the invention intended for pulmonal administration.

In a further aspect of the invention there is provided a method of treating diabetes in a patient in need of such a treatment, comprising administering to the patient a therapeutically effective amount of an insulin derivative according to claim 1 together with a pharmaceutically acceptable carrier.

In a further aspect of the invention there is provided a method of treating diabetes in a patient in need of such a treatment, comprising administering to the patient a therapeutically effective amount of an insulin derivative according to claim 1 in mixture with an insulin or an insulin analogue which has a rapid onset of action, together with a pharmaceutically acceptable carrier.

DETAILED DESCRIPTION OF THE INVENTION

The present insulin derivatives are characterized by having a side chain attached to a Lys group in the B chain or to the N-terminal amino group in the B-chain of the parent insulin molecule which side chain comprises one or more residues of ethyleneglycol, propyleneglycol and/or butyleneglycol and a fatty diacid moiety.

The insulin derivative according to the invention is furthermore characterized in having at least one free carboxylic acid group in the side chain and may comprise up to 2, 3 or 4 free carboxylic acid groups or a group which is negatively charged at neutral pH.

The insulin derivatives will only contain one lysine residue. This lysine residue may either be in position B29 as in human insulin or in one of position B3, B30 or B23 to B28.

The residues of ethyleneglycol, propyleneglycol and/or butyleneglycol will have any combination of the three groups —OH; —NH$_2$ and —COOH at each end. The residues of ethyleneglycol, propyleneglycol and/or butyleneglycol will typically be in the form of an ethyleneglycol residue followed by a butyleneglycol residue or have a chain length of 2 to 20 PEG, PPG or PBG residues corresponding to a molecular weight of about 200 to 800.

The residues of ethyleneglycol, propyleneglycol and/or butyleneglycol will typically be in the form of an ethyleneglycol residue followed by a butylen residue —(CH$_2$CH$_2$OCH$_2$CH$_2$CH$_2$CH$_2$O)$_m$ where m is 1 to 20.

The difunctional PEG or PPG or PBG will have any combination of the three groups —OH; —NH$_2$, and —COOH at each end and will typically have a chain length of 1 to 20 PEG residues corresponding to a molecular weight of about 200 to 1000.

Non limiting examples of amino PEG moieties are H$_2$N—(CH$_2$)$_u$—(OCH$_2$CH$_2$)$_m$—O(CH$_2$)$_u$—COOH and H$_2$N—

(CH₂), —NH—CO—(CH₂)ᵤ—(OCH₂CH₂)ₘ(CH₂)ᵥ—COOH, where u are independently 1 to 6, m is 2 to 20 and v is 1 to 6.

Non limiting examples of amino PPG moieties are H₂N—(CH₂)ᵤ—(OCH₂CH₂CH₂)ₘ—O(CH₂)ᵤ—COOH and H₂N—(CH₂), —NH—CO—(CH₂)ᵤ—(OCH₂CH₂CH₂)ₘ—(CH₂)ᵤ—COOH, where u are independently 1 to 6, m is 2 to 20 and v is 1 to 6.

Non limiting examples of amino PBG moieties are H₂N—(CH₂)ᵤ—(OCH₂CH₂CH₂CH₂)ₘ—O(CH₂)ᵤ—COOH and H₂N—(CH₂), —NH—CO—(CH₂)ᵤ—(OCH₂CH₂CH₂CH₂)ₘ—(CH₂)ᵤ—COOH, where u are independently 1 to 6, m is 2 to 20 and v is 1 to 6.

The fatty diacid will typically comprise from 4 to 22, from 6 to 22, from 8 to 20, from 8 to 18, from 4 to 18, from 6 to 18, from 8 to 16, from 8 to 22, from 8 to 12, from 8 to 10, from 8 to 17 or from 8 to 15 carbon atoms in the carbon chain.

Non limiting examples of the fatty diacid moiety are diacids with the formula HOOC—(CH₂)$_{r1}$—COOH, where r1 is 4 to 22. Examples of fatty diacids are succinic acid, hexanedioic acid, octanedioic acid, decanedioic acid, dodecanedioic acid, tetradecanedioic acid, hexadecanedioic acid or octadecanedioic acid.

The insulin moiety—in the present text also referred to as the parent insulin—or insulin derivative according to the invention can be a naturally occurring insulin such as human insulin or porcine insulin. Alternatively, the parent insulin can be an insulin analogue.

In one group of parent insulin analogues, the amino acid residue at position A21 is Asn.

In another group of parent insulin analogues, the amino acid residue at position B1 has been deleted. A specific example from this group of parent insulin analogues is desB1 human insulin.

In another group of parent insulin analogues, the amino acid residue at position B30 has been deleted. A specific example from this group of parent insulin analogues is desB30 human insulin.

In another group of parent insulin analogues, the amino acid residue at position B28 is Asp. A specific example from this group of parent insulin analogues is AspB28 human insulin.

In another group of parent insulin analogues, the amino acid residue at position B28 is Lys and the amino acid residue at position B29 is Pro. A specific example from this group of parent insulin analogues is LysB28 ProB29 human insulin.

In another group of parent insulin analogues the amino acid residue in position B30 is Lys and the amino acid residue in position B29 is any codable amino acid except Cys, Arg and Lys. An example is an insulin analogue where the amino acid residue at position B29 is Thr and the amino acid residue at position B30 is Lys. A specific example from this group of parent insulin analogues is ThrB29 LysB30 human insulin.

In another group of parent insulin analogues, the amino acid residue at position B3 is Lys and the amino acid residue at position B29 is Glu. A specific example from this group of parent insulin analogues is LysB3 GluB29 human insulin.

The linkers will typically be an amino acid residue or a chain of amino acid residue comprising up to four amino acids. Thus, the linker may be selected from the group consisting of α-Asp; β-Asp; α-Glu; γ-Glu; α-hGlu; δ-hGlu; —N(CH₂COOH)CH₂CO—, —N(CH₂CH₂COOH)CH₂CH₂CO—; —N(CH₂COOH)CH₂CH₂CO— or —N(CH₂CH₂COOH)CH₂CO—

In a further aspect the linker can be a chain composed of two amino acid residues of which one has from 4 to 10 carbon atoms and a carboxylic acid group in the side chain while the other has from 2 to 11 carbon atoms but no free carboxylic acid group. The amino acid residue with no free carboxylic acid group can be a neutral, codable α-amino acid residue. Examples of such linkers are: α-Asp-Gly; Gly-α-Asp; β-Asp-Gly; Gly-β-Asp; α-Glu-Gly; Gly-α-Glu; γ-Glu-Gly; Gly-γ-Glu; α-hGlu-Gly; Gly-α-hGlu; δ-hGlu-Gly; and Gly-δ-hGlu.

In a further aspect the linker is a chain composed of two amino acid residues, independently having from 4 to 10 carbon atoms, and both having a carboxylic acid group in the side chain. Examples of such linkers are: α-Asp-α-Asp; α-Asp-α-Glu; α-Asp-α-hGlu; α-Asp-β-Asp; α-Asp-γ-Glu; α-Asp-δ-hGlu; β-Asp-α-Asp; β-Asp-α-Glu; β-Asp-α-hGlu; β-Asp-β-Asp; β-Asp-γ-Glu; β-Asp-δ-hGlu; α-Glu-α-Asp; α-Glu-α-hGlu; α-Glu-β-Asp; α-Glu-γ-Glu; γ-Glu-α-Asp; γ-Glu-α-hGlu; γ-Glu-β-Asp; Glu; γ-Glu-O-hGlu; α-hGlu-α-Asp; α-hGlu-α-Glu; α-hGlu-α-hGlu; α-hGlu-β-Asp; α-hGlu-γ-Glu; α-hGlu-δ-hGlu; δ-hGlu-α-Asp; δ-hGlu-α-hGlu; δ-hGlu-β-Asp; δ-hGlu-γ-Glu; and δ-hGlu-δ-hGlu.

In a further aspect the linker is a chain composed of three amino acid residues, independently having from 4 to 10 carbon atoms, the amino acid residues of the chain being selected from the group of residues having a neutral side chain and residues having a carboxylic acid group in the side chain so that the chain has at least one residue which has a carboxylic acid group in the side chain. In one aspect, the amino acid residues are codable residues.

In a further aspect, the linker is a chain composed of four amino acid residues, independently having from 4 to 10 carbon atoms, the amino acid residues of the chain being selected from the group having a neutral side chain and residues having a carboxylic acid group in the side chain so that the chain has at least one residue which has a carboxylic acid group in the side chain. In one aspect, the amino acid residues are codable residues.

Examples of insulin derivatives according to the invention are the following compounds:

$N^{\epsilon B29}$-(3-[2-(2-{2-[2-(ω-carboxyheptadecanoylamino)ethoxy]ethoxy}ethoxy)-ethoxy]propionyl-γ-glutamyl) desB30 human insulin;

$N^{\epsilon B29}$-(3-[2-(2-{2-[2-(ω-carboxyhexadecanoylamino)ethoxy]ethoxy}ethoxy)-ethoxy]propionyl-γ-glutamyl) desB30 human insulin;

$N^{\epsilon B29}$-(3-[2-(2-{2-[2-(ω-carboxytridecanoylamino)ethoxy]ethoxy}ethoxy)-ethoxy]propionyl-γ-glutamyl) desB30 human insulin;

$N^{\epsilon B29}$-(3-[2-(2-{2-[2-(ω-carboxyundecanoylamino)ethoxy]ethoxy}ethoxy)-ethoxy]propionyl-γ-glutamyl) desB30 human insulin;

$N^{\epsilon B29}$-(3-[2-(2-{2-[2-(ω-carboxynonanoylamino)ethoxy]ethoxy}ethoxy)-ethoxy]propionyl-γ-glutamyl) desB30 human insulin;

$N^{\epsilon B29}$-(3-[2-(2-{2-[2-(ω-carboxyheptanoylamino)ethoxy]ethoxy}ethoxy)-ethoxy]propionyl-γ-glutamyl) desB30 human insulin;

$N^{\epsilon B29}$-(3-[2-(2-{2-[2-ω-carboxyheptadecanoylamino)ethoxy]ethoxy}ethoxy)-ethoxy]propionyl) desB30 human insulin;

$N^{\epsilon B29}$-(3-[2-(2-{2-[2-(ω-carboxyhexadedecanoylamino)ethoxy]ethoxy}ethoxy)-ethoxy]propionyl) desB30 human insulin;

$N^{\epsilon B29}$-(3-[2-(2-{2-[2-(ω-carboxytridecanoylamino)ethoxy]ethoxy}ethoxy)-ethoxy]propionyl) desB30 human insulin;

$N^{\epsilon B29}$-(3-[2-(2-{2-[2-(ω-carboxyundecanoylamino)ethoxy]ethoxy}ethoxy)-ethoxy]propionyl) desB30 human insulin;

N$^{\epsilon B29}$-(3-[2-(2-{2-[2-(ω-carboxynonanoylamino)ethoxy]ethoxy}ethoxy)-ethoxy]propionyl) desB30 human insulin;

N$^{\epsilon B29}$-(3-[2-(2-{2-[2-(ω-carboxyheptanoylamino)ethoxy]ethoxy}ethoxy)-ethoxy]propionyl) desB30 human insulin;

N$^{\epsilon B29}$-(3-(3-{2-[3-(ω-carboxyheptadecanoylamino)propoxy]ethoxy}-propylcarbamoyl)propionyl) desB30 human insulin;

N$^{\epsilon B29}$-(3-(3-{2-[3-(ω-carboxyhexadecanoylamino)propoxy]ethoxy}-propylcarbamoyl)propionyl) desB30 human insulin;

N$^{\epsilon B29}$-(3-(3-{2-[3-(ω-carboxypentadecanoylamino)propoxy]ethoxy}-propylcarbamoyl)propionyl) desB30 human insulin;

N$^{\epsilon B29}$-(3-(3-{2-[3-(ω-carboxytridecanoylamino)propoxy]ethoxy}-propylcarbamoyl)propionyl) desB30 human insulin;

N$^{\epsilon B29}$-(3-(3-{2-[3-(ω-carboxyundecanoylamino)propoxy]ethoxy}-propylcarbamoyl)propionyl) desB30 human insulin;

N$^{\epsilon B29}$-(3-(3-{2-[3-(ω-carboxynonanoylamino)propoxy]ethoxy}-propylcarbamoyl)propionyl) desB30 human insulin;

N$^{\epsilon B29}$-(3-(3-{2-[3-(ω-carboxyheptanoylamino)propoxy]ethoxy}-propylcarbamoyl)propionyl) desB30 human insulin;

N$^{\epsilon B29}$-(3-(3-{2-[3-(ω-carboxyheptadecanoylamino)propoxy]ethoxy}-propylcarbamoyl)propionyl-γ-glutamyl) desB30 human insulin;

N$^{\epsilon B29}$-(3-(3-{2-[3-(ω-carboxyhexadecanoylamino)propoxy]ethoxy}-propylcarbamoyl)propionyl-γ-glutamyl) desB30 human insulin;

N$^{\epsilon B29}$-(3-(3-{2-[3-(ω-carboxypentadecanoylamino)propoxy]ethoxy}-propylcarbamoyl)propionyl-γ-glutamyl) desB30 human insulin;

N$^{\epsilon B29}$-(3-(3-{2-[3-(ω-carboxytridecanoylamino)propoxy]ethoxy}-propylcarbamoyl)propionyl-γ-glutamyl) desB30 human insulin;

N$^{\epsilon B29}$-(3-(3-{2-[3-(ω-carboxyundecanoylamino)propoxy]ethoxy}-propylcarbamoyl)propionyl-γ-glutamyl) desB30 human insulin;

N$^{\epsilon B29}$-(3-(3-{2-[3-(ω-carboxynonanoylamino)propoxy]ethoxy}-propylcarbamoyl)propionyl-γ-glutamyl) desB30 human insulin;

N$^{\epsilon B29}$-(3-(3-{2-[3-(ω-carboxyheptanoylamino)propoxy]ethoxy}-propylcarbamoyl)propionyl-γ-glutamyl) desB30 human insulin;

N$^{\epsilon B29}$-(3-(2-{2-[2-(ω-carboxypentadecanoylamino)ethoxy]ethoxy}-ethylcarbamoyl)propionyl) desB30 human insulin;

N$^{\epsilon B29}$-(3-(2-{2-[2-(ω-carboxyhexadecanoylamino)ethoxy]ethoxy}-ethylcarbamoyl)propionyl) desB30 human insulin;

N$^{\epsilon B29}$-(3-(2-{2-[2-(ω-carboxypentadecanoylamino)ethoxy]ethoxy}-ethylcarbamoyl)propionyl) desB30 human insulin;

N$^{\epsilon B29}$-(3-(2-{2-[2-(ω-carboxytridecanoylamino)ethoxy]ethoxy}-ethylcarbamoyl)propionyl) desB30 human insulin;

N$^{\epsilon B29}$-(3-(2-{2-[2-(ω-carboxyundecanoylamino)ethoxy]ethoxy}-ethylcarbamoyl)propionyl) desB30 human insulin;

N$^{\epsilon B29}$-(3-(2-{2-[2-(ω-carboxynonanoylamino)ethoxy]ethoxy}-ethylcarbamoyl)propionyl) desB30 human insulin;

N$^{\epsilon B29}$-(3-(2-{2-[2-(ω-carboxyheptanoylamino)ethoxy]ethoxy}-ethylcarbamoyl)propionyl) desB30 human insulin;

N$^{\epsilon B29}$-(3-(2-{2-[2-(ω-carboxyheptadecanoylamino)ethoxy]ethoxy}-ethylcarbamoyl)propionyl-γ-glutamyl) desB30 human insulin;

N$^{\epsilon B29}$-(3-(2-{2-[2-(ω-carboxyhexadecanoylamino)ethoxy]ethoxy}-ethylcarbamoyl)propionyl-γ-glutamyl) desB30 human insulin;

N$^{\epsilon B29}$-(3-(2-{2-[2-(ω-carboxypentadecanoylamino)ethoxy]ethoxy}-ethylcarbamoyl)propionyl-γ-glutamyl) desB30 human insulin;

N$^{\epsilon B29}$-(3-(2-{2-[2-(ω-carboxytridecanoylamino)ethoxy]ethoxy}-ethylcarbamoyl)propionyl-γ-glutamyl) desB30 human insulin;

N$^{\epsilon B29}$-(3-(2-{2-[2-(ω-carboxyundecanoylamino)ethoxy]ethoxy}-ethylcarbamoyl)propionyl-γ-glutamyl) desB30 human insulin;

N$^{\epsilon B29}$-(3-(2-{2-[2-(ω-carboxynonanoylamino)ethoxy]ethoxy}-ethylcarbamoyl)propionyl-γ-glutamyl) desB30 human insulin N$^{\epsilon B29}$-(3-(2-{2-[2-(ω-carboxyheptanoylamino)ethoxy]ethoxy}-ethylcarbamoyl)propionyl-γ-glutamyl) desB30 human insulin;

N$^{\epsilon B29}$-(3-[3-(2-{2-[3-(ω-carboxyheptadecanoylamino)propoxy]ethoxy}ethoxy)-propylcarbamoyl]propionyl-γ-glutamyl) desB30 human insulin;

N$^{\epsilon B29}$-(3-[3-(2-{2-[3-(ω-carboxypentadecanoylamino)propoxy]ethoxy}ethoxy)-propylcarbamoyl]propionyl-γ-glutamyl) desB30 human insulin;

N$^{\epsilon B29}$-(3-[3-(2-{2-[3-(ω-carboxypentadecanoylamino)propoxy]ethoxy}ethoxy)-propylcarbamoyl]propionyl-γ-glutamyl) desB30 human insulin;

N$^{\epsilon B29}$-(3-[3-(2-{2-[3-(ω-carboxytridecanoylamino)propoxy]ethoxy}ethoxy)-propylcarbamoyl]propionyl-γ-glutamyl) desB30 human insulin;

N$^{\epsilon B29}$-(3-[3-(2-{2-[3-(ω-carboxyundecanoylamino)propoxy]ethoxy}ethoxy)-propylcarbamoyl]propionyl-γ-glutamyl) desB30 human insulin;

N$^{\epsilon B29}$-(3-[3-(2-{2-[3-(ω-carboxynonanoylamino)propoxy]ethoxy}ethoxy)-propylcarbamoyl]propionyl-γ-glutamyl) desB30 human insulin;

N$^{\epsilon B29}$-(3-[3-(2-{2-[3-(ω-carboxyheptanoylamino)propoxy]ethoxy}ethoxy)-propylcarbamoyl]propionyl-γ-glutamyl) desB30 human insulin;

N$^{\epsilon B29}$-(3-[3-(2-{2-[3-(ω-carboxyheptadecanoylamino)propoxy]ethoxy}ethoxy)-propylcarbamoyl]propionyl) desB30 human insulin;

N$^{\epsilon B29}$-(3-[3-(2-{2-[3-(ω-carboxyhexadecanoylamino)propoxy]ethoxy}ethoxy)-propylcarbamoyl]propionyl) desB30 human insulin;

N$^{\epsilon B29}$-(3-[3-(2-{2-[3-(ω-carboxypentadecanoylamino)propoxy]ethoxy}ethoxy)-propylcarbamoyl]propionyl) desB30 human insulin;

N$^{\epsilon B29}$-(3-[3-(2-{2-[3-(ω-carboxytridecanoylamino)propoxy]ethoxy}ethoxy)-propylcarbamoyl]propionyl) desB30 human insulin;

N$^{\epsilon B29}$-(3-[3-(2-{2-[3-(ω-carboxyundecanoylamino)propoxy]ethoxy}ethoxy)-propylcarbamoyl]propionyl) desB30 human insulin;

N$^{\epsilon B29}$-(3-[3-(2-{2-[3-(ω-carboxynonanoylamino)propoxy]ethoxy}ethoxy)-propylcarbamoyl]propionyl) desB30 human insulin;

N$^{\epsilon B29}$-(3-[3-(2-{2-[3-(ω-carboxyheptanoylamino)propoxy]ethoxy}ethoxy)-propylcarbamoyl]propionyl) desB30 human insulin;

$N^{\epsilon B29}$-(3-[3-(2-{2-[2-(ω-carboxyheptadecanoylamino)ethoxy]ethoxy}ethoxy)-ethoxy]propionyl-γ-glutamyl) human insulin;

$N^{\epsilon B29}$-(3-[3-(2-{2-[2-(ω-carboxyhexadecanoylamino)ethoxy]ethoxy}ethoxy)-ethoxy]propionyl-γ-glutamyl) human insulin;

$N^{\epsilon B29}$-(3-[3-(2-{2-[2-(ω-carboxytridecanoylamino)ethoxy]ethoxy}ethoxy)-ethoxy]propionyl-γ-glutamyl) human insulin;

$N^{\epsilon B29}$-(3-[3-(2-{2-[2-(ω-carboxyundecanoylamino)ethoxy]ethoxy}ethoxy)-ethoxy]propionyl-γ-glutamyl) human insulin;

$N^{\epsilon B29}$-(3-[3-(2-{2-[2-(ω-carboxynonanoylamino)ethoxy]ethoxy}ethoxy)-ethoxy]propionyl-γ-glutamyl) human insulin;

$N^{\epsilon B29}$-(3-[3-(2-{2-[2-(ω-carboxyheptanoylamino)ethoxy]ethoxy}ethoxy)-ethoxy]propionyl-γ-glutamyl) human insulin;

$N^{\epsilon B29}$-(3-[3-(2-{2-[2-(ω-carboxyheptadecanoylamino)ethoxy]ethoxy}ethoxy)-ethoxy]propionyl) human insulin;

$N^{\epsilon B29}$-(3-[3-(2-{2-[2-(ω-carboxyhexadecanoylamino)ethoxy]ethoxy}ethoxy)ethoxy]propionyl) human insulin $N^{\epsilon B29}$-(3-[3-(2-{2-[2-(ω-carboxytridecanoylamino)ethoxy]ethoxy}ethoxy)ethoxy]propionyl) human insulin $N^{\epsilon B29}$-(3-[3-(2-{2-[2-(ω-carboxyundecanoylamino)ethoxy]ethoxy}ethoxy)-ethoxy]propionyl) human insulin;

$N^{\epsilon B29}$-(3-[3-(2-{2-[2-(ω-carboxynonanoylamino)ethoxy]ethoxy}ethoxy)-ethoxy]propionyl) human insulin;

$N^{\epsilon B29}$-(3-[3-(2-{2-[2-(ω-carboxyheptanoylamino)ethoxy]ethoxy}ethoxy)-ethoxy]propionyl) human insulin;

$N^{\epsilon B29}$-(3-(3-{2-[3-(ω-carboxyheptadecanoylamino)propoxy]ethoxy}-propylcarbamoyl)propionyl) human insulin;

$N^{\epsilon B29}$-(3-(3-{2-[3-(ω-carboxyhexadecanoylamino)propoxy]ethoxy}-propylcarbamoyl)propionyl) human insulin;

$N^{\epsilon B29}$-(3-(3-{2-[3-(ω-carboxypentadecanoylamino)propoxy]ethoxy}-propylcarbamoyl)propionyl) human insulin;

$N^{\epsilon B29}$-(3-(3-{2-[3-(ω-carboxytridecanoylamino)propoxy]ethoxy}-propylcarbamoyl)propionyl) human insulin;

$N^{\epsilon B29}$-(3-(3-{2-[3-(ω-carboxyundecanoylamino)propoxy]ethoxy}-propylcarbamoyl)propionyl) human insulin;

$N^{\epsilon B29}$-(3-(3-{2-[3-(ω-carboxynonanoylamino)propoxy]ethoxy}-propylcarbamoyl)propionyl) human insulin;

$N^{\epsilon B29}$-(3-(3-{2-[3-(ω-carboxyheptanoylamino)propoxy]ethoxy}-propylcarbamoyl)propionyl) human insulin;

$N^{\epsilon B29}$-(3-(3-{2-[3-(ω-carboxyheptadecanoylamino)propoxy]ethoxy}-propylcarbamoyl)propionyl-γ-glutamyl) human insulin;

$N^{\epsilon B29}$-(3-(3-{2-[3-(ω-carboxyhexadecanoylamino)propoxy]ethoxy}-propylcarbamoyl)propionyl-γ-glutamyl) human insulin;

$N^{\epsilon B29}$-(3-(3-{2-[3-(ω-carboxypentadecanoylamino)propoxy]ethoxy}-propylcarbamoyl)propionyl-γ-glutamyl) human insulin;

$N^{\epsilon B29}$-(3-(3-{2-[3-(ω-carboxytridecanoylamino)propoxy]ethoxy}-propylcarbamoyl)propionyl-γ-glutamyl) human insulin;

$N^{\epsilon B29}$-(3-(3-{2-[3-(ω-carboxyundecanoylamino)propoxy]ethoxy}-propylcarbamoyl)propionyl-γ-glutamyl) human insulin;

$N^{\epsilon B29}$-(3-(3-{2-[3-(ω-carboxynonanoylamino)propoxy]ethoxy}propylcarbamoyl)propionyl-γ-glutamyl) human insulin $N^{\epsilon B29}$-(3-(3-{2-[3-(ω-carboxyheptanoylamino)propoxy]ethoxy}-propylcarbamoyl)propionyl-γ-glutamyl) human insulin;

$N^{\epsilon B29}$-(3-(2-{2-[2-(ω-carboxypentadecanoylamino)ethoxy]ethoxy}-ethylcarbamoyl)propionyl) human insulin;

$N^{\epsilon B29}$-(3-(2-{2-[2-(ω-carboxyhexadecanoylamino)ethoxy]ethoxy}-ethylcarbamoyl)propionyl) human insulin;

$N^{\epsilon B29}$-(3-(2-{2-[2-(ω-carboxypentadecanoylamino)ethoxy]ethoxy}-ethylcarbamoyl)propionyl) human insulin;

$N^{\epsilon B29}$-(3-(2-{2-[2-(ω-carboxytridecanoylamino)ethoxy]ethoxy}-ethylcarbamoyl)propionyl) human insulin;

$N^{\epsilon B29}$-(3-(2-{2-[2-(ω-carboxyundecanoylamino)ethoxy]ethoxy}-ethylcarbamoyl)propionyl) human insulin;

$N^{\epsilon B29}$-(3-(2-{2-[2-(ω-carboxynonanoylamino)ethoxy]ethoxy}-ethylcarbamoyl)propionyl) human insulin;

$N^{\epsilon B29}$-(3-(2-{2-[2-(ω-carboxyheptanoylamino)ethoxy]ethoxy}-ethylcarbamoyl)propionyl) human insulin;

$N^{\epsilon B29}$-(3-(2-{2-[2-(ω-carboxyheptadecanoylamino)ethoxy]ethoxy}-ethylcarbamoyl)propionyl-γ-glutamyl) human insulin;

$N^{\epsilon B29}$-(3-(2-{2-[2-(ω-carboxyhexadecanoylamino)ethoxy]ethoxy}-ethylcarbamoyl)propionyl-γ-glutamyl) human insulin;

$N^{\epsilon B29}$-(3-(2-{2-[2-(ω-carboxypentadecanoylamino)ethoxy]ethoxy}-ethylcarbamoyl)propionyl-γ-glutamyl) human insulin;

$N^{\epsilon B29}$-(3-(2-{2-[2-(ω-carboxytridecanoylamino)ethoxy]ethoxy}ethylcarbamoyl)-propionyl-γ-glutamyl) human insulin;

$N^{\epsilon B29}$-(3-(2-{2-[2-(ω-carboxyundecanoylamino)ethoxy]ethoxy}ethylcarbamoyl)propionyl-γ-glutamyl) human insulin $N^{\epsilon B29}$-(3-(2-{2-[2-(ω-carboxynonanoylamino)ethoxy]ethoxy}ethylcarbamoyl)-propionyl-γ-glutamyl) human insulin;

$N^{\epsilon B29}$-(3-(2-{2-[2-(ω-carboxyheptanoylamino)ethoxy]ethoxy}ethylcarbamoyl)-propionyl-γ-glutamyl) human insulin;

$N^{\epsilon B29}$-(3-[3-(2-{2-[3-(ω-carboxyheptadecanoylamino)propoxy]ethoxy}ethoxy)-propylcarbamoyl]propionyl-γ-glutamyl) human insulin;

$N^{\epsilon B29}$-(3-[3-(2-{2-[3-(ω-carboxypentadecanoylamino)propoxy]ethoxy}ethoxy)-propylcarbamoyl]propionyl-γ-glutamyl) human insulin;

$N^{\epsilon B29}$-(3-[3-(2-{2-[3-(ω-carboxypentadecanoylamino)propoxy]ethoxy}ethoxy)-propylcarbamoyl]propionyl-γ-glutamyl) human insulin;

$N^{\epsilon B29}$-(3-[3-(2-{2-[3-(ω-carboxytridecanoylamino)propoxy]ethoxy}ethoxy)-propylcarbamoyl]propionyl-γ-glutamyl) human insulin;

$N^{\epsilon B29}$-(3-[3-(2-{2-[3-(ω-carboxyundecanoylamino)propoxy]ethoxy}ethoxy)-propylcarbamoyl]propionyl-γ-glutamyl) human insulin;

$N^{\epsilon B29}$-(3-[3-(2-{2-[3-(ω-carboxynonanoylamino)propoxy]ethoxy}ethoxy)-propylcarbamoyl]propionyl-γ-glutamyl) human insulin;

$N^{\epsilon B29}$-(3-[3-(2-{2-[3-(ω-carboxyheptanoylamino)propoxy]ethoxy}ethoxy)-propylcarbamoyl]propionyl-γ-glutamyl) human insulin;

$N^{\epsilon B29}$-(3-[3-(2-{2-[3-(ω-carboxyheptadecanoylamino)propoxy]ethoxy}ethoxy)-propylcarbamoyl]propionyl) human insulin;

$N^{\epsilon B29}$-(3-[3-(2-{2-[3-(ω-carboxyhexadecanoylamino)propoxy]ethoxy}ethoxy)-propylcarbamoyl]propionyl) human insulin;

N$^{\epsilon B29}$-(3-[3-(2-{2-[3-(ω-carboxypentadecanoylamino)propoxy]ethoxy}ethoxy)-propylcarbamoyl]propionyl) human insulin;

N$^{\epsilon B29}$-(3-[3-(2-{2-[3-(ω-carboxytridecanoylamino)propoxy]ethoxy}ethoxy)-propylcarbamoyl]propionyl) human insulin;

N$^{\epsilon B29}$-(3-[3-(2-{2-[3-(ωcarboxyundecanoylamino)propoxy]ethoxy}ethoxy)-propylcarbamoyl]propionyl) human insulin;

N$^{\epsilon B29}$-(3-[3-(2-{2-[3-(ω-carboxynonanoylamino)propoxy]ethoxy}ethoxy)-propylcarbamoyl]propionyl) human insulin;

N$^{\epsilon B29}$-(3-[3-(2-{2-[3-(ω-carboxyheptanoylamino)propoxy]ethoxy}ethoxy)-propylcarbamoyl]propionyl) human insulin:

N$^{\epsilon B29}$-(3-[2-(2-{2-[2-(ω-carboxyheptadecanoylamino)ethoxy]ethoxy}ethoxy)-ethoxy]propionyl-γ-glutamyl) B28D human insulin;

N$^{\epsilon B29}$-(3-[2-(2-{2-[2-(ω-carboxyhexadecanoylamino)ethoxy]ethoxy}ethoxy)-ethoxy]propionyl-γ-glutamyl) B28D human insulin;

N$^{\epsilon B29}$-(3-[2-(2-{2-[2-(ω-carboxytridecanoylamino)ethoxy]ethoxy}ethoxy)-ethoxy]propionyl-γ-glutamyl) B28D human insulin;

N$^{\epsilon B29}$-(3-[2-(2-{2-[2-(ω-carboxyundecanoylamino)ethoxy]ethoxy}ethoxy)-ethoxy]propionyl-γ-glutamyl) B28D human insulin;

N$^{\epsilon B29}$-(3-[2-(2-{2-[2-(ω-carboxynonanoylamino)ethoxy]ethoxy}ethoxy)-ethoxy]propionyl-γ-glutamyl) B28D human insulin;

N$^{\epsilon B29}$-(3-[2-(2-{2-[2-(ω-carboxyheptanoylamino)ethoxy]ethoxy}ethoxy)-ethoxy]propionyl-γ-glutamyl) B28D human insulin;

N$^{\epsilon B29}$-(3-[2-(2-{2-[2-(ω-carboxyheptadecanoylamino)ethoxy]ethoxy}ethoxy)-ethoxy]propionyl) B28D human insulin;

N$^{\epsilon B29}$-(3-[2-(2-{2-[2-(ω-carboxyhexadecanoylamino)ethoxy]ethoxy}ethoxy)-ethoxy]propionyl) B28D human insulin;

N$^{\epsilon B29}$-(3-[2-(2-{2-[2-(ω-carboxytridecanoylamino)ethoxy]ethoxy}ethoxy)-ethoxy]propionyl) B28D human insulin;

N$^{\epsilon B29}$-(3-[2-(2-{2-[2-(ω-carboxyundecanoylamino)ethoxy]ethoxy}ethoxy)-ethoxy]propionyl) B28D human insulin;

N$^{\epsilon B29}$-(3-[2-(2-{2-[2-(ω-carboxynonanoylamino)ethoxy]ethoxy}ethoxy)-ethoxy]propionyl) B28D human insulin;

N$^{\epsilon B29}$-(3-[2-(2-{2-[2-(ω-carboxyheptanoylamino)ethoxy]ethoxy}ethoxy)-ethoxy]propionyl) B28D human insulin;

N$^{\epsilon B29}$-(3-(3-{2-[3-(ω-carboxyheptadecanoylamino)propoxy]ethoxy}-propylcarbamoyl)propionyl) B28D human insulin;

N$^{\epsilon B29}$-(3-(3-{2-[3-(ω-carboxyhexadecanoylamino)propoxy]ethoxy}-propylcarbamoyl)propionyl) B28D human insulin;

N$^{\epsilon B29}$-(3-(3-{2-[3-(ω-carboxypentadecanoylamino)propoxy]ethoxy}-propylcarbamoyl)propionyl) B28D human insulin;

N$^{\epsilon B29}$-(3-(3-{2-[3-(ω-carboxytridecanoylamino)propoxy]ethoxy}-propylcarbamoyl)propionyl) B28D human insulin;

N$^{\epsilon B29}$-(3-(3-{2-[3-(ω-carboxyundecanoylamino)propoxy]ethoxy}-propylcarbamoyl)propionyl) B28D human insulin;

N$^{\epsilon B29}$-(3-(3-{2-[3-(ω-carboxynonanoylamino)propoxy]ethoxy}-propylcarbamoyl)propionyl) B28D human insulin;

N$^{\epsilon B29}$-(3-(3-{2-[3-(ω-carboxyheptanoylamino)propoxy]ethoxy}-propylcarbamoyl)propionyl) B28D human insulin;

N$^{\epsilon B29}$-(3-(3-{2-[3-(ω-carboxyheptadecanoylamino)propoxy]ethoxy}-propylcarbamoyl)propionyl-γ-glutamyl) B28D human insulin;

N$^{\epsilon B29}$-(3-(3-{2-[3-(ω-carboxyhexadecanoylamino)propoxy]ethoxy}-propylcarbamoyl)propionyl-γ-glutamyl) B28D human insulin;

N$^{\epsilon B29}$-(3-(3-{2-[3-(ω-carboxypentadecanoylamino)propoxy]ethoxy}-propylcarbamoyl)propionyl-γ-glutamyl) B28D human insulin;

N$^{\epsilon B29}$-(3-(3-{2-[3-(ω-carboxytridecanoylamino)propoxy]ethoxy}-propylcarbamoyl)propionyl-γ-glutamyl) B28D human insulin;

N$^{\epsilon B29}$-(3-(3-{2-[3-(ω-carboxyundecanoylamino)propoxy]ethoxy}-propylcarbamoyl)propionyl-γ-glutamyl) B28D human insulin;

N$^{\epsilon B29}$-(3-(3-{2-[3-(ω-carboxynonanoylamino)propoxy]ethoxy}-propylcarbamoyl)propionyl-γ-glutamyl) B28D human insulin;

N$^{\epsilon B29}$-(3-(3-{2-[3-(ω-carboxyheptanoylamino)propoxy]ethoxy}-propylcarbamoyl)propionyl-γ-glutamyl) B28D human insulin;

N$^{\epsilon B29}$-(3-(2-{2-[2-(ω-carboxypentadecanoylamino)ethoxy]ethoxy}-ethylcarbamoyl)propionyl) B28D human insulin;

N$^{\epsilon B29}$-(3-(2-{2-[2-(ω-carboxyhexadecanoylamino)ethoxy]ethoxy}-ethylcarbamoyl)propionyl) B28D human insulin;

N$^{\epsilon B29}$-(3-(2-{2-[2-(ω-carboxypentadecanoylamino)ethoxy]ethoxy}-ethylcarbamoyl)propionyl) B28D human insulin;

N$^{\epsilon B29}$-(3-(2-{2-[2-(ω-carboxytridecanoylamino)ethoxy]ethoxy}ethylcarbamoyl)-propionyl) B28D human insulin;

N$^{\epsilon B29}$-(3-(2-{2-[2-(ω-carboxyundecanoylamino)ethoxy]ethoxy}-ethylcarbamoyl)propionyl) B28D human insulin;

N$^{\epsilon B29}$-(3-(2-{2-[2-(ω-carboxynonanoylamino)ethoxy]ethoxy}ethylcarbamoyl)-propionyl) B28D human insulin;

N$^{\epsilon B29}$-(3-(2-{2-[2-(ω-carboxyheptanoylamino)ethoxy]ethoxy}ethylcarbamoyl)-propionyl) B28D human insulin;

N$^{\epsilon B29}$-(3-(2-{2-[2-(ω-carboxyheptadecanoylamino)ethoxy]ethoxy}-ethylcarbamoyl)propionyl-γ-glutamyl) B28D human insulin;

N$^{\epsilon B29}$-(3-(2-{2-[2-(ω-carboxyhexadecanoylamino)ethoxy]ethoxy}-ethylcarbamoyl)propionyl-γ-glutamyl) B28D human insulin;

N$^{\epsilon B29}$-(3-(2-{2-[2-(ω-carboxypentadecanoylamino)ethoxy]ethoxy}-ethylcarbamoyl)propionyl-γ-glutamyl) B28D human insulin;

N$^{\epsilon B29}$-(3-(2-{2-[2-(ω-carboxytridecanoylamino)ethoxy]ethoxy}ethylcarbamoyl)-propionyl-γ-glutamyl) B28D human insulin;

N$^{\epsilon B29}$-(3-(2-{2-[2-(ω-carboxyundecanoylamino)ethoxy]ethoxy}-ethylcarbamoyl)propionyl-γ-glutamyl) B28D human insulin;

N$^{\epsilon B29}$-(3-(2-{2-[2-(ω-carboxynonanoylamino)ethoxy]ethoxy}ethylcarbamoyl)-propionyl-γ-glutamyl) B28D human insulin;

N$^{\epsilon B29}$-(3-(2-{2-[2-(ω-carboxyheptanoylamino)ethoxy]ethoxy}ethylcarbamoyl)-propionyl-γ-glutamyl) B28D human insulin;

N$^{\epsilon B29}$-(3-[3-(2-{2-[3-(ω-carboxyheptadecanoylamino)propoxy]ethoxy}ethoxy)-propylcarbamoyl]propionyl-γ-glutamyl) B28D human insulin;

N$^{\epsilon B29}$-(3-[3-(2-{2-[3-(ω-carboxypentadecanoylamino)propoxy]ethoxy}ethoxy)-propylcarbamoyl]propionyl-γ-glutamyl) B28D human insulin;

N$^{\epsilon B29}$-(3-[3-(2-{2-[3-(ω-carboxypentadecanoylamino)propoxy]ethoxy}ethoxy)-propylcarbamoyl]propionyl-γ-glutamyl) B28D human insulin;

N$^{\epsilon B29}$-(3-[3-(2-{2-[3-(ω-carboxytridecanoylamino)propoxy]ethoxy}ethoxy)-propylcarbamoyl]propionyl-γ-glutamyl) B28D human insulin;

N$^{\epsilon B29}$-(3-[3-(2-{2-[3-(ω-carboxyundecanoylamino)propoxy]ethoxy}ethoxy)-propylcarbamoyl]propionyl-γ-glutamyl) B28D human insulin;

N$^{\epsilon B29}$-(3-[3-(2-{2-[3-(ω-carboxynonanoylamino)propoxy]ethoxy}ethoxy)-propylcarbamoyl]propionyl-γ-glutamyl) B28D human insulin;

N$^{\epsilon B29}$-(3-[3-(2-{2-[3-(ω-carboxyheptanoylamino)propoxy]ethoxy}ethoxy)-propylcarbamoyl]propionyl-γ-glutamyl) B28D human insulin;

N$^{\epsilon B29}$-(3-[3-(2-{2-[3-(ω-carboxyheptadecanoylamino)propoxy]ethoxy}ethoxy)-propylcarbamoyl]propionyl) B28D human insulin;

N$^{\epsilon B29}$-(3-[3-(2-{2-[3-(ω-carboxyhexadecanoylamino)propoxy]ethoxy}ethoxy)-propylcarbamoyl]propionyl) B28D human insulin;

N$^{\epsilon B29}$-(3-[3-(2-{2-[3-(ω-carboxypentadecanoylamino)propoxy]ethoxy}ethoxy)-propylcarbamoyl]propionyl) B28D human insulin;

N$^{\epsilon B29}$-(3-[3-(2-{2-[3-(ω-carboxytridecanoylamino)propoxy]ethoxy}ethoxy)-propylcarbamoyl]propionyl) B28D human insulin;

N$^{\epsilon B29}$-(3-[3-(2-{2-[3-(ω-carboxyundecanoylamino)propoxy]ethoxy}ethoxy)-propylcarbamoyl]propionyl) B28D human insulin;

N$^{\epsilon B29}$-(3-[3-(2-{2-[3-(ω-carboxynonanoylamino)propoxy]ethoxy}ethoxy)-propylcarbamoyl]propionyl) B28D human insulin;

N$^{\epsilon B29}$-(3-[3-(2-{2-[3-(ω-carboxyheptanoylamino)propoxy]ethoxy}ethoxy)-propylcarbamoyl]propionyl) B28D human insulin;

N$^{\epsilon B29}$-(3-[3-(2-{2-[3-(ω-carboxyheptadecanoylamino)ethoxy]ethoxy}ethoxy)-ethoxy]propionyl-γ-glutamyl) B28D, desB30 human insulin;

N$^{\epsilon B29}$-(3-[2-(2-{2-[2-(ω-carboxyhexadecanoylamino)ethoxy]ethoxy}ethoxy)-ethoxy]propionyl-γ-glutamyl) B28D, desB30 human insulin;

N$^{\epsilon B29}$-(3-[2-(2-{2-[2-(ω-carboxytridecanoylamino)ethoxy]ethoxy}ethoxy)-ethoxy]propionyl-γ-glutamyl) B28D, desB30 human insulin;

N$^{\epsilon B29}$-(3-[2-(2-{2-[2-(ω-carboxyundecanoylamino)ethoxy]ethoxy}ethoxy)-ethoxy]propionyl-γ-glutamyl) B28D, desB30 human insulin;

N$^{\epsilon B29}$-(3-[2-(2-{2-[2-(ω-carboxynonanoylamino)ethoxy]ethoxy}ethoxy)-ethoxy]propionyl-γ-glutamyl) B28D, desB30 human insulin;

N$^{\epsilon B29}$-(3-[2-(2-{2-[2-(ω-carboxyheptanoylamino)ethoxy]ethoxy}ethoxy]-propionyl-γ-glutamyl) B28D, desB30 human insulin;

N$^{\epsilon B29}$-(3-[2-(2-{2-[2-(ω-carboxyheptadecanoylamino)ethoxy]ethoxy}ethoxy)-ethoxy]propionyl) B28D, desB30 human insulin;

N$^{\epsilon B29}$-(3-[2-(2-{2-[2-(ω-carboxyhexadecanoylamino)ethoxy]ethoxy}ethoxy)-ethoxy]propionyl) B28D, desB30 human insulin;

N$^{\epsilon B29}$-(3-[2-(2-{2-[2-(ω-carboxytridecanoylamino)ethoxy]ethoxy}ethoxy)-ethoxy]propionyl) B28D, desB30 human insulin;

N$^{\epsilon B29}$-(3-[2-(2-{2-[2-(ω-carboxyundecanoylamino)ethoxy]ethoxy}ethoxy)-ethoxy]propionyl) B28D, desB30 human insulin;

N$^{\epsilon B29}$-(3-[2-(2-{2-[2-(ω-carboxynonanoylamino)ethoxy]ethoxy}ethoxy)-ethoxy]propionyl) B28D, desB30 human insulin;

N$^{\epsilon B29}$-(3-[2-(2-{2-[2-(ω-carboxyheptanoylamino)ethoxy]ethoxy}ethoxy)-ethoxy]propionyl) B28D, desB30 human insulin;

N$^{\epsilon B29}$-(3-(3-{2-[3-(ω-carboxyheptadecanoylamino)propoxy]ethoxy}-propylcarbamoyl)propionyl) B28D, desB30 human insulin;

N$^{\epsilon B29}$-(3-(3-{2-[3-(ω-carboxyhexadecanoylamino)propoxy]ethoxy}propylcarbamoyl)propionyl) B28D, desB30 human insulin;

N$^{\epsilon B29}$-(3-(3-{2-[3-(ω-carboxypentadecanoylamino)propoxy]ethoxy}-propylcarbamoyl)propionyl) B28D, desB30 human insulin;

N$^{\epsilon B29}$-(3-(3-{2-[3-(ω-carboxytridecanoylamino)propoxy]ethoxy}-propylcarbamoyl)propionyl) B28D, desB30 human insulin;

N$^{\epsilon B29}$-(3-(3-{2-[3-(ωcarboxyundecanoylamino)propoxy]ethoxy}propylcarbamoyl)propionyl) B28D, desB30 human insulin;

N$^{\epsilon B29}$-(3-(3-{2-[3-(ω-carboxynonanoylamino)propoxy]ethoxy}-propylcarbamoyl)propionyl) B28D, desB30 human insulin;

N$^{\epsilon B29}$-(3-(3-{2-[3-(ωcarboxyheptanoylamino)propoxy]ethoxy}-propylcarbamoyl)propionyl) B28D, desB30 human insulin;

N$^{\epsilon B29}$-(3-(3-{2-[3-(ω-carboxyheptadecanoylamino)propoxy]ethoxy}-propylcarbamoyl)propionyl-γ-glutamyl) B28D, desB30 human insulin;

N$^{\epsilon B29}$-(3-(3-{2-[3-(ω-carboxyhexadecanoylamino)propoxy]ethoxy}-propylcarbamoyl)propionyl-γ-glutamyl) B28D, desB30 human insulin;

N$^{\epsilon B29}$-(3-(3-{2-[3-(ω-carboxypentadecanoylamino)propoxy]ethoxy}-propylcarbamoyl)propionyl-γ-glutamyl) B28D, desB30 human insulin;

N$^{\epsilon B29}$-(3-(3-{2-[3-(ω-carboxytridecanoylamino)propoxy]ethoxy}-propylcarbamoyl)propionyl-γ-glutamyl) B28D, desB30 human insulin;

N$^{\epsilon B29}$-(3-(3-{2-[3-(ω-carboxyundecanoylamino)propoxy]ethoxy}-propylcarbamoyl)propionyl-γ-glutamyl) B28D, desB30 human insulin;

N$^{\epsilon B29}$-(3-(3-{2-[3-(ω-carboxynonanoylamino)propoxy]ethoxy}propylcarbamoyl)propionyl-γ-glutamyl) B28D, desB30 human insulin;

N$^{\epsilon B29}$-(3-(3-{2-[3-(ω-carboxyheptanoylamino)propoxy]ethoxy}-propylcarbamoyl)propionyl-γ-glutamyl) B28D, desB30 human insulin;

N$^{\epsilon B29}$-(3-(2-{2-[2-(ω-carboxypentadecanoylamino)ethoxy]ethoxy}-ethylcarbamoyl)propionyl) B28D, desB30 human insulin;

N$^{\epsilon B29}$-(3-(2-{2-[2-(ω-carboxyhexadecanoylamino)ethoxy]ethoxy}-ethylcarbamoyl)propionyl) B28D, desB30 human insulin;

N$^{\epsilon B29}$-(3-(2-{2-[2-(ω-carboxypentadecanoylamino)ethoxy]ethoxy}-ethylcarbamoyl)propionyl) B28D, desB30 human insulin;

N$^{\epsilon B29}$-(3-(2-{2-[2-(ω-carboxytridecanoylamino)ethoxy]ethoxy}-ethylcarbamoyl)propionyl) B28D, desB30 human insulin;

N$^{\epsilon B29}$-(3-(2-{2-[2-(ω-carboxynonanoylamino)ethoxy]ethoxy}-ethylcarbamoyl)propionyl) B28D, desB30 human insulin;

N$^{\epsilon B29}$-(3-(2-{2-[2-(ω-carboxynonanoylamino)ethoxy]ethoxy}ethylcarbamoyl)propionyl) B28D, desB30 human insulin;

N$^{\epsilon B29}$-(3-(2-{2-[2-(ω-carboxyheptanoylamino)ethoxy]ethoxy}-ethylcarbamoyl)propionyl) B28D, desB30 human insulin;

N$^{\epsilon B29}$-(3-(2-{2-[2-(ω-carboxyheptadecanoylamino)ethoxy]ethoxy}-ethylcarbamoyl)propionyl-γ-glutamyl) B28D, desB30 human insulin;

N$^{\epsilon B29}$-(3-(2-{2-[2-(ω-carboxyhexadecanoylamino)ethoxy]ethoxy}-ethylcarbamoyl)propionyl-γ-glutamyl) B28D, desB30 human insulin;

N$^{\epsilon B29}$-(3-(2-{2-[2-(ω-carboxypentadecanoylamino)ethoxy]ethoxy}-ethylcarbamoyl)propionyl-γ-glutamyl) B28D, desB30 human insulin;

N$^{\epsilon B29}$-(3-(2-{2-[2-(ω-carboxytridecanoylamino)ethoxy]ethoxy}-ethylcarbamoyl)propionyl-γ-glutamyl) B28D, desB30 human insulin;

N$^{\epsilon B29}$-(3-(2-{2-[2-(ω-carboxyundecanoylamino)ethoxy]ethoxy}-ethylcarbamoyl)propionyl-γ-glutamyl) B28D, desB30 human insulin;

N$^{\epsilon B29}$-(3-(2-{2-[2-(ω-carboxynonanoylamino)ethoxy]ethoxy}-ethylcarbamoyl)propionyl-γ-glutamyl) B28D, desB30 human insulin;

N$^{\epsilon B29}$-(3-(2-{2-[2-(ω-carboxyheptanoylamino)ethoxy]ethoxy}-ethylcarbamoyl)propionyl-γ-glutamyl) B28D, desB30 human insulin;

N$^{\epsilon B29}$-(3-[3-(2-{2-[3-(ω-carboxyheptadecanoylamino)propoxy]ethoxy}-ethoxy)propylcarbamoyl]propionyl-γ-glutamyl) B28D, desB30 human insulin N$^{\epsilon B29}$-(3-[3-(2-{2-[3-(ω-carboxypentadecanoylamino)propoxy]ethoxy}ethoxy)-propylcarbamoyl]propionyl-γ-glutamyl) B28D, desB30 human insulin;

N$^{\epsilon B29}$-(3-[3-(2-{2-[3-(ω-carboxypentadecanoylamino)propoxy]ethoxy}ethoxy)-propylcarbamoyl]propionyl-γ-glutamyl) B28D, desB30 human insulin;

N$^{\epsilon B29}$-(3-[3-(2-{2-[3-(ω-carboxytridecanoylamino)propoxy]ethoxy}ethoxy)-propylcarbamoyl]propionyl-γ-glutamyl) B28D, desB30 human insulin;

N$^{\epsilon B29}$-(3-[3-(2-{2-[3-(ω-carboxyundecanoylamino)propoxy]ethoxy}ethoxy)-propylcarbamoyl]propionyl-γ-glutamyl) B28D, desB30 human insulin;

N$^{\epsilon B29}$-(3-[3-(2-{2-[3-(ω-carboxynonanoylamino)propoxy]ethoxy}ethoxy)-propylcarbamoyl]propionyl-γ-glutamyl) B28D, desB30 human insulin;

N$^{\epsilon B29}$-(3-[3-(2-{2-[3-(ω-carboxyheptanoylamino)propoxy]ethoxy}ethoxy)-propylcarbamoyl]propionyl-γ-glutamyl) B28D, desB30 human insulin;

N$^{\epsilon B29}$-(3-[3-(2-{2-[3-(ω-carboxyheptadecanoylamino)propoxy]ethoxy}-ethoxy)propylcarbamoyl]propionyl) B28D, desB30 human insulin;

N$^{\epsilon B29}$-(3-[3-(2-{2-[3-(ω-carboxyhexadecanoylamino)propoxy]ethoxy}ethoxy)-propylcarbamoyl]propionyl) B28D, desB30 human insulin;

N$^{\epsilon B29}$-(3-[3-(2-{2-[3-(ω-carboxypentadecanoylamino)propoxy]ethoxy}ethoxy)-propylcarbamoyl]propionyl) B28D, desB30 human insulin;

N$^{\epsilon B29}$-(3-[3-(2-{2-[3-(ω-carboxytridecanoylamino)propoxy]ethoxy}ethoxy)-propylcarbamoyl]propionyl) B28D, desB30 human insulin;

N$^{\epsilon B29}$-(3-[3-(2-{2-[3-(ω-carboxyundecanoylamino)propoxy]ethoxy}ethoxy)-propylcarbamoyl]propionyl) B28D, desB30 human insulin;

N$^{\epsilon B29}$-(3-[3-(2-{2-[3-(ω-carboxynonanoylamino)propoxy]ethoxy}ethoxy)-propylcarbamoyl]propionyl) B28D, desB30 human insulin; and N$^{\epsilon B29}$-(3-[3-(2-{2-[3-(ω-carboxyheptanoylamino)propoxy]ethoxy}ethoxy)-propylcarbamoyl]propionyl) B28D, desB30 human insulin Representative formulas are:

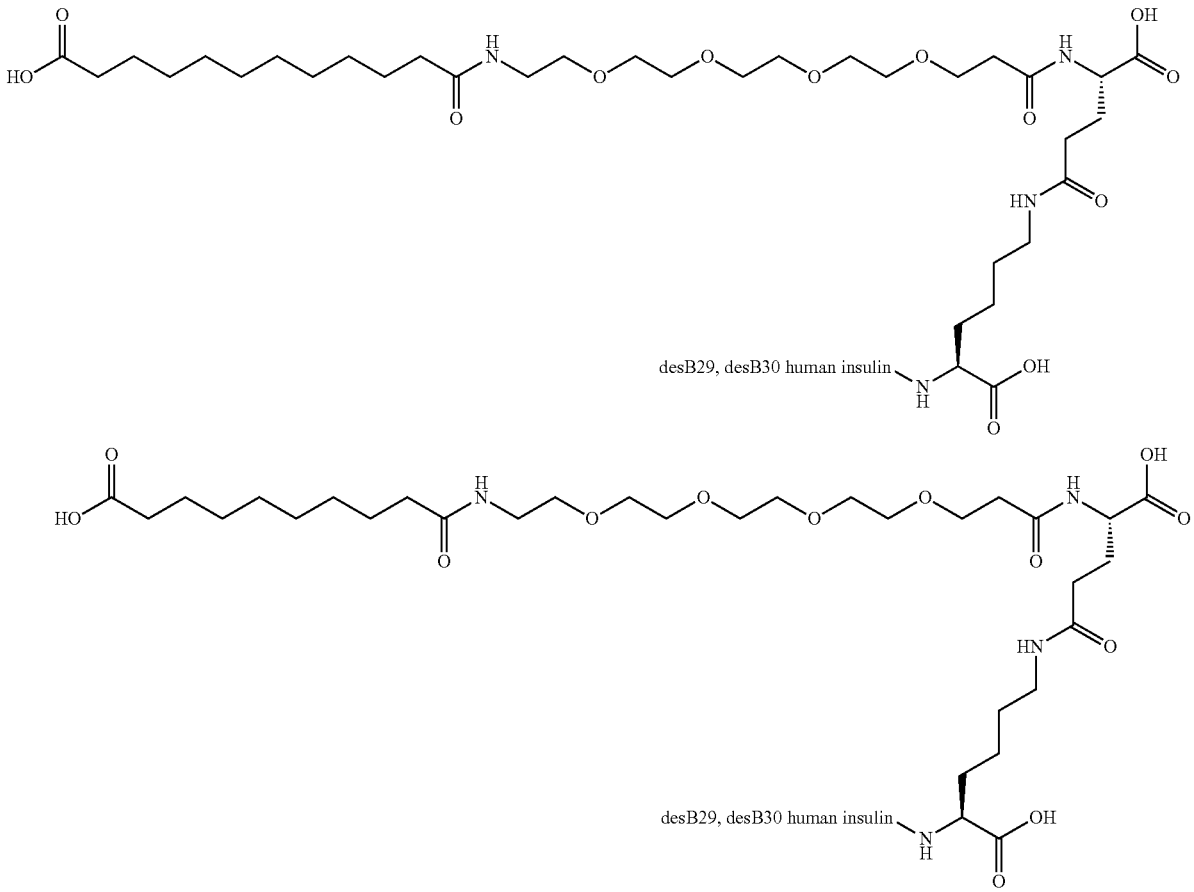

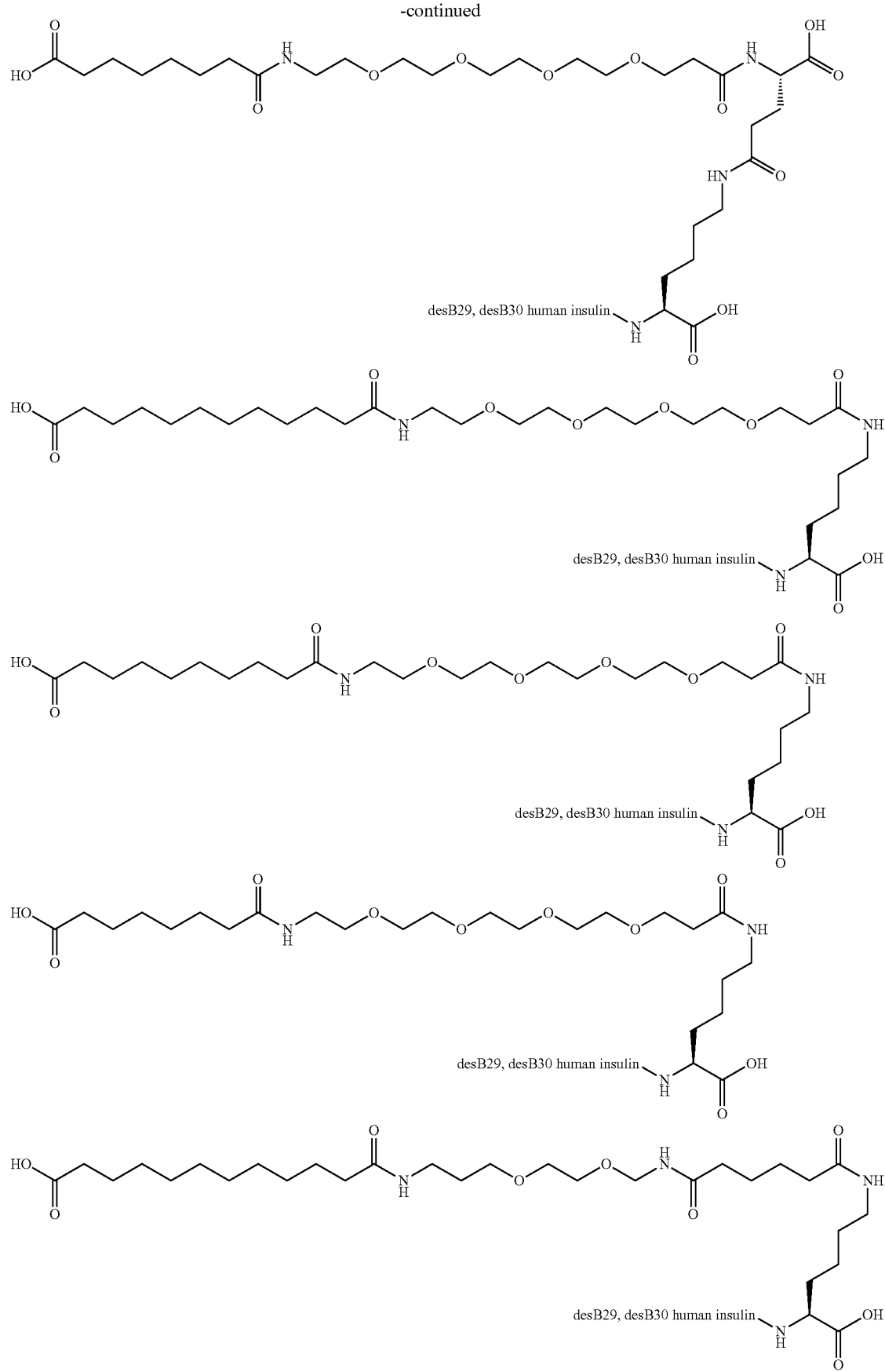

-continued
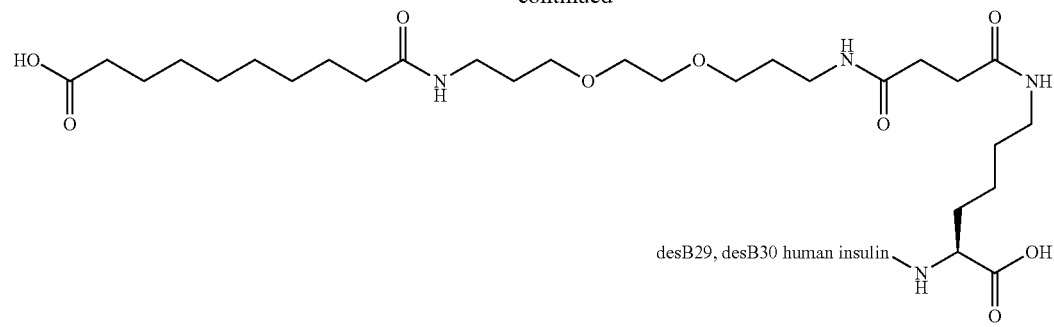
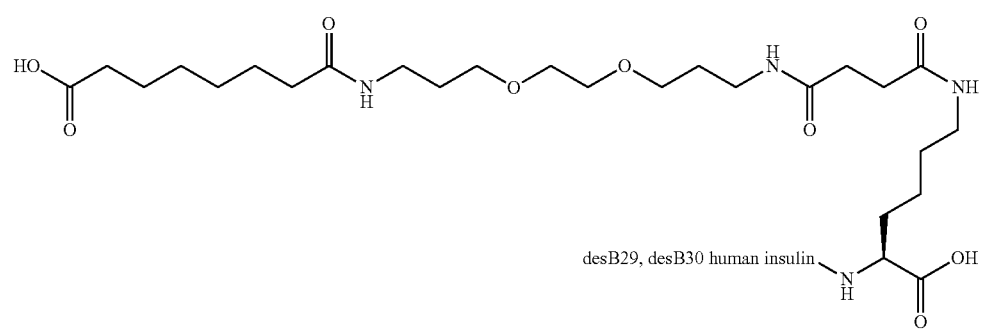
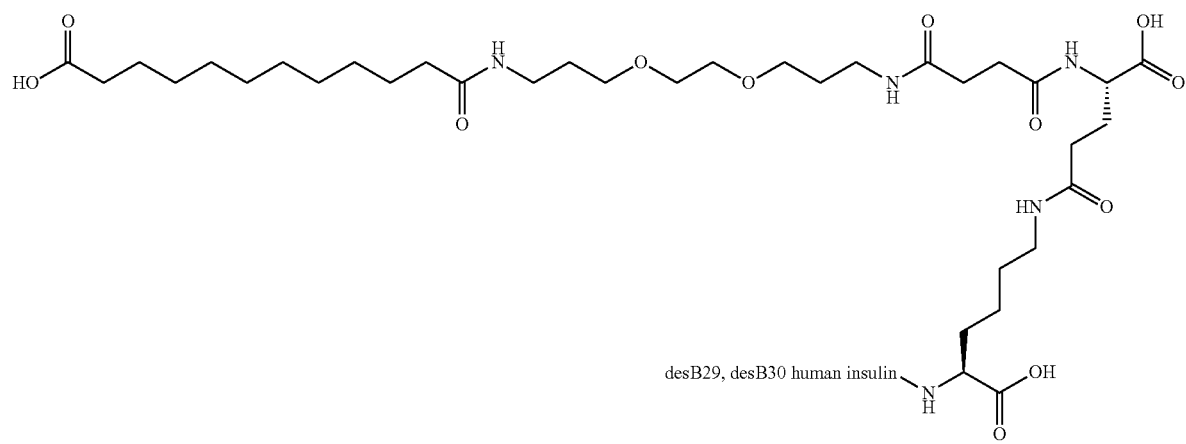
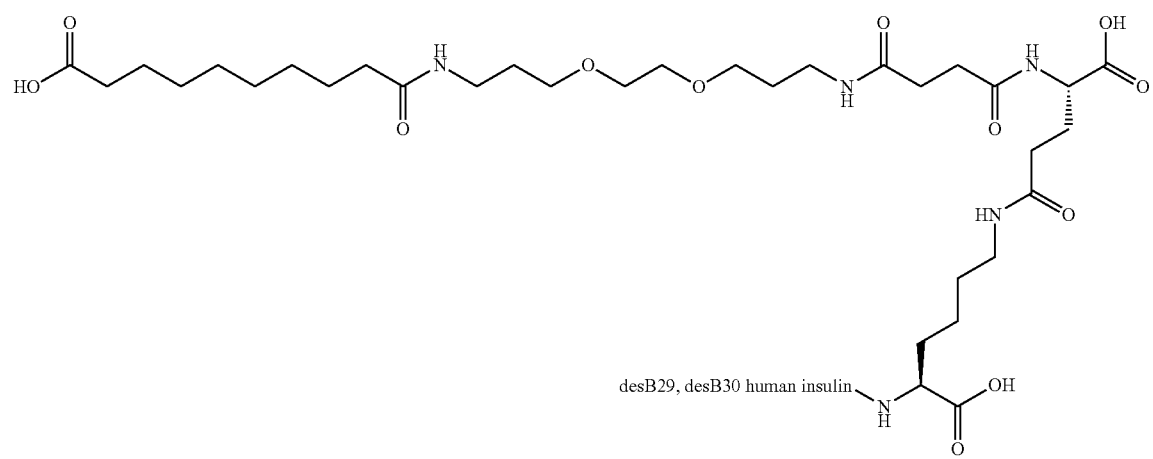

-continued
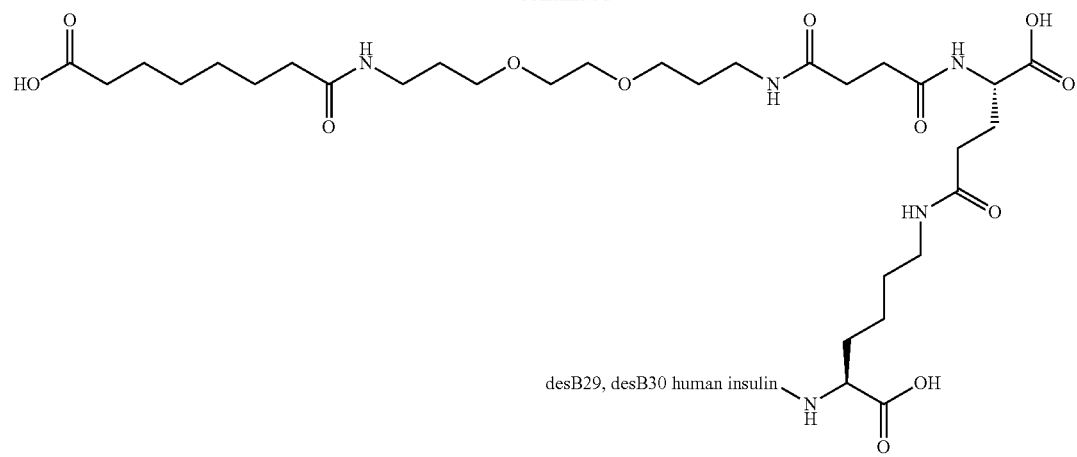
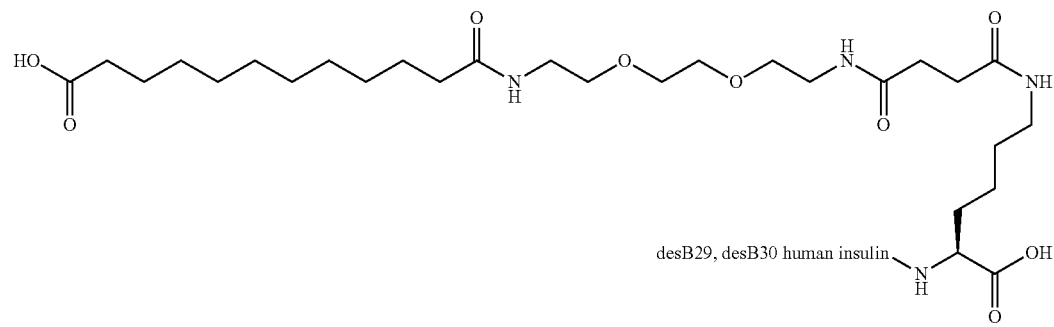
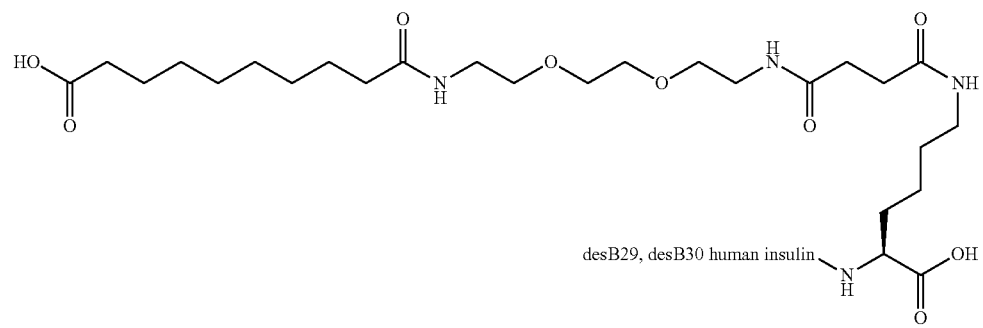
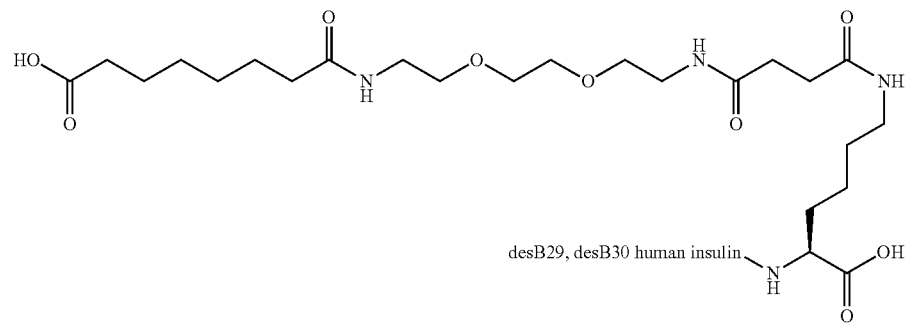

-continued
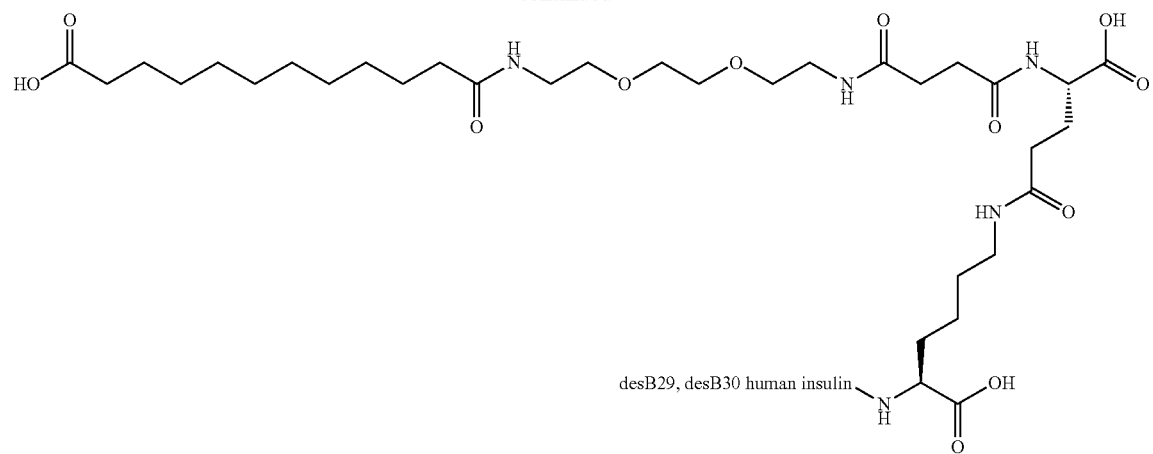
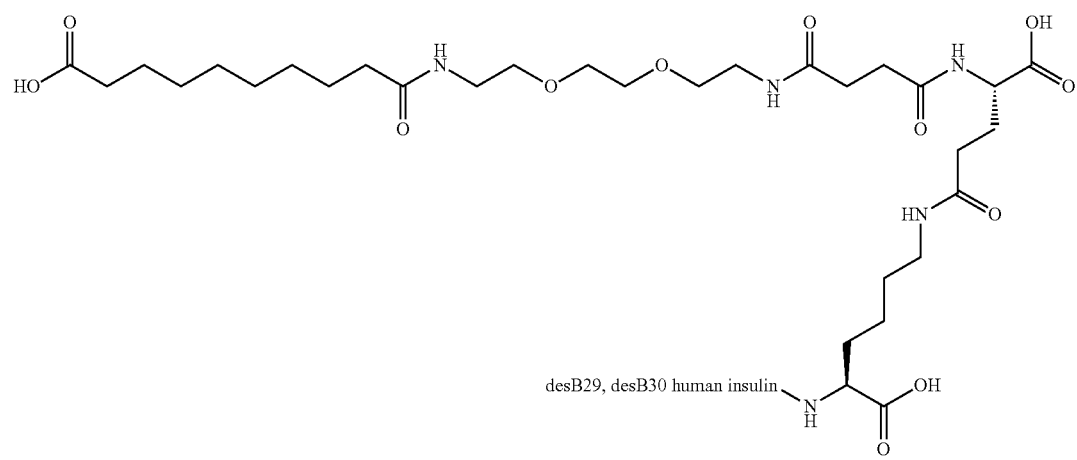
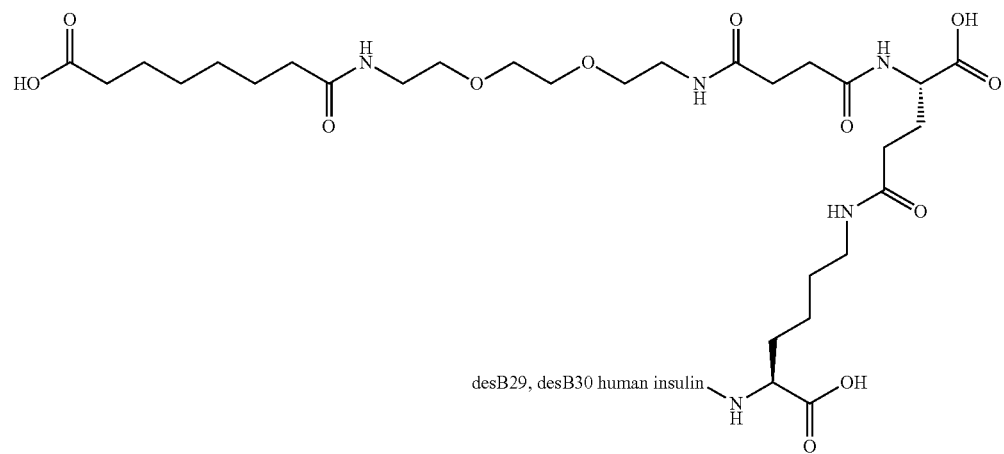

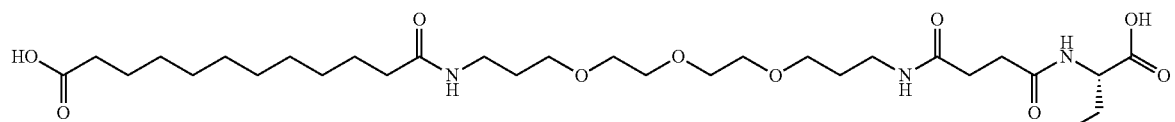
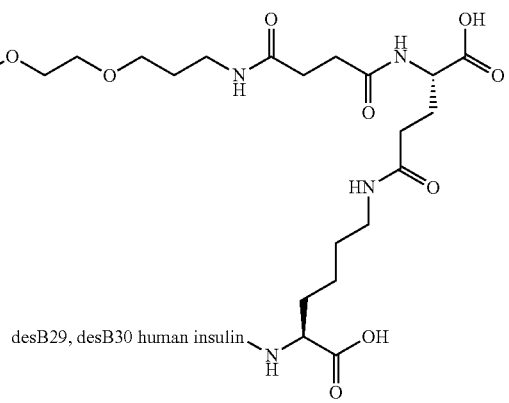
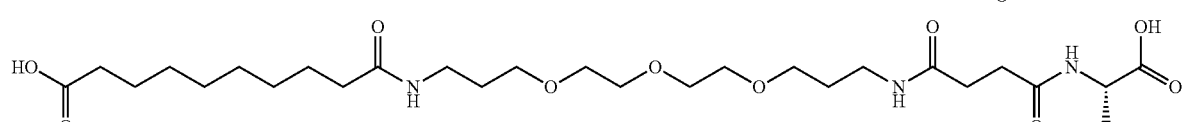
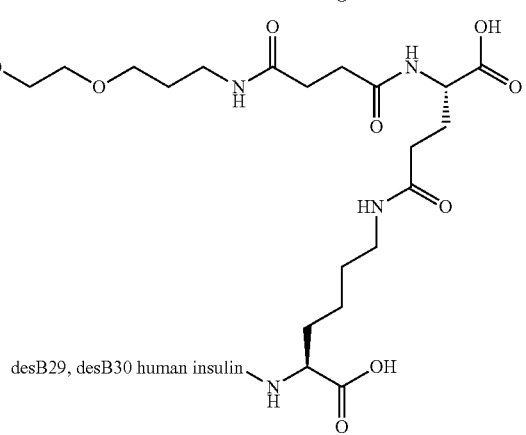
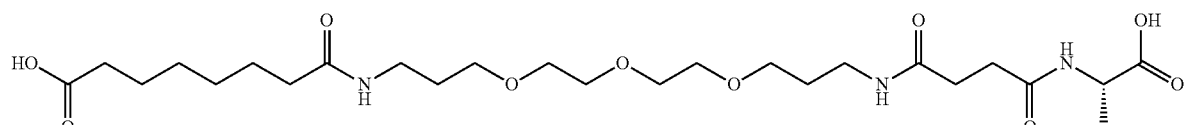
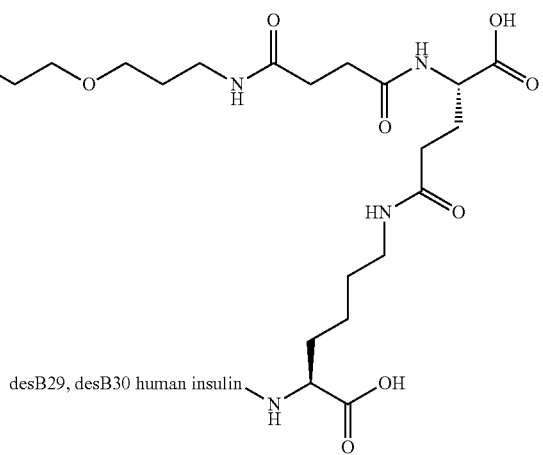
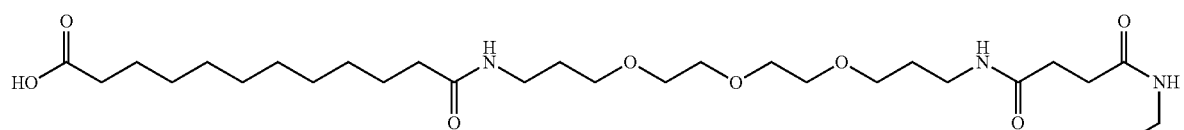
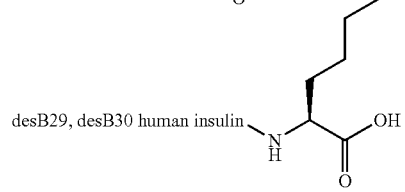

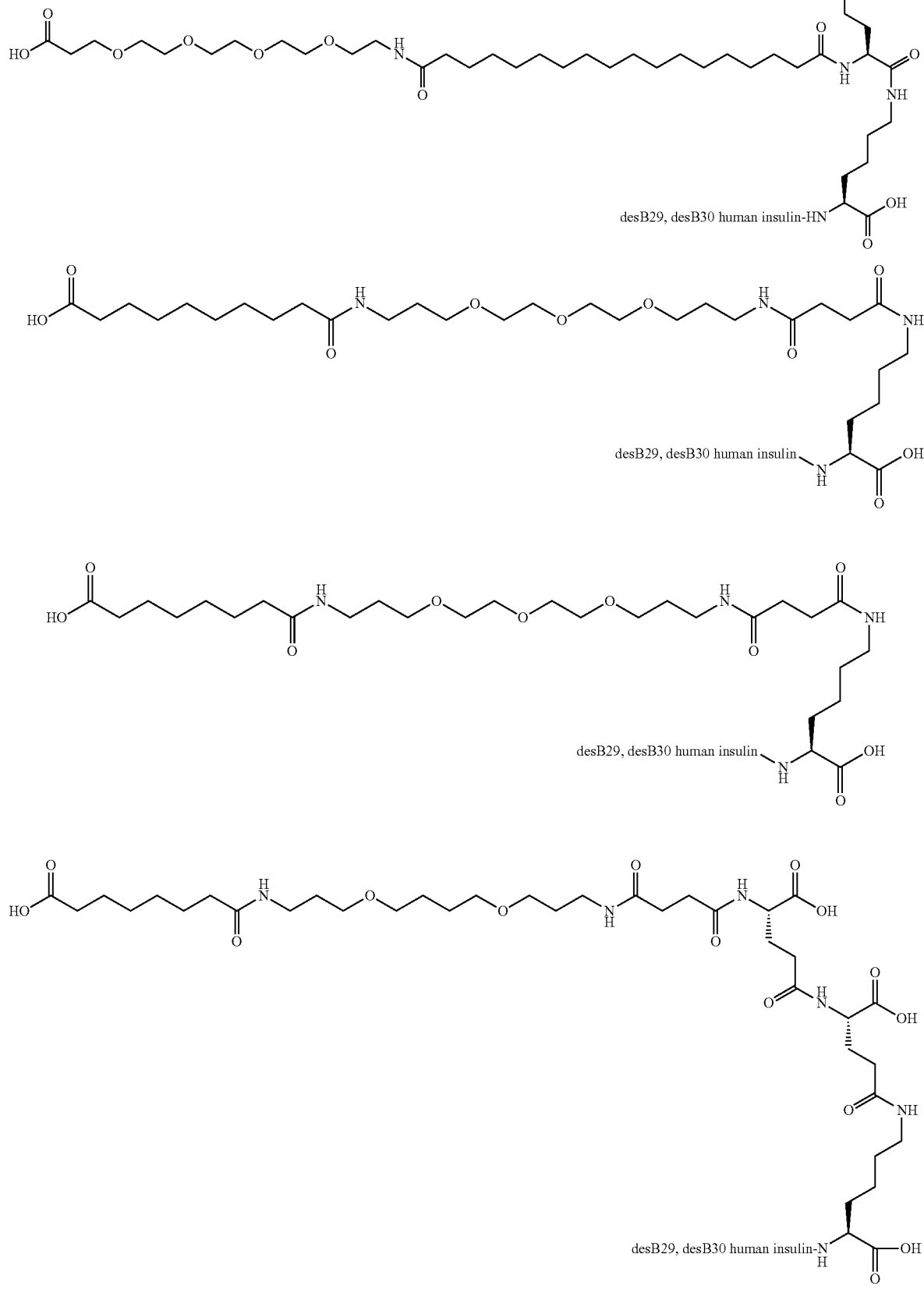

-continued

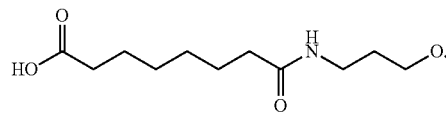

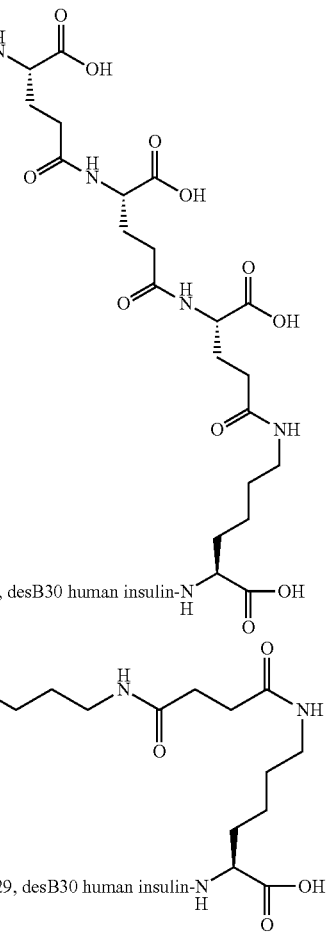

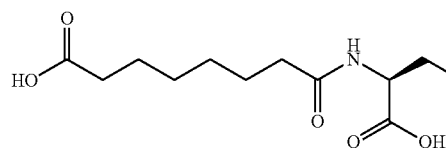

In a further aspect, the present invention relates to insulin derivatives which have an overall hydrophobicity which is essentially similar to that of human insulin.

In a further aspect, the insulin derivatives of the present invention have a hydrophobic index, k'rel, which is in the range from about 0.02 to about 10, from about 0.1 to about 5; from about 0.5 to about 5; from about 0.2 to about 2; from about 0.2 to about 1; from about 0.1 to about 2; or from about 0.5 to about 2.

According to one aspect of the present invention, the insulin derivatives will comprise a side chain of general formula (I) as defined above which have at least one free carboxylic acid group and according to a further aspect, the side chain will optionally hold one or more free carboxylic acid groups.

The hydrophobicity (hydrophobic index) of the insulin derivatives of the invention relative to human insulin, $k'_{rel}$, was measured on a LiChrosorb RP18 (5 μm, 250×4 mm) HPLC column by isocratic elution at 40° C. using mixtures of A) 0.1 M sodium phosphate buffer, pH 7.3, containing 10% acetonitrile, and B) 50% acetonitrile in water as eluents. The elution was monitored by following the UV absorption of the eluate at 214 nm. Void time, $t_0$, was found by injecting 0.1 mM sodium nitrate. Retention time for human insulin, $t_{human}$, was adjusted to at least $2 t_o$ by varying the ratio between the A and B solutions. $k'_{rel}=(t_{derivative}-t_0)/(t_{human}-t_0)$.

In another aspect, the invention relates to a pharmaceutical composition comprising an insulin derivative according to the invention which is soluble at physiological pH values.

In another aspect, the invention relates to a pharmaceutical composition comprising an insulin derivative according to the invention which is soluble at pH values in the interval from about 6.5 to about 8.5.

In another aspect, the invention relates to a pharmaceutical composition with a prolonged profile of action which comprises an insulin derivative according to the invention.

In another aspect, the invention relates to a pharmaceutical composition which is a solution containing from about 120 nmol/ml to about 2400 nmol/ml, from about 400 nmol/ml to about 2400 nmol/ml, from about 400 nmol/ml to about 1200 nmol/ml, from about 600 nmol/ml to about 2400 nmol/ml, or from about 600 nmol/ml to about 1200 nmol/ml of an insulin derivative according to the invention or of a mixture of the insulin derivative according to the invention with a rapid acting insulin analogue.

The starting product for the acylation, the parent insulin or insulin analogue or a precursor thereof can be produced by either well-know peptide synthesis or by well known recombinant production in suitable transformed microorganisms. Thus the insulin starting product can be produced by a method which comprises culturing a host cell containing a DNA sequence encoding the polypeptide and capable of expressing the polypeptide in a suitable nutrient medium under conditions permitting the expression of the peptide, after which the resulting peptide is recovered from the culture.

As an example desB30 human insulin can be produced from a human insulin precursor B(1-29)-Ala-Ala-Lys-A(1-

21) which is produced in yeast as disclosed in U.S. Pat. No. 4,916,212. This insulin precursor can then be converted into desB30 human insulin by ALP cleavage of the Ala-Ala-Lys peptide chain to give desB30 human insulin which can then be acylated to give the present insulintives.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The peptide produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gel filtration chromatography, affinity chromatography, or the like, dependent on the type of peptide in question.

The DNA sequence encoding the parent insulin may suitably be of genomic or cDNA origin, for instance obtained by preparing a genomic or cDNA library and screening for DNA sequences coding for all or part of the polypeptide by hybridisation using synthetic oligonucleotide probes in accordance with standard techniques (see, for example, Sambrook, J, Fritsch, E F and Maniatis, T, *Molecular Cloning: A Laboratory Manual*, Cold Spring Harbor Laboratory Press, New York, 1989). The DNA sequence encoding the parent insulin may also be prepared synthetically by established standard methods, e.g. the phosphoramidite method described by Beaucage and Caruthers, *Tetrahedron Letters* 22 (1981), 1859-1869, or the method described by Matthes et al., *EMBO Journal* 3 (1984), 801-805. The DNA sequence may also be prepared by polymerase chain reaction using specific primers, for instance as described in U.S. Pat. No. 4,683,202 or Saiki et al., *Science* 239 (1988), 487-491.

The DNA sequence may be inserted into any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the parent insulin is operably linked to additional segments required for transcription of the DNA, such as a promoter. The promoter may be any DNA sequence which shows transcriptional activity in the host cell of choice and may be derived from genes encoding proteins either homologous or heterologous to the host cell. Examples of suitable promoters for directing the transcription of the DNA encoding the parent insulin in a variety of host cells are well known in the art, cf. for instance Sambrook et al., supra.

The DNA sequence encoding the parent insulin may also, if necessary, be operably connected to a suitable terminator, polyadenylation signals, transcriptional enhancer sequences, and translational enhancer sequences. The recombinant vector of the invention may further comprise a DNA sequence enabling the vector to replicate in the host cell in question.

The vector may also comprise a selectable marker, e.g. a gene the product of which complements a defect in the host cell or one which confers resistance to a drug, e.g. ampicillin, kanamycin, tetracyclin, chloramphenicol, neomycin, hygromycin or methotrexate.

To direct a peptide of the present invention into the secretory pathway of the host cells, a secretory signal sequence (also known as a leader sequence, prepro sequence or pre sequence) may be provided in the recombinant vector. The secretory signal sequence is joined to the DNA sequence encoding the peptide in the correct reading frame. Secretory signal sequences are commonly positioned 5' to the DNA sequence encoding the peptide. The secretory signal sequence may be that normally associated with the peptide or may be from a gene encoding another secreted protein.

The procedures used to ligate the DNA sequences coding for the parent insulin, the promoter and optionally the terminator and/or secretory signal sequence, respectively, and to insert them into suitable vectors containing the information necessary for replication, are well known to persons skilled in the art (cf., for instance, Sambrook et al., supra).

The host cell into which the DNA sequence or the recombinant vector is introduced may be any cell which is capable of producing the present peptide and includes bacteria, yeast, fungi and higher eukaryotic cells. Examples of suitable host cells well known and used in the art are, without limitation, *E. coli, Saccharomyces cerevisiae*, or mammalian BHK or CHO cell lines.

The parent insulin molecule is then converted into the insulin derivatives of the invention by introducing of the relevant side chain in either the B1 position or in the chosen Lys position in the B-chain. The side chain can be introduced by any convenient method and many methods are disclosed in the prior art for acylation of an amino group. More details will appear from the following examples.

Pharmaceutical Compositions

The insulin derivatives of this invention of the claimed formula can, for example, be administered subcutaneously, orally, or pulmonary.

For subcutaneous administration, the compounds of the formula are formulated analogously with the formulation of known insulins. Furthermore, for subcutaneous administration, the compounds of the formula are administered analogously with the administration of known insulins and, generally, the physicians are familiar with this procedure.

The insulin derivatives of this invention may be administered by inhalation in a dose effective manner to increase circulating insulin levels and/or to lower circulating glucose levels. Such administration can be effective for treating disorders such as diabetes or hyperglycemia. Achieving effective doses of insulin requires administration of an inhaled dose of insulin derivative of this invention of more than about 0.5 µg/kg to about 50 µg/kg. A therapeutically effective amount can be determined by a knowledgeable practitioner, who will take into account factors including insulin level, blood glucose levels, the physical condition of the patient, the patient's pulmonary status, or the like.

According to the invention, insulin derivative of this invention may be delivered by inhalation to achieve prolonged duration of action. Administration by inhalation can result in pharmacokinetics comparable to subcutaneous administration of insulins. Different inhalation devices typically provide similar pharmacokinetics when similar particle sizes and similar levels of lung deposition are compared.

According to the invention, insulin derivative of this invention may be delivered by any of a variety of inhalation devices known in the art for administration of a therapeutic agent by inhalation. These devices include metered dose inhalers, nebulizers, dry powder generators, sprayers, and the like.

Preferably, insulin derivative of this invention is delivered by a dry powder inhaler or a sprayer. There are a several desirable features of an inhalation device for administering insulin derivative of this invention. For example, delivery by the inhalation device is advantageously reliable, reproducible, and accurate. The inhalation device should deliver small particles, for example, less than about 10 µm, for example about 1-5 µm, for good respirability. Some specific examples of commercially available inhalation devices suitable for the practice of this invention are Turbohaler™ (Astra), Rotahaler® (Glaxo), Diskus® (Glaxo), Spiros™ inhaler (Dura), devices marketed by Inhale Therapeutics, AERx™ (Aradigm), the Ultravent® nebulizer (Mallinckrodt), the Acorn II® nebulizer (Marquest Medical Products), the Ventolin® metered dose inhaler (Glaxo), the Spinhaler® powder inhaler (Fisons), or the like.

As those skilled in the art will recognize, the formulation of insulin derivative of this invention, the quantity of the formulation delivered, and the duration of administration of a single dose depend on the type of inhalation device employed. For some aerosol delivery systems, such as nebulizers, the frequency of administration and length of time for which the system is activated will depend mainly on the concentration of insulin conjugate in the aerosol. For example, shorter periods of administration can be used at higher concentrations of insulin conjugate in the nebulizer solution. Devices such as metered dose inhalers can produce higher aerosol concentrations, and can be operated for shorter periods to deliver the desired amount of insulin conjugate. Devices such as powder inhalers deliver active agent until a given charge of agent is expelled from the device. In this type of inhaler, the amount of insulin derivative of this invention in a given quantity of the powder determines the dose delivered in a single administration.

The particle size of insulin derivative of this invention in the formulation delivered by the inhalation device is critical with respect to the ability of insulin to make it into the lungs, and preferably into the lower airways or alveoli. Preferably, the insulin derivative of this invention is formulated so that at least about 10% of the insulin conjugate delivered is deposited in the lung, preferably about 10 to about 20%, or more. It is known that the maximum efficiency of pulmonary deposition for mouth breathing humans is obtained with particle sizes of about 2 μm to about 3 μm. When particle sizes are above about 5 μm pulmonary deposition decreases substantially. Particle sizes below about 1 μm cause pulmonary deposition to decrease, and it becomes difficult to deliver particles with sufficient mass to be therapeutically effective. Thus, particles of the insulin derivative delivered by inhalation have a particle size preferably less than about 10 μm, more preferably in the range of about 1 μm to about 5 μm. The formulation of the insulin derivative is selected to yield the desired particle size in the chosen inhalation device.

Advantageously for administration as a dry powder, an insulin derivative of this invention is prepared in a particulate form with a particle size of less than about 10 μm, preferably about 1 to about 5 μm. The preferred particle size is effective for delivery to the alveoli of the patient's lung. Preferably, the dry powder is largely composed of particles produced so that a majority of the particles have a size in the desired range. Advantageously, at least about 50% of the dry powder is made of particles having a diameter less than about 10 μm. Such formulations can be achieved by spray drying, milling, or critical point condensation of a solution containing insulin conjugate and other desired ingredients. Other methods also suitable for generating particles useful in the current invention are known in the art.

The particles are usually separated from a dry powder formulation in a container and then transported into the lung of a patient via a carrier air stream. Typically, in current dry powder inhalers, the force for breaking up the solid is provided solely by the patient's inhalation. In another type of inhaler, air flow generated by the patient's inhalation activates an impeller motor which deagglomerates the particles.

Formulations of insulin derivatives of this invention for administration from a dry powder inhaler typically include a finely divided dry powder containing the derivative, but the powder can also include a bulking agent, carrier, excipient, another additive, or the like. Additives can be included in a dry powder formulation of insulin conjugate, for example, to dilute the powder as required for delivery from the particular powder inhaler, to facilitate processing of the formulation, to provide advantageous powder properties to the formulation, to facilitate dispersion of the powder from the inhalation device, to stabilize the formulation (for example, antioxidants or buffers), to provide taste to the formulation, or the like. Advantageously, the additive does not adversely affect the patient's airways. The insulin derivative can be mixed with an additive at a molecular level or the solid formulation can include particles of the insulin conjugate mixed with or coated on particles of the additive. Typical additives include mono-, di-, and polysaccharides; sugar alcohols and other polyols, such as, for example, lactose, glucose, raffinose, melezitose, lactitol, maltitol, trehalose, sucrose, mannitol, starch, or combinations thereof; surfactants, such as sorbitols, diphosphatidyl choline, or lecithin; or the like. Typically an additive, such as a bulking agent, is present in an amount effective for a purpose described above, often at about 50% to about 90% by weight of the formulation. Additional agents known in the art for formulation of a protein such as insulin analogue protein can also be included in the formulation.

A spray including the insulin derivatives of this invention can be produced by forcing a suspension or solution of insulin conjugate through a nozzle under pressure. The nozzle size and configuration, the applied pressure, and the liquid feed rate can be chosen to achieve the desired output and particle size. An electrospray can be produced, for example, by an electric field in connection with a capillary or nozzle feed. Advantageously, particles of insulin conjugate delivered by a sprayer have a particle size less than about 10 μm, preferably in the range of about 1 μm to about 5 μm.

Formulations of insulin derivatives of this invention suitable for use with a sprayer will typically include the insulin derivative in an aqueous solution at a concentration of about 1 mg to about 20 mg of insulin conjugate per ml of solution. The formulation can include agents such as an excipient, a buffer, an isotonicity agent, a preservative, a surfactant, and, preferably, zinc. The formulation can also include an excipient or agent for stabilization of the insulin derivative, such as a buffer, a reducing agent, a bulk protein, or a carbohydrate. Bulk proteins useful in formulating insulin conjugates include albumin, protamine, or the like. Typical carbohydrates useful in formulating insulin conjugates include sucrose, mannitol, lactose, trehalose, glucose, or the like. The insulin derivative formulation can also include a surfactant, which can reduce or prevent surface-induced aggregation of the insulin conjugate caused by atomization of the solution in forming an aerosol. Various conventional surfactants can be employed, such as polyoxyethylene fatty acid esters and alcohols, and polyoxyethylene sorbitol fatty acid esters. Amounts will generally range between about 0.001 and about 4% by weight of the formulation.

Pharmaceutical compositions containing an insulin derivative according to the present invention may also be administered parenterally to patients in need of such a treatment. Parenteral administration may be performed by subcutaneous, intramuscular or intravenous injection by means of a syringe, optionally a pen-like syringe. Alternatively, parenteral administration can be performed by means of an infusion pump. Further options are to administer the insulin nasally or pulmonally, preferably in compositions, powders or liquids, specifically designed for the purpose.

Injectable compositions of the insulin derivatives of the invention can be prepared using the conventional techniques of the pharmaceutical industry which involve dissolving and mixing the ingredients as appropriate to give the desired end product. Thus, according to one procedure, an insulin derivative according to the invention is dissolved in an amount of water which is somewhat less than the final volume of the composition to be prepared. An isotonic agent, a preservative and a buffer is added as required and the pH value of the solution is adjusted—if necessary—using an acid, e.g. hydrochloric acid, or a base, e.g. aqueous sodium hydroxide as needed. Finally, the volume of the solution is adjusted with water to give the desired concentration of the ingredients.

In a further aspect of the invention the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative aspect of the invention.

In a further aspect of the invention the formulation further comprises a pharmaceutically acceptable preservative which may be selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thimerosal, bronopol, benzoic acid, imidurea, chlorohexidine, sodium dehydroacetate, chlorocresol, ethyl p-hydroxybenzoate, benzethonium chloride, chlorphenesine (3p-chlorophenoxypropane-1,2-diol) or mixtures thereof. In a further aspect of the invention the preservative is present in a concentration from 0.1 mg/ml to 20 mg/ml. In a further aspect of the invention the preservative is present in a concentration from 0.1 mg/ml to 5 mg/ml. In a further aspect of the invention the preservative is present in a concentration from 5 mg/ml to 10 mg/ml. In a further aspect of the invention the preservative is present in a concentration from 10 mg/ml to 20 mg/ml. Each one of these specific preservatives constitutes an alternative aspect of the invention. The use of a preservative in pharmaceutical compositions is well-known to the skilled person. For convenience reference is made to Remington: *The Science and Practice of Pharmacy*, 19$^{th}$ edition, 1995.

In a further aspect of the invention the formulation further comprises an isotonic agent which may be selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one aspect the sugar additive is sucrose. Sugar alcohol is defined as a C4-C8 hydrocarbon having at least one—OH group and includes, for example, mannitol, sorbitol, inositol, galactitol, dulcitol, xylitol, and arabitol. In one aspect the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. In one aspect, the sugar or sugar alcohol concentration is between about 1 mg/ml and about 150 mg/ml. In a further aspect of the invention the isotonic agent is present in a concentration from 1 mg/ml to 50 mg/ml. In a further aspect of the invention the isotonic agent is present in a concentration from 1 mg/ml to 7 mg/ml. In a further aspect of the invention the isotonic agent is present in a concentration from 8 mg/ml to 24 mg/ml. In a further aspect of the invention the isotonic agent is present in a concentration from 25 mg/ml to 50 mg/ml. Each one of these specific isotonic agents constitutes an alternative aspect of the invention. The use of an isotonic agent in pharmaceutical compositions is well-known to the skilled person. For convenience reference is made to Remington: *The Science and Practice of Pharmacy*, 19$^{th}$ edition, 1995.

Typical isotonic agents are sodium chloride, mannitol, dimethyl sulfone and glycerol and typical preservatives are phenol, m-cresol, methyl p-hydroxybenzoate and benzyl alcohol.

Examples of suitable buffers are sodium acetate, glycylglycine, HEPES (4-(2-hydroxyethyl)-1-piperazineethanesulfonic acid) and sodium phosphate.

A composition for nasal administration of an insulin derivative according to the present invention may, for example, be prepared as described in European Patent No. 272097 (to Novo Nordisk A/S).

Compositions containing insulin derivatives of this invention can be used in the treatment of states which are sensitive to insulin. Thus, they can be used in the treatment of type 1 diabetes, type 2 diabetes and hyperglycaemia for example as sometimes seen in seriously injured persons and persons who have undergone major surgery. The optimal dose level for any patient will depend on a variety of factors including the efficacy of the specific insulin derivative employed, the age, body weight, physical activity, and diet of the patient, on a possible combination with other drugs, and on the severity of the state to be treated. It is recommended that the daily dosage of the insulin derivative of this invention be determined for each individual patient by those skilled in the art in a similar way as for known insulin compositions.

Where expedient, the insulin derivatives of this invention may be used in mixture with other types of insulin, e.g. insulin analogues with a more rapid onset of action. Examples of such insulin analogues are described e.g. in the European patent applications having the publication Nos. EP 214826 (Novo Nordisk A/S), EP 375437 (Novo Nordisk A/S) and EP 383472 (Eli Lilly & Co.).

In a further aspect of the present invention the present compounds are administered in combination with one or more further active substances in any suitable ratios. Such further active agents may be selected from antidiabetic agents, antihyperlipidemic agents, antiobesity agents, antihypertensive agents and agents for the treatment of complications resulting from or associated with diabetes.

Suitable antidiabetic agents include insulin, GLP-1 (glucagon like peptide-1) derivatives such as those disclosed in WO 98/08871 (Novo Nordisk A/S), which is incorporated herein by reference, as well as orally active hypoglycemic agents.

Suitable orally active hypoglycemic agents preferably include imidazolines, sulfonyl-ureas, biguanides, meglitinides, oxadiazolidinediones, thiazolidinediones, insulin sensitizers, α-glucosidase inhibitors, agents acting on the ATP-dependent potassium channel of the pancreatic β-cells e.g. potassium channel openers such as those disclosed in WO 97/26265, WO 99/03861 and WO 00/37474 (Novo Nordisk A/S) which are incorporated herein by reference, potassium channel openers, such as ormitiglinide, potassium channel blockers such as nateglinide or BTS-67582, glucagon antagonists such as those disclosed in WO 99/01423 and WO 00/39088 (Novo Nordisk A/S and Agouron Pharmaceuticals, Inc.), all of which are incorporated herein by reference, GLP-1 agonists such as those disclosed in WO 00/42026 (Novo Nordisk A/S and Agouron Pharmaceuticals, Inc.), which are incorporated herein by reference, DPP-IV (dipeptidyl peptidase-IV) inhibitors, PTPase (protein tyrosine phosphatase) inhibitors, inhibitors of hepatic enzymes involved in stimulation of gluconeogenesis and/or glycogenolysis, glucose uptake modulators, GSK-3 (glycogen synthase kinase-3) inhibitors, compounds modifying the lipid metabolism such as antihyperlipidemic agents and antilipidemic agents, compounds lowering food intake, and PPAR (peroxisome proliferator-activated receptor) and RXR (retinoid X receptor) agonists such as ALRT-268, LG-1268 or LG-1069.

DEFINITIONS

With "desB30 insulin", "desB30 human insulin" is meant a natural insulin or an analogue thereof lacking the B30 amino acid residue. Similarly, "desB29desB30 insulin or "desB29desB30 human insulin" means a natural insulin or an analogue thereof lacking the B29 and B30 amino acid residues.

With "B(1-29)" is meant a natural insulin B chain or an analogue thereof lacking the B30 amino acid residue. "A(1-21)" means the natural insulin A chain or an analogue thereof.

With "B1", "A1" etc. is meant the amino acid residue in position 1 in the B chain of insulin (counted from the N-terminal end) and the amino acid residue in position 1 in the A chain of insulin (counted from the N-terminal end), respectively. The amino acid residue in a specific position may also be denoted as e.g. Phe$^{B1}$ which means that the amino acid residue in position B1 is a phenylalanine residue.

With "Insulin" as used herein is meant human insulin with disulfide bridges between Cys$^{A7}$ and Cys$^{B7}$ and between Cys$^{A20}$ and Cys$^{B19}$ and an internal disulfide bridge between Cys$^{A6}$ and Cys$^{A11}$, porcine insulin and bovine insulin.

By "insulin analogue" as used herein is meant a polypeptide which has a molecular structure which formally can be derived from the structure of a naturally occurring insulin, for example that of human insulin, by deleting and/or substituting at least one amino acid residue occurring in the natural insulin and/or by adding at least one amino acid residue. The added and/or substituted amino acid residues can either be codable amino acid residues or other naturally occurring amino acid residues or purely synthetic amino acid residues.

The insulin analogues may be such wherein position 28 of the B chain may be modified from the natural Pro residue to one of Asp, Lys, or Ile. In another aspect Lys at position B29 is modified to Pro. In one aspect B30 may be Lys and then B29 can be any codable amino acid except Cys, Met, Arg and Lys. Also, Asn at position A21 may be modified to Ala, Gln, Glu, Gly, His, Ile, Leu, Met, Ser, Thr, Trp, Tyr or Val, in particular to Gly, Ala, Ser, or Thr and preferably to Gly. Furthermore, Asn at position B3 may be modified to Lys or Asp. Further examples of insulin analogues are desB30 human insulin, desB30 human insulin analogues; insulin analogues wherein one or both of B1 and B2 have been deleted; insulin analogues wherein the A-chain and/or the B-chain have an N-terminal extension and insulin analogues wherein the A-chain and/or the B-chain have a C-terminal extension. Further insulin analogues are such wherein. Thus one or two Arg may be added to position B1. Also one or more of B26-B30 may have been deleted By "insulin derivative" as used herein is meant a naturally occurring insulin or an insulin analogue which has been chemically modified, e.g. by introducing a side chain in one or more positions of the insulin backbone or by oxidizing or reducing groups of the amino acid residues in the insulin or by converting a free carboxylic group to an ester group or acylating a free amino group or a hydroxy group.

The expression "a codable amino acid" or "a codable amino acid residue" is used to indicate an amino acid or amino acid residue which can be coded for by a triplet ("codon") of nucleotides.

α-Asp is the L-form of —HNCH(CO—)CH$_2$COOH.
β-Asp is the L-form of —HNCH(COOH)CH$_2$CO—.
α-Glu is the L-form of —HNCH(CO—)CH$_2$CH$_2$COOH.
γ-Glu is the L-form of —HNCH(COOH)CH$_2$CH$_2$CO—.

The expression "an amino acid residue having a carboxylic acid group in the side chain" designates amino acid residues like Asp, Glu and hGlu. The amino acids can be in either the L- or D-configuration. If nothing is specified it is understood that the amino acid residue is in the L configuration.

The expression "an amino acid residue having a neutral side chain" designates amino acid residues like Gly, Ala, Val, Leu, Ile, Phe, Pro, Ser, Thr, Cys, Met, Tyr, Asn and Gln.

When an insulin derivative according to the invention is stated to be "soluble at physiological pH values" it means that the insulin derivative can be used for preparing insulin compositions that are fully dissolved at physiological pH values. Such favourable solubility may either be due to the inherent properties of the insulin derivative alone or a result of a favourable interaction between the insulin derivative and one or more ingredients contained in the vehicle.

The following abbreviations have been used in the specification and examples:
Aad: Alpha-amino-adipic acid (homoglutamic acid)
Bzl=Bn: benzyl
CN: Alpha-cyano-4-hydroxycinnamic acid
DIEA: N,N-diisopropylethylamine
DMF: N,N-dimethylformamide
IDA: Iminodiacetic acid
Sar: Sarcosine (N-methyl-glycine)
tBu: tert-butyl
TSTU: O—(N-succinimidyl)-1,1,3,3-tetramethyluronium tetrafluoroborate
THF: Tetrahydrofuran
EtOAc: Ethyl acetate
DIPEA: N,N-Diisopropylethylamine
HOAt: 1-Hydroxy-7-azabenzotriazole
TEA: Triethyl amine
SA: Sinapic acid
Su: succinimidyl=2,5-dioxo-pyrrolidin-1-yl
TFA: Trifluoracetic acid
DCM: Dichloromethane
DMSO: Dimethyl sulphoxide
PEG: Polyethyleneglycol
PBG: Poly-1,4-butyleneglycol
PPG: Poly-1,3-propyleneglycol
TLC: Thin Layer Chromatography
RT: Room temperature With "fatty diacid" is meant a linear or branched dicarboxylic acids having at least 2 carbon atoms and being saturated or unsaturated. Non limiting examples of fatty diacids are succinic acid, hexanedioic acid, octanedioic acid, decanedioic acid, dodecanedioic acid, tetradecanedioic acid, hexadecanedioic acid and octadecanedioic acid.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

EXAMPLES

The following examples and general procedures refer to intermediate compounds and final products identified in the specification and in the synthesis schemes. The preparation of the compounds of the present invention is described in detail using the following examples, but the chemical reactions described are disclosed in terms of their general applicability to the preparation of compounds of the invention. Occasionally, the reaction may not be applicable as described to each compound included within the disclosed scope of the invention. The compounds for which this occurs will be readily recognised by those skilled in the art. In these cases the reactions can be successfully performed by conventional modifications known to those skilled in the art, that is, by appropriate protection of interfering groups, by changing to other conventional reagents, or by routine modification of reaction conditions. Alternatively, other reactions disclosed herein or otherwise conventional will be applicable to the preparation of the corresponding compounds of the invention. In all preparative methods, all starting materials are known or may easily be prepared from known starting materials. All temperatures are set forth in degrees Celsius and unless otherwise indicated, all parts and percentages are by weight when referring to yields and all parts are by volume when referring to solvents and eluents.

The compounds of the invention can be purified by employing one or more of the following procedures which are typical within the art. These procedures can—if needed—be modified with regard to gradients, pH, salts, concentrations, flow, columns and so forth. Depending on factors such as impurity profile, solubility of the insulins in question etcetera, these modifications can readily be recognised and made by a person skilled in the art.

After acidic HPLC or desalting, the compounds are isolated by lyophilisation of the pure fractions.

After neutral HPLC or anion exchange chromatography, the compounds are desalted, precipitated at isoelectrical pH, or purified by acidic HPLC.

Typical Purification Procedures:

The HPLC system is a Gilson system consisting of the following: Model 215 Liquid handler, Model 322-H2 Pump and a Model 155 UV Dector. Detection is typically at 210 nm and 280 nm.

The Äkta Purifier FPLC system (Amersham Biosciences) consists of the following: Model P-900 Pump, Model UV-900 UV detector, Model pH/C-900 pH and conductivity detector, Model Frac-950 Fraction collector. UV detection is typically at 214 nm, 254 nm and 276 nm.

Acidic HPLC:
Column: Macherey-Nagel SP 250/21 Nucleusil 300-7 C4
Flow: 8 ml/min
Buffer A: 0.1% TFA in acetonitrile
Buffer B: 0.1% TFA in water.
Gradient: 0.0-5.0 min: 10% A
5.00-30.0 min: 10% A to 90% A
30.0-35.0 min: 90% A
35.0-40.0 min: 100% A
Neutral HPLC:
Column: Phenomenex, Jupiter, C4 5 μm 250×10.00 mm, 300 Å
Flow: 6 ml/min
Buffer A: 5 mM TRIS, 7.5 mM $(NH_4)_2SO_4$, pH=7.3, 20% $CH_3CN$
Buffer B: 60% CH3CN, 40% water
Gradient: 0-5 min: 10% B
5-35 min: 10-60% B
35-39 min: 60% B
39-40 min: 70% B
40-43.5 min: 70% B
Anion Exchange Chromatography:
Column: RessourceQ, 1 ml
Flow: 6 ml/min
Buffer A: 0.09% $NH_4HCO_3$, 0.25% $NH_4OAc$, 42.5% ethanol pH 8.4
Buffer B: 0.09% $NH_4HCO_3$, 2.5% $NH_4OAc$, 42.5% ethanol pH 8.4
Gradient: 100% A to 100% B during 30 column volumes
Desalting:
Column: HiPrep 26/10
Flow: 10 ml/min, 6 column volumes
Buffer: 10 mM $NH_4HCO_3$
Analytical Procedures:
Method 1:
Two Waters 510 HPLC pumps
Waters 2487 Dual λ Absorbance detector
Buffer A: 0.1% TFA in acetonitrile.
Buffer B: 0.1% TFA in water.
Flow: 1.5 ml/min.
Gradient: 1-17 min: 25% B to 85% B, 17-22 min: 85% B, 22-23 min: 85% B to 25% B, 23-30 min 25% B, 30-31 min 25% B flow: 0.15 ml/min.
Column: C4 5μ 150×4.60 mm Phenomenex (Jupiter).
Detection: UV 214 nm.
Method 2:
Two Waters 510 HPLC pumps
Waters 2487 Dual λ Absorbance detector
Buffer A: 0.1% TFA, 10% $CH_3CN$, 89.9% water.
Buffer B: 0.1% TFA, 80% $CH_3CN$, 19.9% water.
Flow: 1.5 ml/min.
Gradient: 0-17 min: 20%-90% B, 17-21 min 90% B.
Column: C4 5μ 150×4.60 mm Phenomenex (Jupiter), kept at 40° C.

Detection: UV 214 nm.
Method 3: Two Waters 510 HPLC Pumps
Waters 486 Tunable Absorbance Detector
Waters 717 Autosampler
Column: C4 5μ 150×4_60 mm Phenomenex (Jupiter).
Injection: 20 μl.
Buffer A: 80% 0.0125 M Tris, 0.0187 M $(NH_4)_2SO_4$ pH=7, 20% $CH_3CN$.
Buffer B: 80% $CH_3CN$, 20% water.
Flow: 1.5 ml/min.
Gradient: 0 min 5% B→20 min 55% B→22 min 80% B→24 min 80% B→25 min 5% B 32 min 5% B.
Detection: UV 214 nm.
Method 4:
Two Waters 510 HPLC pumps
Waters 2487 Dual λ Absorbance Detector
Column: C4 5μ 150×4.60 mm Phenomenex (Jupiter).
Injection: 20 μl
Buffer A: 80% 0.0125 M Tris, 0.0187 M $(NH_4)_2SO_4$ pH=7, 20% $CH_3CN$
Buffer B: 80% $CH_3CN$, 20% water
Flow: 1.5 ml/min
Gradient: 0 min 10% B→20 min 50% B→22 min 60% B→23 min 10% B→30 min 10% B→31 min 10% B flow 0.15 min
Detection: 214 nm
Method 5:
Waters 2695 Separations Module
Waters 996 Photodiode Array Detector
Column: C4 5μ 150×4.60 mm Phenomenex (Jupiter).
Injection: 25 μl
Buffer A: 80% 0.01 M Tris, 0.015 M $(NH_4)_2SO_4$ pH=7.3; 20% $CH_3CN$
Buffer B: 20% water; 80% $CH_3CN$
Flow: 1.5 ml/min
Gradient: 1-20 min: 5-50% B, 20-22 min: 50-60% B, 22-23 min: 60-5% B, 23-30 min 0% B 30-31 min 0-5% B, flow: 0.15 ml/min.
Detection: 214 nm
Method 6:
Waters 2795 Separations Module
Waters 2996 Photodiode Array Detector
Waters Micromass ZQ 4000 Electrospray Mass Spectrometer
LC-method:
Column: Phenomenex, Jupiter 5μ C4 300 Å 50×4.60 mm
Buffer A: 0.1% TFA in water
Buffer B: $CH_3CN$
Flow: 1 ml/min
Gradient: 0-7.5 min: 10-90% B
7.5-8.5 min: 90-10% B
8.5-9.5 min 10% B
9.5-10.00 min 10% B, flow: 0.1 ml/min
MS method: Mw: 500-2000 ES+
Cone Voltage 60V
Scantime 1
Interscan delay: 0.1
Method 7:
Agilent 1100 Series
Column: GraceVydac Protein C4, 5 um 4.6×250 mm (Cat#214TP54)
Buffer A: 10 mM Tris, 15 mM $(NH_4)_2SO_4$, 20% CH3CN in water pH 7.3
Buffer B: 20% water in $CH_3CN$
Flow: 1.5 ml/min
Gradient: 1-20 min: 10% B to 50% B, 20-22 min: 50% B to 60% B, 22-23 min: 60% B to 10% B, 23-30 min 10% B 30-31 min 10% B, flow 0.15 ml/min.
Detection: 214 nm
Method 8: HPLC-MS
The following instrumentation is used:
Hewlett Packard series 1100 G1312A Bin Pump
Hewlett Packard series 1100 G13 15A DAD diode array detector
Sciex3000 triplequadropole mass spectrometer
Gilson 215 micro injector
Sedex55 evaporative light scattering detector
Pumps and detectors are controlled by MassChrom 1.1.1 software running on a Macintosh G3 computer. Gilson Unipoint Version 1.90 controls the auto-injector.
The HPLC pump is connected to two eluent reservoirs containing:
A: 0.01% TFA in water
B: 0.01% TFA in acetonitrile
The analysis is performed at room temperature by injecting an appropriate volume of the sample (preferably 10 μl) onto the column, which is eluted, with a gradient of acetonitrile. The eluate from the column passed through the UV detector to meet a flow splitter, which passed approximately 30 μl/min (1/50) through to the API Turbo ion-spray interface of API 3000 spectrometer. The remaining 1.48 ml/min (49/50) is passed through to the ELS detector.
The HPLC conditions, detector settings and mass spectrometer settings used are giving in the following table.

| | |
|---|---|
| Column | Waters X-Terra C18, 5μ, 50 mm × 3 mm id |
| Gradient | 5%-90% acetonitrile linearly during 7.5 min at 1.5 ml/min |
| Detection | 210 nm (analogue output from DAD) |
| MS | ionisation mode API Turbo ion-spray |
| ELS | Gain 8 and 40° C. |

Method 9: HPLC-MS
Hewlett Packard series 1100 G1312A Bin Pump
Hewlett Packard series 1100 Column compartment
Hewlett Packard series 1100 G1315A DAD diode array detector
Hewlett Packard series 1100 MSD
Sedere 75 Evaporative Light Scattering detector
The instrument was controlled by HP Chemstation software.
The HPLC pump was connected to two eluent reservoirs containing:
A: 0.01% TFA in water
B: 0.01% TFA in acetonitrile
The analysis is performed at 40° C. by injecting an appropriate volume of the sample (preferably 1 μl) onto the column which is eluted with a gradient of acetonitrile.
The HPLC conditions, detector settings and mass spectrometer settings used are giving in the following:
Column: Waters Xterra MS C-18×3 mm id 5 μm
Gradient: 5%-100% acetonitrile linear during 7.5 min at 1.5 ml/min
Detection: 210 nm (analogue output from DAD)
ELS (analogue output from ELS)
After the DAD the flow was divided yielding approx 1 ml/min to the ELS and 0.5 ml/min to the MS.
MALDI-TOF-MS spectra were recorded on a Bruker Autoflex II TOF/TOF operating in linear mode using a matrix of sinnapinic acid, a nitrogen laser and positive ion detection.
Accelerating voltage: 20 kV.

Example 1

Synthesis of N$^{\epsilon B29}$-(3-[2-{2-(2-[ω-carboxy-pentadecanoyl-γ-glutamyl-(2-amino-ethoxy)]-ethoxy)-ethoxy}-ethoxy]-propionyl) desB30 human insulin

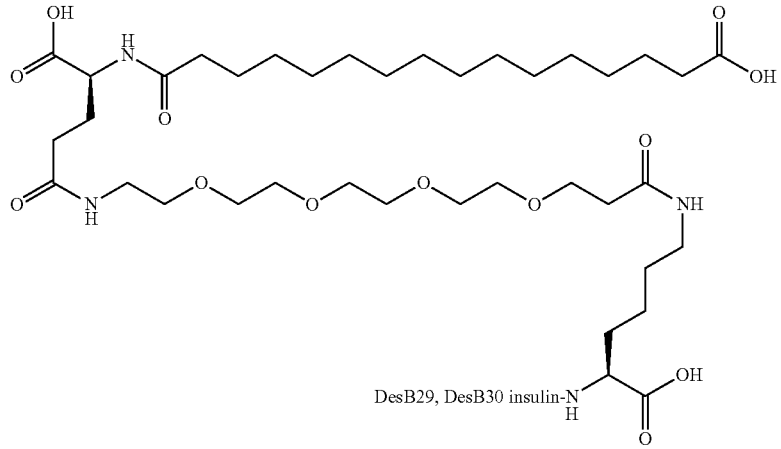

DesB30 human insulin (400 mg, 0.070 mmol) was dissolved in 100 mM Na$_2$CO$_3$ (5 ml, pH 10.2) at room temperature. Succinimidyl 3-[2-{2-(2-[ω-tert-butyl-carboxy-pentadecanoyl-γ-glutamyl-α-tert-butyl-(2-amino-ethoxy)]-ethoxy)-ethoxy}-ethoxy]-propionyl (72 mg, 0.084 mmol, prepared as described below), was dissolved in acetonitrile (5 ml) and subsequently added to the insulin solution. After 30 mins, 0.2 M methylamine (0.5 ml) was added. pH was adjusted by HCl to 5.5, and the isoelectric precipitate was collected by centrifugation and dried in vacuo to give 345 mg. The coupling yield was 64% (RP-HPLC, C4 column; Buffer A: 10% MeCN in 0.1% TFA-water, Buffer B: 80% MeCN in 0.1% TFA-water; gradient 20% to 90% B in 16 minutes). The protected product was dissolved in TFA (10 ml), left 30 mins, and evaporated in vacuo. The crude product was dissolved in water and lyophilized.

N$^{\epsilon B29}$-(3-[2-{2-(2-[ω-carboxy-pentadecanoyl-γ-glutamyl-(2-amino-ethoxy)]-ethoxy)-ethoxy}-ethoxy]-propionyl) desB30 human was purified by RP-HPLC on C4-column, buffer A: 20% EtOH+0.1% TFA, buffer B: 80% EtOH+ 0.1% TFA; gradient 15-60% B, followed by HPLC on C4-column, buffer A: 10 mM Tris+15 mM ammonium sulphate in 20% EtOH, pH 7.3, buffer B: 80% EtOH, gradient 15-60% B. The collected fractions were desalted on Sep-Pak with 70% acetonitrile+0.1% TFA, neutralized by addition of ammonia and freeze-dried. The unoptimized yield was 60 mg, 13%. The purity as evaluated by HPLC was >98%. MALDI-TOF-MS 6349, C$_{285}$H$_{432}$N$_{66}$O$_{86}$S$_6$ requires 6351.

Preparation of succinimidyl 3-[2-{2-(2-[ω-tert-butyl-carboxy-pentadecanoyl-γ-glutamyl-α-tert-butyl-(2-amino-ethoxy)]-ethoxy)-ethoxy}-ethoxy]-propionyl)

Hexadecadioic acid (40.0 g, 140 mmol) was suspended in toluene (250 ml) and the mixture was heated to reflux. N,N-dimethylformamide di-tert-butyl acetal (76.3 g, 375 mmol) was added drop-wise over 4 hours. The mixture was refluxed overnight. The solvent was removed in vacuo at 50° C., and the crude material was suspended in DCM/AcOEt (500 ml, 1:1) and stirred for 15 mins. The solids were collected by filtration and triturated with DCM (200 ml). The filtrated were evaporated in vacuo to give crude mono-tert-butyl hexadecanedioate, 30 grams. This material was suspended in DCM (50 ml), cooled with ice for 10 mins, and filtered. The solvent was removed in vacuo to leave 25 gram crude mono-tert-butyl hexadecanedioate, which was recrystallized from heptane (200 ml) to give mono-tert-butyl hexadecanedioate, 15.9 g (33%). Alternatively to recrystallization, the mono-ester can be purified by silica chromatography in AcOEt/heptane.

$^1$H-NMR (CDCl$_3$) δ: 2.35 (t, 2H), 2.20 (t, 2H), 1.65-1.55 (m, 4H), 1.44 (s, 9H), 1.34-1.20 (m, 20H).

The mono tert-butyl ester (2 g, 5.8 mmol) was dissolved in THF (20 ml) and treated with TSTU (2.1 g, 7.0 mmol) and DIEA (1.2 ml, 7.0 mmol) and stirred overnight. The mixture was filtered, and the filtrate was evaporated in vacuo. The residue was dissolved in AcOEt and washed twice with cold 0.1 M HCl and water. Drying over MgSO4 and evaporation in vacuo gave succinimidyl tert-butyl hexadecanedioate, 2.02 g (79%).

1H-NMR (CDCl3) δ: 2.84 (s, 4H), 2.60 (t, 2H), 2.20 (t, 2H), 1.74 (p, 2H), 1.56 (m, 2H), 1.44 (s, 9H), 1.40 (m, 2H), 1.30-1.20 (m, 18H).

Succinimidyl tert-butyl hexadecanedioate (1 g, 2.27 mmol) was dissolved in DMF (15 ml) and treated with L-Glu-OtBu (0.51 g, 2.5 mmol) and DIEA (0.58 ml, 3.41 mmol) and the mixture was stirred overnight. The solvent was evaporated in vacuo, and the crude product was dissolved in AcOEt, and washed twice with 0.2M HCl, with water and brine. Drying over MgSO$_4$ and evaporation in vacuo gave ω-tert-butyl carboxy-pentadecanoyl-L-glutamyl-α-tert-butyl ester, 1.2 g (100%).

1H-NMR (CDCl3) δ: 6.25 (d, 1H), 4.53 (m, 1H), 2.42 (m, 2H), 2.21 (m, 4H), 1.92 (m, 1H), 1.58 (m, 4H), 1.47 (s, 9H), 1.43 (s, 9H), 1.43-1.22 (m, 18H).

15-tert-butyl-carboxy-pentadecanoyl-L-glutamyl-α-tert-butyl ester (1.2 g, 2.27 mmol) was dissolved in THF (15 ml) and treated with TSTU (0.82 g, 2.72 mmol) and DIEA (0.47 ml, 2.72 mmol) and stirred overnight. The mixture was filtered, and the filtrate was evaporated in vacuo. The residue was dissolved in AcOEt and washed twice with cold 0.1 M HCl and water. Drying over MgSO$_4$ and evaporation in vacuo gave succinimidyl ω-tert-butyl-carboxy-pentadecanoyl-L-glutamyl-α-tert-butyl ester, 1.30 g (92%).

$^1$H-NMR (CDCl$_3$) δ: 6.17 (d, 1H), 4.60 (m, 1H), 2.84 (s, 4H), 2.72 (m, 1H), 2.64 (m, 1H), 2.32 (m, 1H), 2.20 (m, 4H), 2.08 (m, 1H), 1.6 (m, 4H), 1.47 (s, 9H), 1.43 (s, 9H), 1.33-1.21 (m, 20H).

Succinimidyl 15-tert-butyl-carboxy-pentadecanoyl-L-glutamyl-α-tert-butyl ester (109 mg, 0.17 mmol) was dissolved in DCM (2 ml) and treated with 3-(2-{2-[2-(2-amino-ethoxy)-ethoxy]-ethoxy}-ethoxy)-propionic acid (51 mg, 0.19 mmol, Quanta Biodesign, OH, USA) and DIEA (45 μL, 0.26 mmol). The mixture was stirred overnight and evaporated in vacuo. The residue was dissolved in AcOEt and washed twice with cold 0.2 M HCl, water and brine. Drying over MgSO$_4$ and evaporation in vacuo gave 3-[2-{2-(2-[ω-tert-butyl-carboxy-pentadecanoyl-γ-glutamyl-α-tert-butyl-(2-amino-ethoxy)]-ethoxy)-ethoxy}-ethoxy]-propionic acid), 119 mg (88%).

$^1$H-NMR (CDCl$_3$) δ: 7.01 (t, 1H), 6.58 (d, 1H), 4.42 (m, 1H), 3.76 (d, 2H), 3.62 (m, 16H), 3.55 (t, 2H), 3.42 (m, 1H), 2.58 (t, 2H), 2.28 (m, 2H), 2.17 (m, 2H), 2.11 (m, 1H), 1.94 (m, 1H), 1.57 (m, 4H), 1.43 (s, 9H), 1.42 (s, 9H), 1.22 (m, 20H).

3-[2-{2-(2-[ω-tert-Butyl-carboxy-pentadecanoyl-γ-glutamyl-α-tert-butyl-(2-amino-ethoxy)]-ethoxy)-ethoxy}-propionic acid) (119 mg, 0.15 mmol) was dissolved in THF (2 ml) and treated with TSTU (55 mg, 018 mmol) and DIEA (31 μL, 0.18 mmol) and stirred overnight. The mixture was filtered, and the filtrate was evaporated in vacuo. The residue was dissolved in AcOEt and washed twice with cold 0.1 M HCl and water. Drying over MgSO$_4$ and evaporation in vacuo gave succinimidyl 3-[2-{2-(2-[ω-tert-butyl-carboxy-pentadecanoyl-γ-glutamyl-α-tert-butyl-(2-amino-ethoxy)]-ethoxy)-ethoxy}-ethoxy]-propionyl), 123 mg (92%).

$^1$H-NMR (CDCl$_3$) δ: 6.64 (t, 1H), 6.54 (d, 1H), 4.35 (m, 1H), 3.80 (d, 2H), 3.59 (m, 16H), 3.51 (t, 2H), 3.39 (m, 1H), 2.85 (t, 2H), 2.79 (s, 4H), 2.22 (m, 2H), 2.15 (m, 2H), 2.08 (m, 1H), 1.90 (m, 1H), 1.55 (m, 4H), 1.41 (s, 9H), 1.39 (s, 9H), 1.20 (m, 20H).

Example 2

Synthesis of N$^{εB29}$-(3-[2-{2-(2-[ω-carboxy-heptadecanoyl-γ-glutamyl-(2-amino-ethoxy)]-ethoxy)-ethoxy}-ethoxy]-propionyl) desB30 human insulin

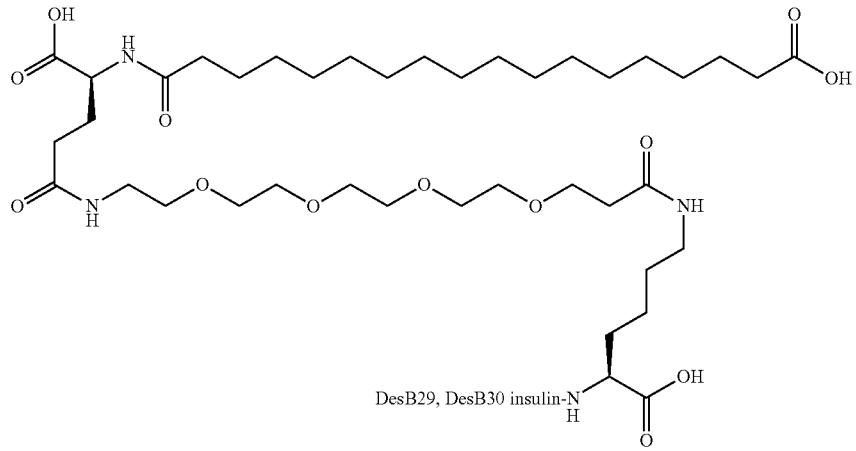

This compound was prepared in analogy with example 1 via reaction of L-GluOtBu with tert-butyl succinimidyl octadecanedioate followed by activation with TSTU, activation with TSTU, reaction with 3-(2-{2-[2-(2-Amino-ethoxy)-ethoxy]-ethoxy}-ethoxy)-propionic acid activation with TSTU, coupling with DesB30 human insulin and deprotection by TFA.

MALDI-TOF-MS 6380, calculated 6379.

Example 3

Synthesis of N$^{εB29}$-{3-[2-(2-{2-[2-(15-carboxy-pentadecanoylamino)-ethoxy]-ethoxy}-ethoxy)-ethoxy]-propionyl-γ-glutamyl desB30 human insulin

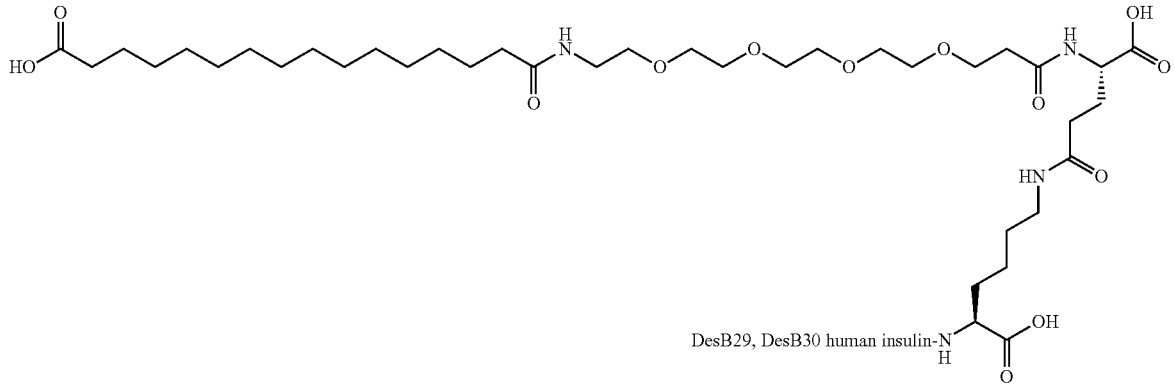

Step 1: ω-[2-(2-{2-[2-(2-Carboxy-ethoxy)-ethoxy]-ethoxy}-ethoxy)-ethylcarbamoyl]-pentadecanoic acid tert-butyl ester

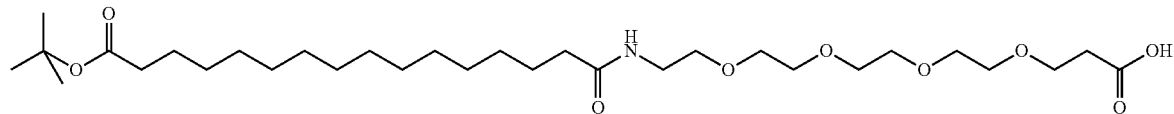 [SMILES: CC(C)(C)OC(=O)CCCCCCCCCCCCCCC(=O)NCCOCCOCCOCCOCCC(=O)O]

Hexadecanedioic acid tert-butyl ester 2,5-dioxo pyrrolidin-1-yl ester (0.12 g, 0.283 mmol) was dissolved in DMF (2.5 ml), 3-(2-{2-[2-(2-amino-ethoxy)-ethoxy]-ethoxy}-ethoxy)-propionic acid (75 mg, 0.283 mmol) was added and the mixture was stirred at rt for 16 h. The reaction mixture was combined with another reaction mixture performed on a 0.038 mmol scale. AcOEt (25 ml) was added an the solution was washed with acidified water (15 ml+300 μl of 0.1 N HCl) and water (3×15 ml), dried over MgSO$_4$ and concentrated under vacuum, adding some DCM and concentrating again twice, thus yielding a white greasy residue (0.15 g, 79%)

HPLC-MS m/z: 590 (M+1), Rt=5.24 min.
1H-NMR (CDCl$_3$, 400 MHz) δ 6.48 (br, 1H), 3.79 (t, 2H), 3.6-3.7 (m, 14H), 3.47 (m, 2H), 2.60 (t, 2H), 2.17-2.22 (m, 4H), 1.57-1.64 (m, 4H), 1.44 (s, 9H), 1.2-1.3 (m, 20H).

Step 2: 2-{3-[2-(2-{2-[2-(ω-tert-Butoxycarbonylpentadecanoylamino)ethoxy]-ethoxy}ethoxy)ethoxy]propionylamino}pentanedioic acid 5-benzyl ester 1-tert-butyl ester

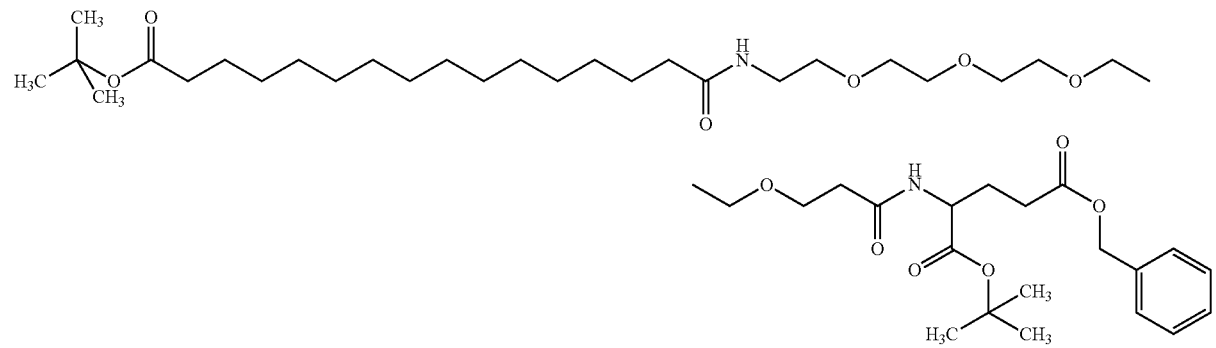

Hexadecanoic acid tert-butyl ester 0.15 g, 0.254 mmol) was dissolved in DMF (2.5 ml) and HOBt (48 mg, 0.356 mmol) and EDAC (63 mg, 0.331 mmol) were added. The solution was stirred at rt for 30 min and H-Glu-(OBzl)-OtBu (117 mg, 0.356 mmol) was added. The reaction was stirred at rt for 16 h, and AcOEt (25 ml) was added. The solution was washed with water (10 ml), 0.2 N HCl (3×10 ml), 1:1 Sat. NaCl/water (3×10 ml), dried over MgSO$_4$ and concentrated to yield an oil (0.24 g). The product was purified by flash chromatography (silica, 95:5 DCM/methanol) to yield an oil 0.2 g.

HPLC-MS (method 9): m/z: 866 (M+1), R$_f$=6.99-7.09 min
1H-NMR (CDCl$_3$, 400 MHz) δ 7.34-7.38 (m, 5H), 6.83 (d, 1H), 6.10 (br, 1H), 5.11 (s, 2H), 4.50-4.55 (m, 1H), 3.71-3.75 (m, 2H), 3.60-3.65 (m, 12H), 3.55 (t, 2H), 3.36-3.42 (m, 2H), 2.36-2.51 (m, 4H), 2.14-2.24 (m, 5H), 1.93-2.00 (m, 1H), 1.57-1.63 (m, 4H), 1.46 (s, 9H), 1.44 (s, 9H), 1.2-1.3 (m, 20H).

Step 3: 2-{3-[2-(2-{2-[2-(ω-tert-butoxycarbonylpentadecanoylamino)ethoxy]ethoxy}ethoxy)ethoxy]-propionylamino}pentanedioic acid 1-tert-butyl ester

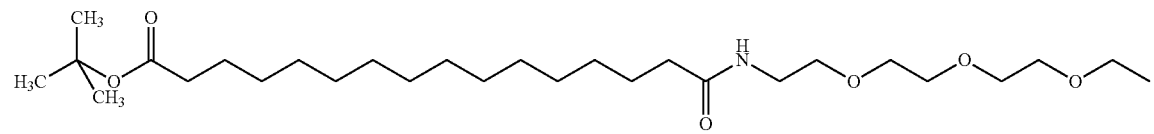

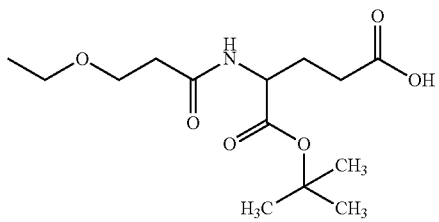

2-{3-[2-(2-{2-[2-(ω-tert-Butoxycarbonylpentadecanoylamino)ethoxy]-ethoxy}ethoxy)ethoxy]propionylamino}pentanedioic acid 5-benzyl ester 1-tert-butyl ester (0.2 g, 0.23 mmol) was dissolved in THF. The flask was filled with N₂, and palladium (0.3 g, 10% on carbon, 50% water) was added, and the flask was equipped with a balloon filled with H₂. The mixture was stirred for 16 h at rt, and filtered through celite, washing with THF. The filtrate was concentrated to yield an oil (0.16 g, 89%).

HPLC-MS (method 9 m/z: 775 (M+1), Rt=5.46 min.

Step 4: 2-{3-[2-(2-{2-[2-(ω-tert-Butoxycarbonyl-pentadecanoylamino)ethoxy]-ethoxy}ethoxy)ethoxy]-propionylamino}pentanedioic acid 5-tert-butyl ester 1-(2,5-dioxopyrrolidin-1-yl) ester

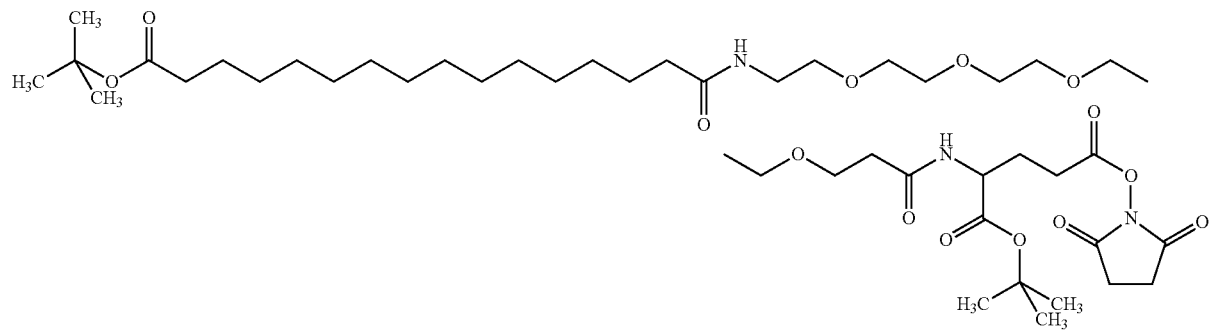

2-{3-[2-(2-{2-[2-(ω-tert-Butoxycarbonyl-pentadecanoylamino) ethoxy]-ethoxy}ethoxy)ethoxy]-propionylamino}pentanedioic acid 1-tert-butyl ester (0.16 g, 0.21 mmol) was dissolved in DMF (2 ml) and THF (4 ml) and DIEA (42 µl, 0.25 mmol) was added. The solution was cooled to 0° C., and TSTU (74 mg, 0.21 mmol) was added. The reaction was stirred over night at rt. the solvent was removed under vacuum and AcOEt (25 ml) was added. The mixture was washed with 0.2 N HCl (3×10 ml), sat NaHCO₃ (3×10 ml), dried over MgSO₄ and concentrated under vacuum to yield an oil (0.16 g). The product was purified by flash chromatography (silica, 95:5 DCM/methanol) to yield an oil (0.11 g, 61%).

HPLC-MS (method 9) m/z: 872 (M+1), Rt=5.67 min.

Step 5: N$^{\epsilon B29}$-{3-[2-(2-{2-[2-(ω-carboxy-pentadecanoylamino)-ethoxy]-ethoxy}-ethoxy)-ethoxy]-propionyl-γ-glutamyl desB30 human insulin

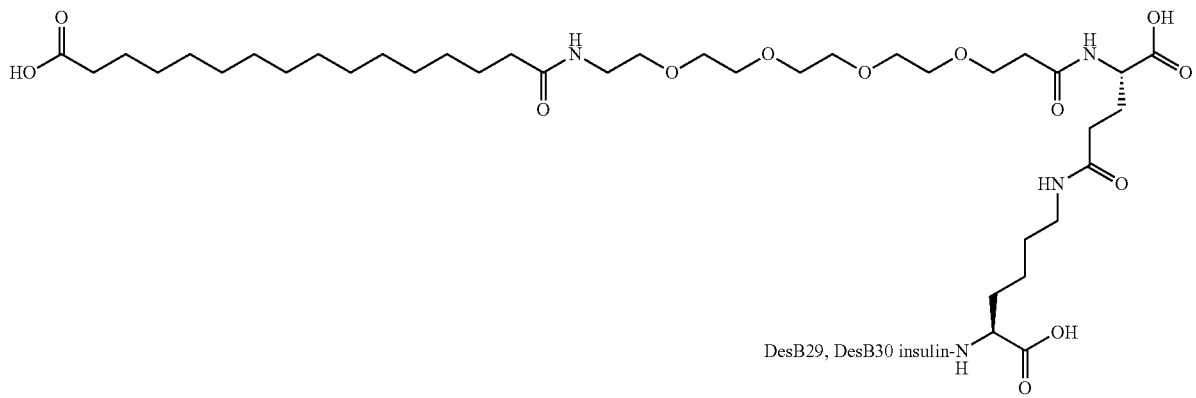

2-{3-[2-(2-{2-[2-(ω-tert-Butoxycarbonyl-pentadecanoylamino)ethoxy]-ethoxy}ethoxy)ethoxy]-propionylamino}pentanedioic acid α-tert-butyl ester 1-(2,5-dioxopyrrolidin-1-yl) ester was coupled to desB30 insulin in similar fashion as described in Example 1 The intermediate product was purified by preparative HPLC ($C_{18}$-5 cm dia.) before treating with TFA. The final product was purified by preparative HPLC ($C_4$, 2 cm dia.) then ($C_4$, 1 cm dia.) (20-60% acetonitrile).

MALDI-TOF-MS: 6355, Calculated: 6351

Example 4

Synthesis of $N^{\epsilon B29}$-(ω-[2-(2-{2-[2-(2-carboxy-ethoxy)-ethoxy]-ethoxy}-ethoxy)-ethylcarbamoyl]-heptadecanoyl-α-glutamyl) desB30 human insulin

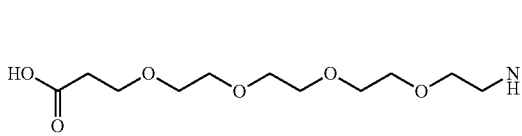
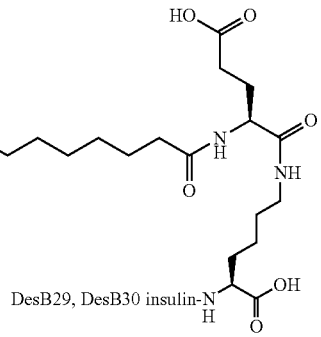

This compound was prepared in analogy with example 1 via reaction of $H_2N(CH_2CH_2O)_4$—$CH_2CH_2COOtBu$ (Quanta Biodesign, OH, USA) with mono-succinimidyl octadecanedioate followed by activation with TSTU, reaction with L-Glu(OtBu), activation with TSTU, coupling with DesB30 human insulin and deprotection by TFA.

LCMS 6380, method 6, calculated 6379.

Example 5

Synthesis of $N^{\epsilon B29}$-(ω-[2-(2-{2-[2-(2-carboxy-ethoxy)-ethoxy]-ethoxy}-ethoxy)-ethylcarbamoyl]-heptadecanoyl-γ-glutamyl) desB30 human insulin

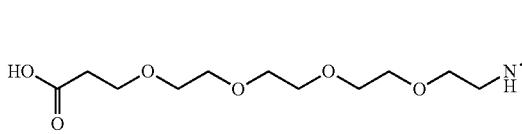
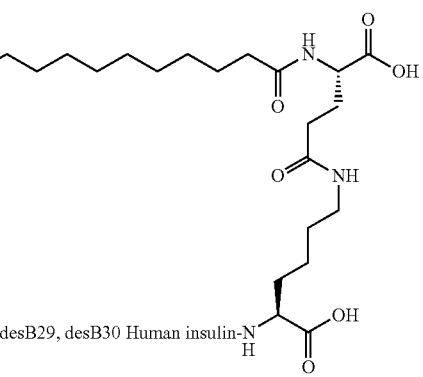

This compound was prepared in analogy with example 1 via reaction of $H_2N(CH_2CH_2O)_4$—$CH_2CH_2COOtBu$ (Quanta Biodesign, OH, USA) with mono-succinimidyl octadecanedioate followed by activation with TSTU, reaction with L-Glu-OtBu, activation with TSTU, coupling with DesB30 human insulin and deprotection by TFA.

LCMS 6378.4, method 6, calculated 6379.4.

Example 6

Synthesis of N$^{\epsilon B29}$-3-[2-(2-{2-[2-(ω-carboxy-heptadecanoylamino)-ethoxy]-ethoxy}-ethoxy)-ethoxy]-propionyl-γ-glutamyl desB30 human insulin

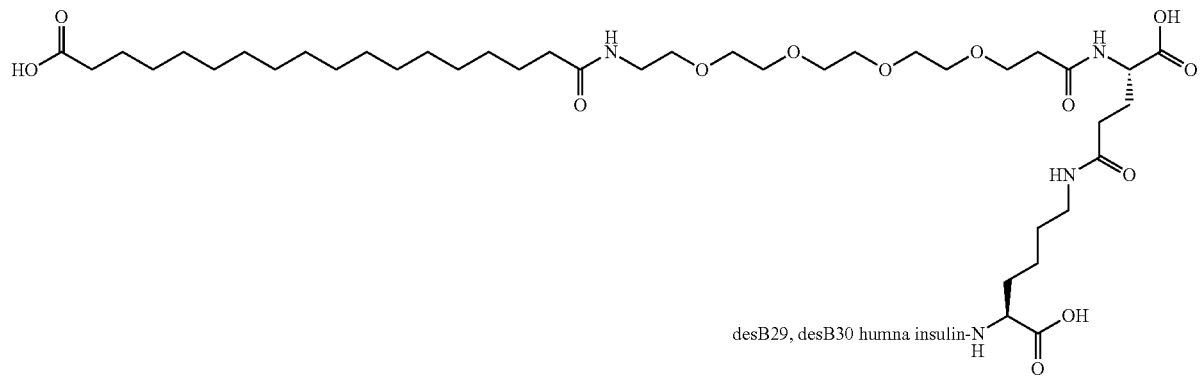

The compound was prepared in the same manner as with N$^{\epsilon B29}$-3-[2-(2-{2-[2-(ω-carboxy-pentadecanoylamino)-ethoxy]-ethoxy}-ethoxy)-ethoxy]-propionyl-γ-glutamyl desB30 insulin using octadecanedioic acid tert-butyl ester 2,5-dioxo-pyrrolidin-1-yl ester as the starting material.

Step 1: ω-[2-(2-{2-[2-(2-carboxy-ethoxy)-ethoxy]-ethoxy}-ethoxy)-ethylcarbamoyl]-heptadecanoic acid tert-butyl ester

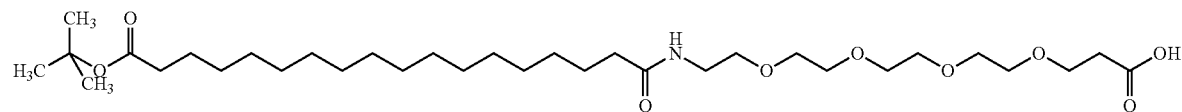 [SMILES: CC(C)(C)OC(=O)CCCCCCCCCCCCCCCCC(=O)NCCOCCOCCOCCOCCC(=O)O]

HPLC-MS (method 9) m/z: 618 (M+1), Rt=5.92 min.
1H-NMR (CDCl$_3$, 300 MHz) δ 6.46 (br, 1H), 3.79 (t, 2H), 3.61-3.69 (m, 14H), 3.44-3.49 (m, 2H), 2.60 (t, 2H), 2.16-2.22 (m, 4H), 1.51-1.68 (m, 4H), 1.44 (s, 9H), 1.19-1.36 (m, 24H).

Step 2: 2-{3-[2-(2-{2-[2-(17-tert-Butocycarbonyl-heptadecanoylamino)ethoxy]-ethoxy}ethoxy)ethoxy]-propionylamino}pentanedioic acid 5-benzyl ester 1-tert-butyl ester

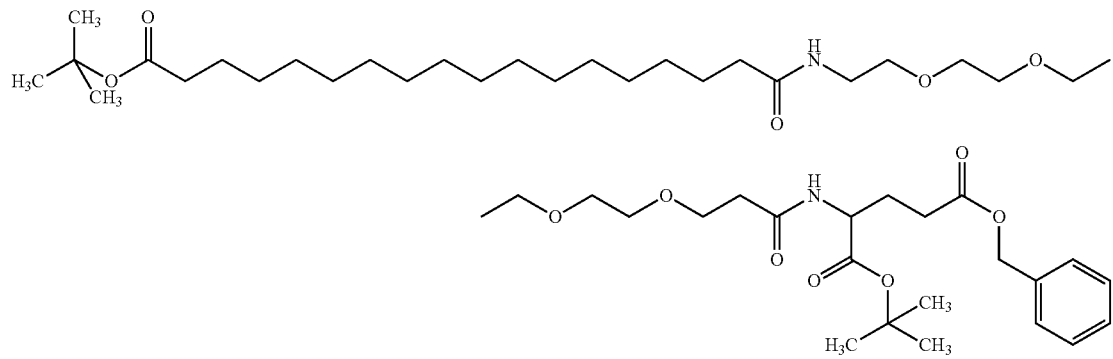

HPLC-MS (method 9) m/z: 894 (M+1), Rt=7.82-7.89 min.

1H-NMR (CDCl₃, 300 MHz) δ 7.29-7.42 (m, 5H), 6.83 (d, 1H), 6.13 (br, 1H), 5.11 (s, 2H), 4.46-4.59 (m, 1H), 3.68-3.81 (m, 2H), 3.57-3.68 (m, 12H), 3.55 (t, 2H), 3.39-3.49 (m, 2H), 2.32-2.55 (m, 4H), 2.12-2.28 (m, 5H), 1.86-2.07 (m, 1H), 1.51-1.68 (m, 4H), 1.46 (s, 9H), 1.44 (s, 9H), 1.17-1.36 (m, 24H).

Step 3: 2-{3-[2-(2-{2-[2-(17-tert-Butoxycarbonyl-heptadecanoylamino)ethoxy]-ethoxy}ethoxy)ethoxy]propionylamino}pentanedioic acid 1-tert-butyl ester

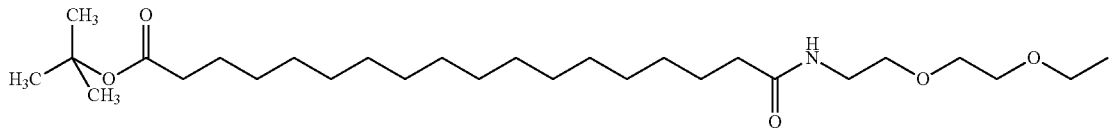

HPLC-MS (method 9) m/z: 804 (M+1), Rt=5.81 min.

Step 4: 2-{3-[2-(2-{2-[2-(ω-tert-Butoxycarbonyl-heptadecanoylamino)ethoxy]-ethoxy}ethoxy)ethoxy]propionylamino}pentanedioic acid 5-tert-butyl ester 1-(2,5-dioxo-pyrrolidin-1-yl) ester HPLC-MS (method 9) m/z: 901 (M+1), Rt=6.00 min.
1H-NMR (CDCl₃, 300 MHz) δ 6.94 (d, 1H), 6.15 (br, 1H), 4.55-4.62 (m, 1H), 3.71-3.79 (m, 2H), 3.59-3.71 (m, 12H), 3.55 (t, 2H), 3.42-3.47 (m, 2H), 2.84 (s, 4H), 2.58-2.79 (m, 2H), 2.52 (t, 2H), 2.24-2.41 (m, 1H), 2.13-2.24 (m, 4H), 2.04-2.10 (m, 1H), 1.51-1.70 (m, 4H), 1.48 (s, 9H), 1.44 (s, 9H) 1.19-1.37 (m, 24H).

Step 5: N^{εB29}-(3-[2-(2-{2-[2-(17-carboxy-heptadecanoylamino)-ethoxy]-ethoxy}-ethoxy)-ethoxy]-propionyl gamma-glutamyl desB30 human insulin The final product was purified by HPLC (C₁₈-5 cm dia.).
HPLC-MS (method 9) m/z: 1596.4 (M+4/4), Calculated 6379, Rt=4.05 min

Example 7

Synthesis of $N^{\epsilon B29}$-(3-(3-{2-[2-(3-[7-carboxyheptanoylamino]propoxy)ethoxy]-ethoxy}propylcarbamoyl)propionyl) desB30 human insulin

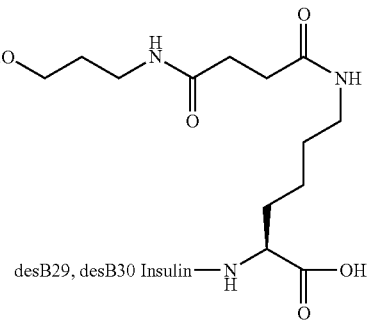

This compound was prepared using the same synthesis steps as reported for the synthesis of example 1.

Step 1. N-(3-{2-[2-(3-tert-Butoxycarbonylaminopropoxy)ethoxy]ethoxy}propyl)succinamic acid

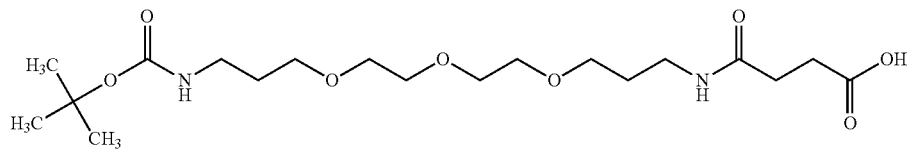 [SMILES: CC(C)(C)OC(=O)NCCCOCCOCCOCCCNC(=O)CCC(=O)O]

preparation from 1-(tert-butoxycarbonylamino)-4,7,10-trioxa-13-tridecanamine (5 g) and succinic anhydride (1.98) gave 7 g crude product. LCMS (Method 6): Rt 3.34 min; m/z (M+1) 421 Calcd: 421

Step 2. 7-[3-(2-{2-[3-(3-Carboxypropionylamino)-propoxy]-ethoxy}-ethoxy)-propylcarbamoyl]-heptanoic acid tert-butyl ester

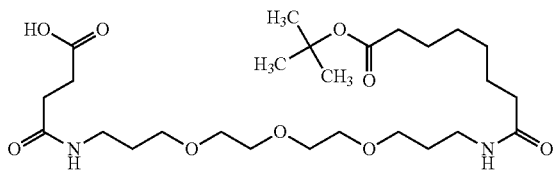 [SMILES: CC(C)(C)OC(=O)CCCCCCC(=O)NCCCOCCOCCOCCCNC(=O)CCC(=O)O]

This compound was prepared by deprotection of N-(3-{2-[2-(3-tert-butoxycarbonylaminopropoxy)-ethoxy]ethoxy}propyl)succinamic acid (1.56 mmol) by means of TFA, followed by reaction with octanedioic acid tert-butyl ester 2,5-dioxo-pyrrolidin-1-yl ester (1.56 mmol). as described in example 8 step 3.

The crude product was purified on Gilson using acidic HPLC on a C18 column (Jones, Kromasil RP18 5 μm 15×225 mm).

Gradient: 0.0-4.0 min 20% A; 4.0-11.0 min 20-90% A; 11-16 min 90% A.

The product was collected in fractions from 15.0-17.0 min. The combined fractions were evaporated yielding the wanted product (0.78 g)

LCMS (Method 9): Rt 4.03 min; m/z (M+1) 533, Calcd.: 533.

Step 3. 7-{3-[2-(2-{3-[3-(2,5-Dioxopyrrolidin-1-yloxycarbonyl)-propionylamino]-propoxy}-ethoxy)-ethoxy]-propylcarbamoyl}-heptanoic acid tert-butyl ester

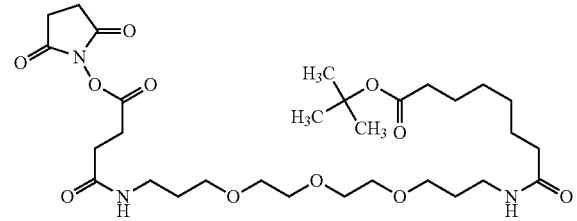 [SMILES: CC(C)(C)OC(=O)CCCCCCC(=O)NCCCOCCOCCOCCCNC(=O)CCC(=O)ON1C(=O)CCC1=O]

7-[3-(2-{2-[3-(3-Carboxypropionylamino)-propoxy]-ethoxy}-ethoxy)-propylcarbamoyl]-heptanoic acid tert-butyl ester (0.78 g, 1.46 mmol) was activated by means of TSTU as described in example 8 step 4. Crude yield 360 mg, LCMS Method 6: Rt 4.40 min; m/z (M+1) 630; Calcd.: 630. The compound was used without further purification.

Step 4. $N^{\epsilon B29}$-(3-(3-{2-[2-(3-[7-carboxyheptanoylamino]propoxy)ethoxy]-ethoxy}propylcarbamoyl)propionyl-γ-glutamyl) desB30 human insulin

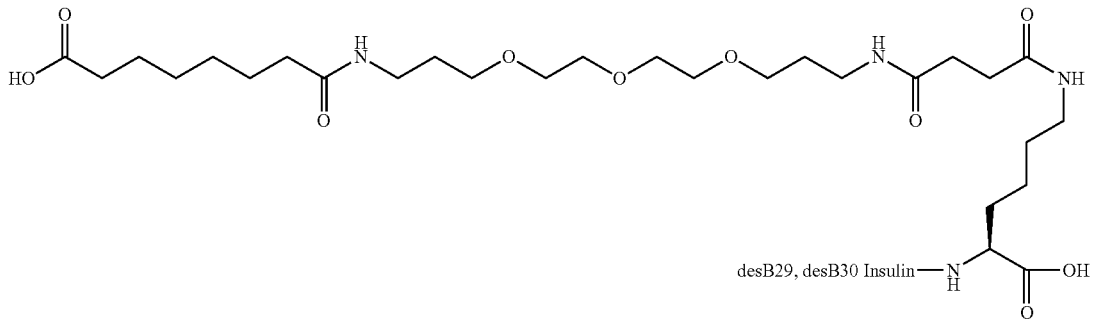

Example 8

Preparation following step 6 in example 8 resulted in 0.78 g of the target product after purification on Gilson using acidic HPLC on a C18 column (Jones, Kromasil RP18 5 μm 15×225 mm). Gradient: 0.0-1.0 min: 30% CH3CN, 1.00-15.0 min: 30-50% CH3CN, 15.0-20.0 min: 50% CH3CN Flow: 10 ml/min. Rt=14.5-16.0 min.
MALDI-TOF-MS (matrix SA): m/z 6167; calc. 6165.
HPLC (method 5); Rt 3.973 min.

Synthesis of $N^{\epsilon B29}$-(3-(3-{4-[3-(7-Carboxyheptanoylamino)propoxy]butoxy}propylcarbamoyl)-propionyl-γ-glutamyl) desB30 human insulin

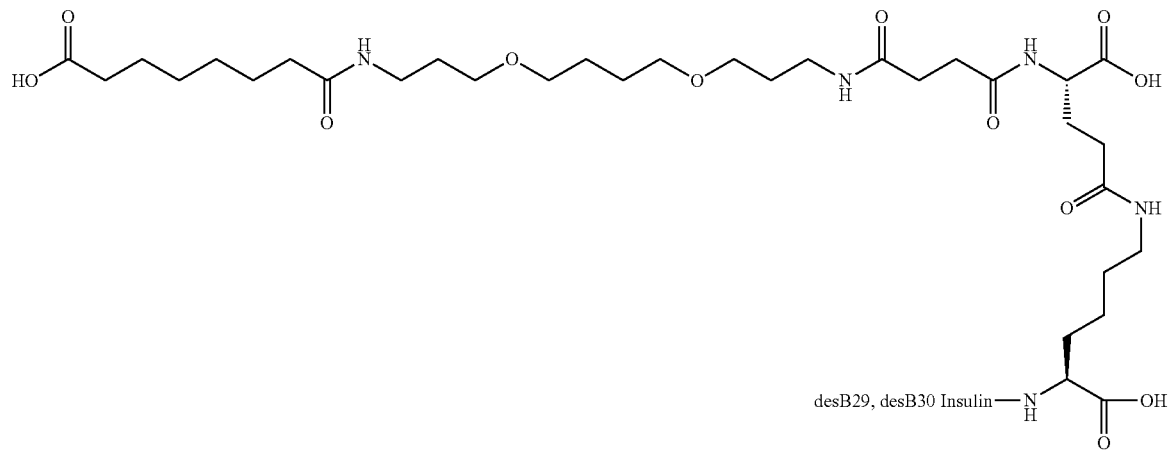

Step 1: N-{3-[4-(3-tert-Butoxycarbonylaminopropoxy)-butoxy]-propyl}succinamic acid

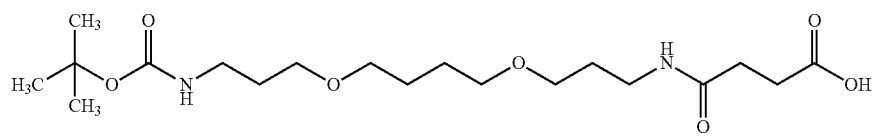 [SMILES: CC(C)(C)OC(=O)NCCCOCCCCOCCCNC(=O)CCC(=O)O]

1-(tert-Butoxycarbonylamino)-4,9-dioxa-12-dodecanamine (5.0 g, 16.45 mmol) was dissolved in THF (30 mL), succinic anhydride (1.81 g, 18.1 mmol) in acetonitrile (10 mL) was added and the mixture was heated to 60 C for 4 h, and subsequently stirred at RT overnight.

The mixture was evaporated to dryness and EtAc (50 mL) was added.

The EtAc phase was washed with HCl (0.1 M) 3 times, dried with MgSO4 and subsequently the organic phase was evaporated to dryness which gave 5.86 g (88%) of a thick oil.
LCMS (Method 6): Rt 2.86 min; m/z (M+1) 405. Calcd: 405.
This product was used without further purification.

Step 2. Octanedioic acid tert-butyl ester 2,5-dioxo-pyrrolidin-1-yl ester

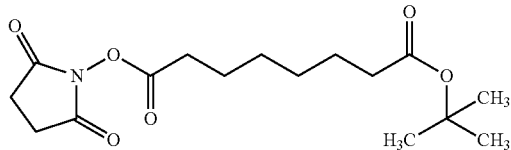 [SMILES: CC(C)(C)OC(=O)CCCCCCC(=O)ON1C(=O)CCC1=O]

Octanedioic acid mono-tert-butyl ester (3.14 g, 13.63 mmol) was dissolved in THF (100 mL). TSTU (4.9 g, 16.3 mmol) was added and pH was adjusted to 8.5 with DIPEA (2.85 mL).

The mixture was stirred under nitrogen overnight, evaporated to dryness, dissolved in EtAc (50 mL) which subsequently was extracted 2 times with HCL (0.1 M). The organic phase was dried with $MgSO_4$, filtered and evaporated resulting in an slightly yellow oil (5 g, containing small amounts of solvent)

LCMS (Method 6): Rt 6.56 min; m/z (M+1) 328. Calcd: 328.

Step 3: 7-(3-{4-[3-(3-Carboxypropionylamino)propoxy]butoxy}propylcarbamoyl)heptanoic acid tert-butyl ester

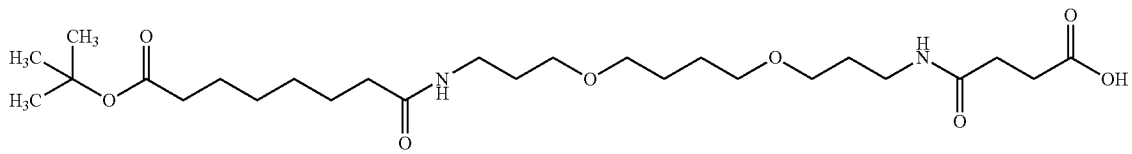 [SMILES: CC(C)(C)OC(=O)CCCCCCC(=O)NCCCOCCCCOCCCNC(=O)CCC(=O)O]

N-{3-[4-(3-tert-butoxycarbonylaminopropoxy)-butoxy]-propyl}succinamic acid (4.60 g, 11.37 mmol) was stirred with TFA (20 mL) at RT for 60 min, after evaporation the residue was stripped with DCM (30 mL×2) and evaporated to dryness.

The resulting oil was dissolved in acetonitrile (30 mL) and octanedioic acid tert-butyl ester 2,5-dioxo-pyrrolidin-1-yl ester (4.46 g, 13.6 mmol) in DMF (20 mL) was added.

pH was adjusted to 8.5 with DIPEA and the mixture was stirred overnight under nitrogen. The mixture was subsequently evaporated to dryness and redissolved in EtAc (50 mL). The EtAc phase was extracted ×3 with HCl (0.1 M), the organic layer dried over magnesium sulphate, filtered and evaporated resulting in a slightly yellow crystalline oil (6.5 g, content of solvent residues)

LCMS (Method 6): Rt 4.31 min; m/z (M+1) 517. Calcd: 517.

The crude product was used for further reaction without further purification.

Step 4. 2-[3-(3-{4-[3-(7-tert-butoxycarbonylheptanoylamino)propoxy]butoxy}-propylcarbamoyl)-propionylamino]pentanedioic acid 1-tert-butyl ester

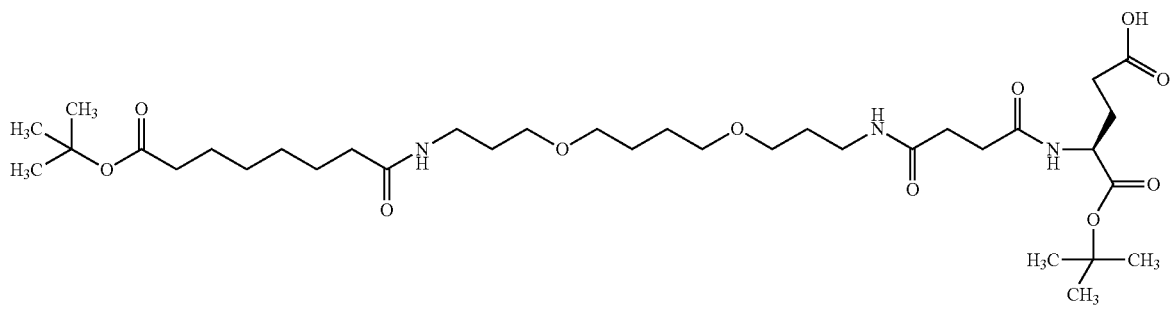 [SMILES: CC(C)(C)OC(=O)CCCCCCC(=O)NCCCOCCCCOCCCNC(=O)CCC(=O)N[C@@H](CCC(=O)O)C(=O)OC(C)(C)C]

7-(3-{4-[3-(3-Carboxypropionylamino)propoxy]butoxy}propylcarbamoyl)heptanoic acid tert-butyl ester (5.9 g), the crude product from above, was dissolved in THF (20 mL), TSTU (4.13 g, 13.7 mmol) was added together with DMF (6 mL), pH was adjusted to 8.2 with DIPEA (2.6 mL). The mixture was stirred overnight under nitrogen.

The mixture was evaporated and the residue dissolved in EtAc which was extracted with HCl (0.1 M) 3 times.

The organic layer was dried with magnesium sulphate, filtered and the filtrate evaporated to give an oil.

LCMS (Method 6): Rt 4.57 min; m/z 614 corresponding to the activated acid.

This was dissolved in THF (30 mL), pH was adjusted to 8.2 with DIPEA (0.4 mL) and H-glu-OtBu (1.7 g, 4.9 mmol) was added together with DMF (10 mL).

The mixture was stirred at RT for 3 h, filtration followed by evaporation afforded a thick yellow oil.

This was extracted between EtAc and HCl (0.1 M) as reported above, and the resulting dried EtAc layer gave 3.5 g crude product on evaporation. LCMS (Method 6): Rt 4.77 min; m/z (M+1) 702.

The crude product was purified on Gilson using acidic HPLC on a C18 column (Jones, Kromasil RP18 5 µm 15×225 mm).

Gradient: 0.0-10.0 min 35% A; 10.0-25.0 min 35-80% A; 25-30 min 90% A; 30-35 min 100% A.

The product was collected in fractions from 21-22.5 min. The combined fractions were evaporated yielding the wanted product (1.8 g)

LCMS (Method 6): Rt 4.77 min; m/z (M+1) 702, Calcd. 702.

Step 5. 2-[3-(3-{4-[3-(7-tert-butoxycarbonylheptanoylamino)propoxy]butoxy}propylcarbamoyl)-propionylamino]pentanedioic acid 5-tert-butyl ester 1-(2,5-dioxopyrrolidin-1-yl) ester

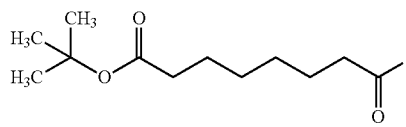
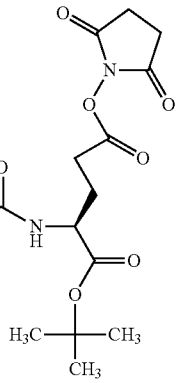

2-[3-(3-{4-[3-(7-tert-butoxycarbonylheptanoylamino)propoxy]butoxy}-propylcarbamoyl)-propionylamino]pentanedioic acid 1-tert-butyl ester (1.5 g, 2.14 mmol) was dissolved in THF (20 mL), pH was adjusted to 8.5 with DIPEA (0.9 mL), TSTU (0.83 g, 2.77 mmol) was added in DMF (5 mL). The mixture was stirred under nitrogen overnight, subsequent evaporation and extraction between EtAc and HCl as described above resulted in 1.75 g crude product.

LCMS (Method 6): Rt 5.10 min; m/z (M+1) 800, Calcd.: 800.

Step 6. $N^{\epsilon B29}$-(3-(3-{4-[3-(7-carboxyheptanoylamino)propoxy]butoxy}propylcarbamoyl)-propionyl-γ-glutamyl) desB30 human insulin

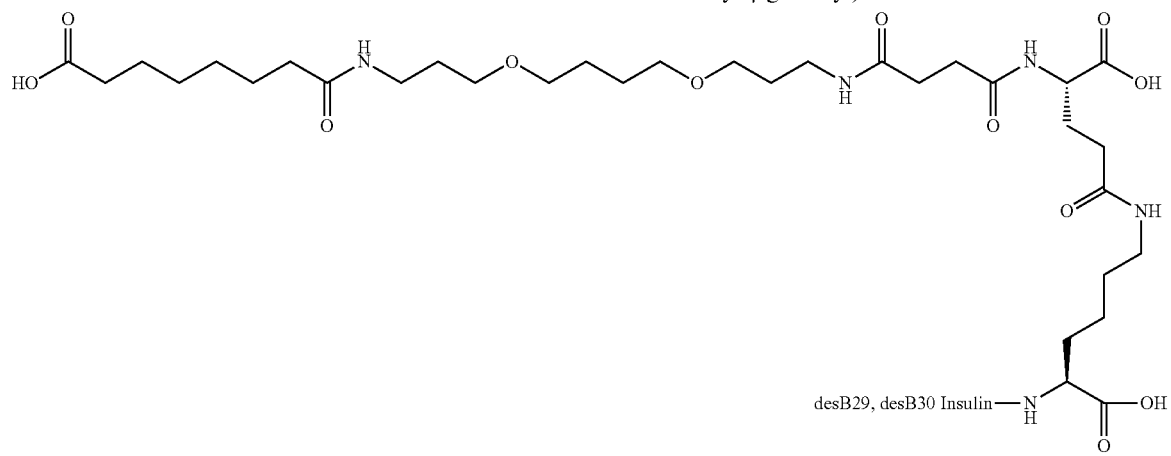

2-[3-(3-{4-[3-(7-tert-butoxycarbonylheptanoylamino)propoxy]butoxy}propylcarbamoyl)-propionylamino]pentanedioic acid 5-tert-butyl ester 1-(2,5-dioxopyrrolidin-1-yl) ester (0.255 g, 0.319 mmol) was dissolved in acetonitrile (10 mL) and added to a solution of desB30 human insulin (1.82 g) dissolved in Na$_2$CO$_3$ solution (10 mL, pH 10.3), pH was adjusted to 10.1 with NaOH (0.1M). The mixture was stirred at RT for 2 h, then pH was adjusted to 5.5 by means of HCl(2M, 3 mL) resulting in the precipitation of an oily crystalline mass.

This was isolated and dissolved in water acetic acid (1 M) and freeze dried.

The resulting product was dissolved in water and purified on Gilson using acidic HPLC on a C18 column (Jones, Kromasil RP18 5 µm 15×225 mm).

Gradient: 0.0-5.0 min 35% A; 5.0-25.0 min 35-80% A; 25-30 min 90% A; 30-35 min 100% A. Fractions around Rt 15 min were collected, mixed and evaporated.

The product was treated with TFA/DCM 1/1 (20 mL) by stirring at RT for 1 h, subsequent evaporation to dryness and stripping with DCM 40 mL×2 resulted in the deprotected product which was dissolved in water and freeze dried giving 540 mg of the wanted product.

MALDI.TOF-MS: m/z 6276.66; calc. 6276.
HPLC (method 5); Rt 10.19 min.

Example 9

Synthesis of N$^{\epsilon B29}$-(3-(3-{2-[2-(3-[9-Carboxynonanoylamino]propoxy)ethoxy]ethoxy}-propylcarbamoyl)propionyl) desB30 human insulin

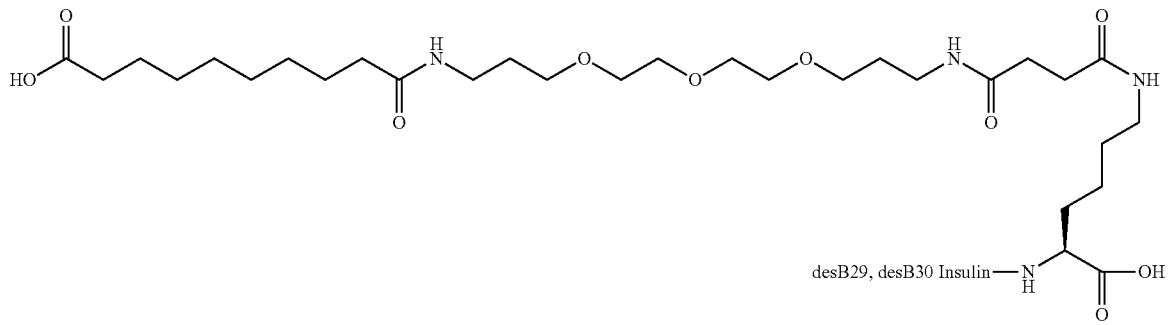

Following the procedure from example 7, but exchanging the diacid part gave the product.

Preparation following step 6 in example 8 using 0.114 mmol of desB30 insulin resulted in 0.96 g of the protected compound.

Gilson purification using acidic HPLC on a C18 column (Jones, Kromasil RP18 5 µm 15×225 mm). Gradient: 0.0-1.0 min: 35% CH3CN, 1.00-15.0 min: 35-55% CH3CN, 15.0-20.0 min: 55% CH3CN Flow: 10 ml/min. Rt=12.5-14.0 min.

Deprotection my means of TFA gave 0.141 g colourless compound after freeze drying.

MALDI-TOF-MS (matrix SA): m/z 6195; calc. 6186
HPLC (method 5): Rt; 4.094 min.

Decanedioic acid tert-butyl ester 2,5-dioxo-pyrrolidin-1-yl ester.

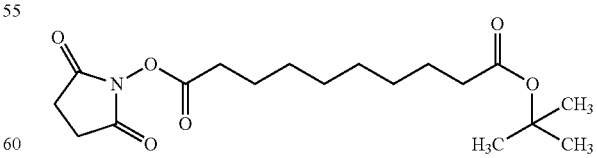

Preparation as described in step 2 example 8 gave 5.57 g crude product which was used without further purification.
LCMS (Method 6): Rt 5.82 min; m/z (M+1) 356, Calcd.: 355.

Example 10

Synthesis of N^εB29-(3-(2-{2-[2-(9-carboxynonanoylamino)ethoxy]ethoxy}ethylcarbamoyl) propionyl-γ-glutamyl) desB30 human insulin

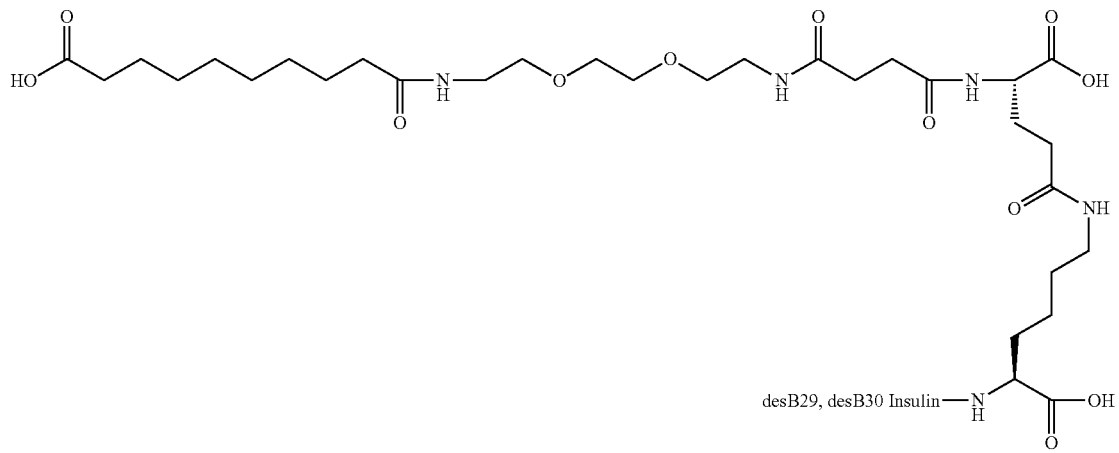

The preparation was performed using the methodology described in example 8

(S)-2-[3-(2-{2-[2-(9-tert-Butoxycarbonylnonanoylamino)ethoxy]ethoxy}-ethylcarbamoyl)propionylamino]pentanedioic acid 1-tert-butyl ester (0.59 g, 0.876 mmol) was activated with TSTU, 0.132 g (0.171 mmol) the crude reaction product was reacted with desB30 insulin (0.154 mmol) as described in example 8

This resulted in 740 mg of oily precipitate which was freeze-dried and purified on Gilson using acidic HPLC on a C18 column (Jones, Kromasil RP18 5 μm 15×225 mm).

Gradient: 0.0-5.0 min 30% A; 5.0-20.0 min 35-50% A.

105 mg of target compound was isolated. MALDI.TOF-MS (matrix Cyano): m/z 6245.9; calc. 6243.

HPLC (method 5); Rt 8.759 min.

N-{2-[2-(2-tert-butoxycarbonylamino-ethoxy)-ethoxy]-ethyl}-succinamic acid.

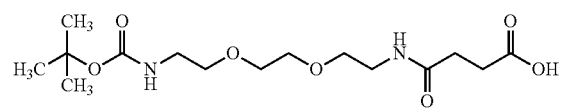 [SMILES: CC(C)(C)OC(=O)NCCOCCOCCNC(=O)CCC(=O)O]

Preparation from 1-(t-butyloxycarbonylamino)-3,6-dioxa-8-octanamine) (5 g, 20.16 mmol) and succinic anhydride (2.218 g, 22.18 mmol) gave a thick yellow oil which crystallised on standing (6.5 g, yield 98%). LCMS (Method 6): Rt 2.99 min; m/z (M+1) 349; Calcd.: 349.

9-(2-{2-[2-(3-carboxypropionylamino)ethoxy]ethoxy}ethylcarbamoyl)nonanoic acid tert-butyl ester

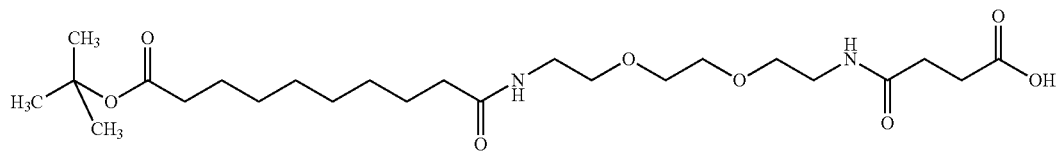 [SMILES: CC(C)(C)OC(=O)CCCCCCCCC(=O)NCCOCCOCCNC(=O)CCC(=O)O]

Preparation from decanedioic acid tert-butyl ester 2,5-dioxo-pyrrolidin-1-yl ester (1.13 g, 3.45 mmol) and N-{2-[2-(2-tert-butoxycarbonylamino-ethoxy)-ethoxy]-ethyl}-succinamic acid (1 g, 2.84 mmol) as described in step 3 example 8 gave 1.68 g crude product which was used without further purification. LCMS (Method 6): Rt 3.86 min; m/z (M+1) 489; Calcd.: 489.

(S)-2-[3-(2-{2-[2-(9-tert-Butoxycarbonylnonanoy-lamino)ethoxy]ethoxy}-ethylcarbamoyl)propiony-lamino]pentanedioic acid 1-tert-butyl ester

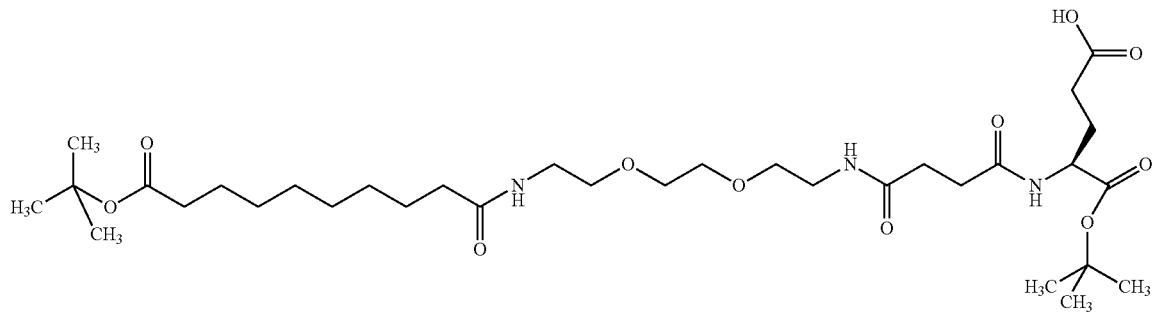 [SMILES: CC(C)(C)OC(=O)CCCCCCCCC(=O)NCCOCCOCCNC(=O)CCC(=O)N[C@@H](CCC(=O)O)C(=O)OC(C)(C)C]

Preparation from 9-(2-{2-[2-(3-carboxypropionylamino) ethoxy]ethoxy}-ethylcarbamoyl)nonanoic acid tert-butyl ester (1.4 g, 2.86 mmol) and glu-OtBu (0.87 g, 4.29 mmol) following the method described step 4 example 8 gave 1.8 g crude product. LCMS (Method 6): Rt 5.1 min; m/z (M+1) 674; Calcd.: 674.

Gilson purification using acidic HPLC on a C18 column (Jones, Kromasil RP18 5 µm 15×225 mm), Gradient: 0.0-10.0 min: 35% CH$_3$CN, 10.00-25.0 min: 35-90% CH3CN, Flow: 10 ml/min. Fractions at Rt=20.0-25.0 min were collected and evaporated to dryness giving 0.590 g of a yellow oil. LCMS (Method 6): Rt 5.1 min; m/z (M+1) 674; Calcd.: 674.

Example 11

Synthesis of N$^{\epsilon B29}$-(3-(3-{4-[3-(9-Carboxynonanoy-lamino)propoxy]butoxy}-propylcarbamoyl)propio-nyl-γ-glutamyl) desB30 human insulin

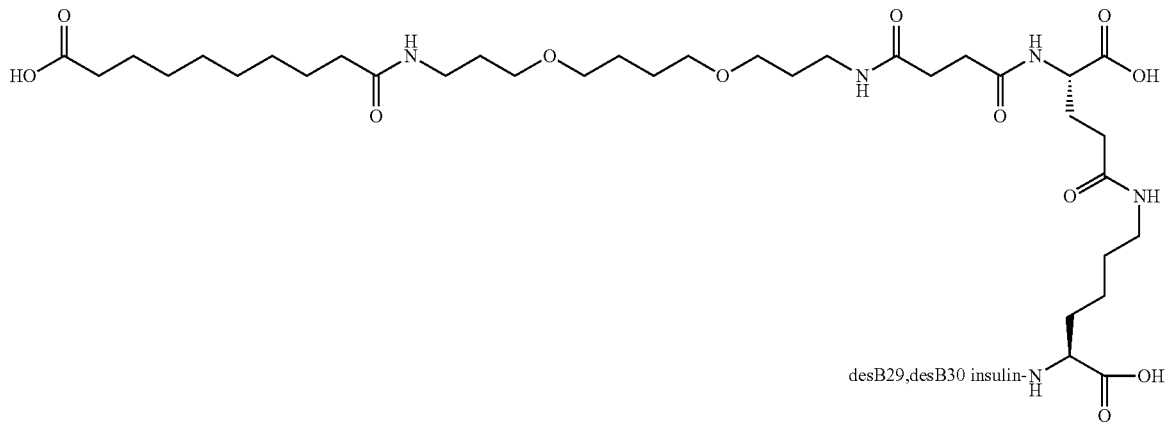 [SMILES: N[C@@H](CCCCNC(=O)CC[C@H](NC(=O)CCC(=O)NCCCOCCCCOCCCNC(=O)CCCCCCCCC(=O)O)C(=O)O)C(=O)O]

(S)-2-[3-(3-{4-[3-(9-tert-Butoxycarbonylnonanoylamino) propoxy]butoxy}-propylcarbamoyl)propionylamino]pen-tanedioic acid 5-tert-butyl ester 1-(2,5-dioxopyrrolidin-1-yl) ester (0.06 g, 0.073 mmol) and desB30 insulin (0.065 mmol) were reacted as described in example 8. The TFA treated product was purified on Gilson using acidic HPLC on a C18 column (Jones, Kromasil RP18 5 µm 15×225 mm).

Gradient: 0.0-5.0 min 30% A; 5.0-20.0 min 35-50% A. fractions at Rt 16.0 min-17.5 min were collected evaporated and subsequently freeze-dried. Yield 34 mg.

MALDI.TOF-MS: m/z 6305.69; calc. 6299.
HPLC method 5; Rt 8.850 min.

9-(3-{4-[3-(3-Carboxypropionylamino)propoxy]butoxy}propylcarbamoyl)nonanoic acid tert-butyl ester

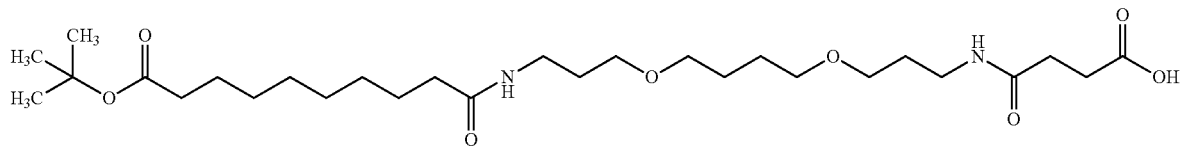 [SMILES: CC(C)(C)OC(=O)CCCCCCCCC(=O)NCCCOCCCCOCCCNC(=O)CCC(=O)O]

Preparation from decanedioic acid tert-butyl ester 2,5-dioxo-pyrrolidin-1-yl ester (0.88 g, 2.47 mmol) and N-{3-[4-(3-tert-butoxycarbonylaminopropoxy)-butoxy]-propyl}succinamic acid (1 g, 2.47 mmol) as described in example 8 afforded 150 mg compound after purification.

LCMS (Method 6): Rt 4.31 min; m/z (M+1) 545; Calcd.: 545.

(S)-2-[3-(3-{4-[3-(9-tert-butoxycarbonylnonanoylamino)propoxy]butoxy}propylcarbamoyl) propionylamino]pentanedioic acid 1-tert-butyl ester

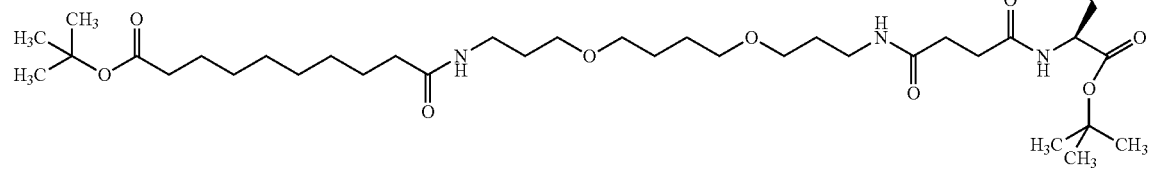

9-(3-{4-[3-(3-Carboxypropionylamino)propoxy]butoxy}propylcarbamoyl)nonanoic acid tert-butyl ester (0.15 g, 0.276 mmol) was activated with TSTU, the resulting OSu-derivative was reacted with H-Glu-OtBu (0.076 g, 0.37 mmol) as described previously. After work up the resulting oil was purified on Gilson using acidic HPLC on a C18 column (Jones, Kromasil RP18 5 µm 15×225 mm).

Gradient: 0.0-5.0 min 20% A; 5.0-20.0 min 20-90% A. fractions at Rt 24.5 min-25.5 min were collected evaporated and subsequently freeze-dried. Yield 50 mg. LCMS Method 6: Rt 5.43 min; m/z (M+1) 730; Calcd.: 730.

This compound was activated with TSTU resulting in 60 mg crude (S)-2-[3-(3-{4-[3-(9-tert-Butoxycarbonylnonanoylamino)propoxy]butoxy}propylcarbamoyl)propionylamino]-pentanedioic acid 5-tert-butyl ester 1-(2,5-dioxopyrrolidin-1-yl) ester

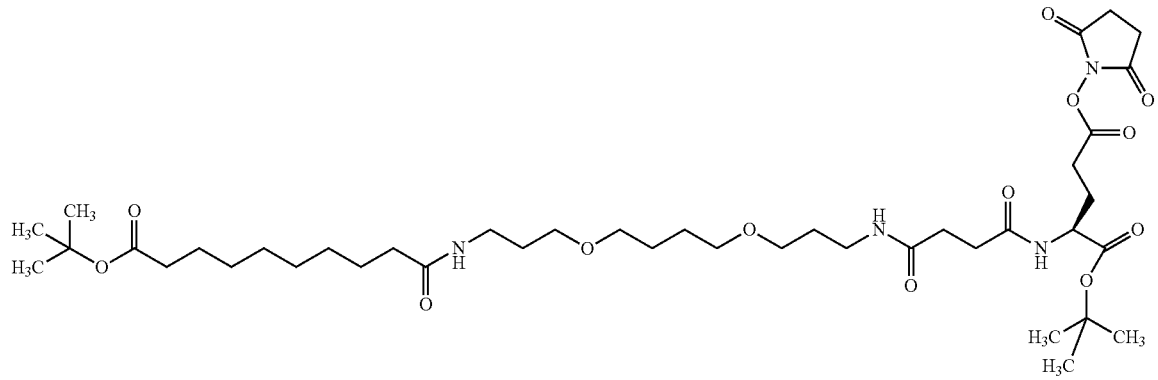 [SMILES: CC(C)(C)OC(=O)CCCCCCCCC(=O)NCCCOCCCCOCCCNC(=O)CCC(=O)N[C@@H](CCC(=O)ON1C(=O)CCC1=O)C(=O)OC(C)(C)C]

LCMS Method 6: Rt 5.79 min; m/z (M+Na) 850; Calcd.: 850.

The crude product was used without further purification.

Example 12

Synthesis of N^{εB29}-(2-[3-(2-(2-{2-(7-carboxyheptanoylamino)ethoxy}ethoxy)-ethylcarbamoyl]propionyl-γ-glutamyl) desB30 human insulin

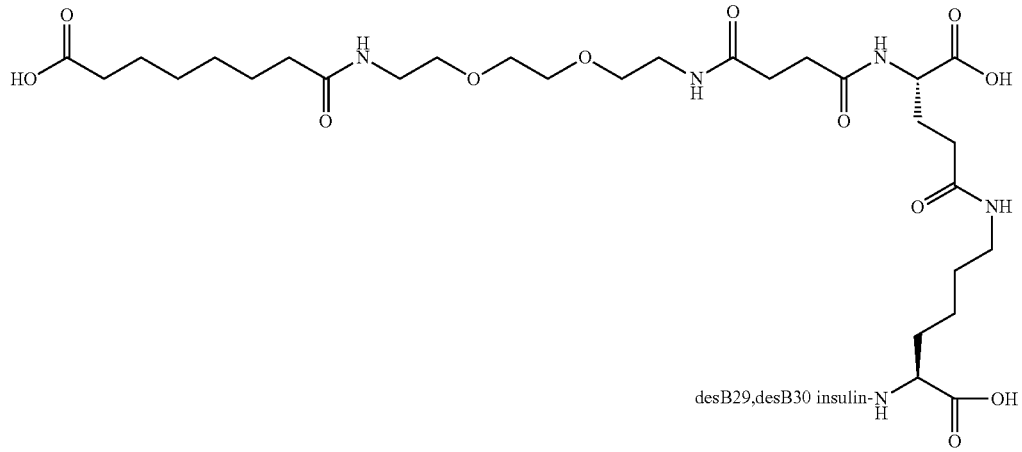 [SMILES: N[C@@H](CCCCNC(=O)CC[C@H](NC(=O)CCC(=O)NCCOCCOCCNC(=O)CCCCCCC(=O)O)C(=O)O)C(=O)O]

(S)-2-[3-(2-{2-[2-(7-tert-Butoxycarbonylheptanoylamino)ethoxy]ethoxy}ethylcarbamoyl)-propionylamino]pentanedioic acid 5-tert-butyl ester 1-(2,5-dioxopyrrolidin-1-yl) ester (0.126 g, 0.17 mmol) was reacted with desB30 insulin (0.153 mmol) as described above. The crude product after TFA treatment (0.750 mg) was purified two times on Gilson using acidic HPLC on a C18 column (Jones, Kromasil RP18 5 μm 15×225 mm).

Gradient: 0.0-5.0 min 25% A; 5.0-20.0 min 20-50%. Fractions from Rt 21.0-22.0 min collected and evaporated resulting in 13 mg compound.

MALDI.TOF-MS (matrix SA): m/z 6221.15; calc. 6215.
LCMS (Method 6): Rt 3.53 min; m/z (M+4/4) 1556; Calcd.: 1554

7-(2-{2-[2-(3-Carboxy-propionylamino)-ethoxy]-ethoxy}-ethylcarbamoyl)-heptanoic acid tert-butyl ester

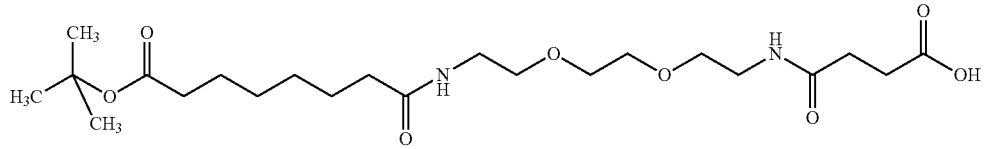 [SMILES: CC(C)(C)OC(=O)CCCCCCC(=O)NCCOCCOCCNC(=O)CCC(=O)O]

Octanedioic acid tert-butyl ester 2,5-dioxo-pyrrolidin-1-yl ester (1.13 g, 3.45 mmol) and N-{2-[2-(2-tert-butoxycarbonylamino-ethoxy)-ethoxy]-ethyl}-succinamic acid (1 g, 2.874 mmol) were reacted as described above. 1.75 g crude product was isolated and used without further purification. LCMS (Method 6): Rt 3.86 min; m/z (M+1) 461; Calcd.: 461.

(S)-2-[3-(2-{2-[2-(7-tert-Butoxycarbonylheptanoylamino)ethoxy]ethoxy}-ethylcarbamoyl)propionylamino]pentanedioic acid 1-tert-butyl ester

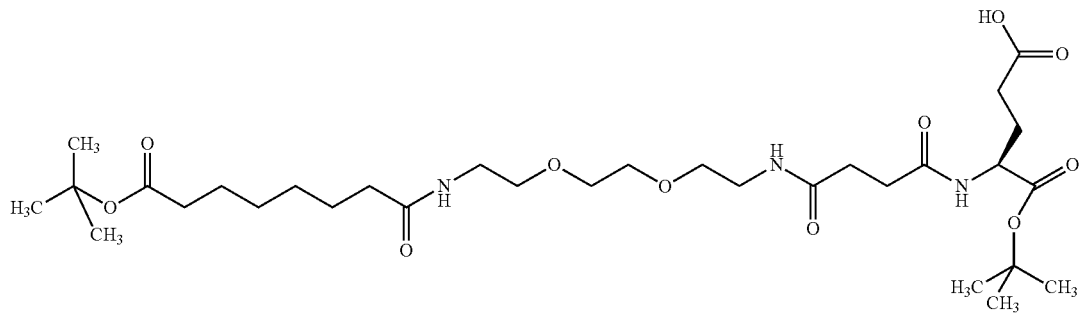 [SMILES: CC(C)(C)OC(=O)CCCCCCC(=O)NCCOCCOCCNC(=O)CCC(=O)N[C@@H](CCC(=O)O)C(=O)OC(C)(C)C]

7-(2-{2-[2-(3-Carboxy-propionylamino)-ethoxy]-ethoxy}-ethylcarbamoyl)-heptanoic acid tert-butyl ester (1.3 g, 2.83 mmol) was activated with TSTU and subsequently the crude product was reacted with H-glu-OtBu (0.86 g, 4.2 mmol). After work up using the method described in example 8, the product was further purified on Gilson using acidic HPLC on a C18 column (Jones, Kromasil RP18 5 μm 15×225 mm).

Gradient: 0.0-10.0 min 30% A; 10.0-25.0 min 30-90% A, fractions at Rt 20-25 min were collected and evaporated resulting in 600 mg product which was used for TSTU activation described below. LCMS (Method 6): Rt 4.51 min; m/z (M+1) 646; Calcd.: 646.

(S)-2-[3-(2-{2-[2-(7-tert-Butoxycarbonylheptanoylamino)ethoxy]ethoxy}-ethylcarbamoyl)propionylamino]pentanedioic acid 5-tert-butyl ester 1-(2,5-dioxopyrrolidin-1-yl) ester

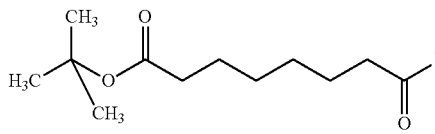
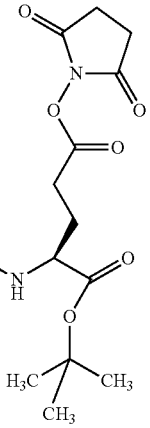

(S)-2-[3-(2-{2-[2-(7-tert-Butoxycarbonylheptanoylamino)ethoxy]ethoxy}-ethylcarbamoyl)propionylamino]pentanedioic acid 1-tert-butyl ester (0.6 g, 0.93 mmol) was activated with TSTU using the procedure described above.

This resulted in 0.75 g crude compound which was used without further purification.

LCMS (Method 6): Rt 4.81 min; m/z (M+1) 743; Calcd.: 743

Example 13

Synthesis of $N^{\epsilon B29}$-(3-[2-(2-{2-[2-(15-carboxypentadecanoylamino)ethoxy]ethoxy}ethoxy)-ethoxy]propionyl)) desB30 human insulin

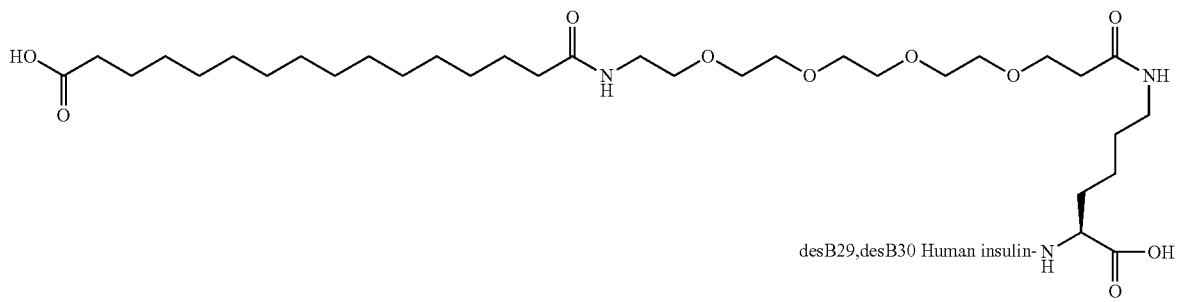 [SMILES: N[C@@H](CCCCNC(=O)CCOCCOCCOCCOCCNC(=O)CCCCCCCCCCCCCCC(=O)O)C(=O)O]

This compound was prepared similarly as described in example 4. The intermediate 15-[2-(2-{2-[2-(2-Carboxy-ethoxy)ethoxy]ethoxy}ethoxy)ethylcarbamoyl]pentadecanoic acid tert-butyl ester was activated to the OSu-ester using TSTU and coupled to desB30 human insulin. Deprotection using TFA afforded the title compound.

MALDI-TOF MS: m/z=6222. Calculated: 6222
HPLC (Method 1): $R_t$=11.12 min.
HPLC (Method 5): $R_t$=12.03 min.

Example 14

Synthesis of N$^{\epsilon B29}$-(3-(2-{2-[2-(2-{2-[2-(2-{2-[2-(2-{2-[2-(13-carboxy-tridecanoylamino)-ethoxy]-ethoxy}-ethoxy)-ethoxy]-ethoxy}-ethoxy)-ethoxy]-ethoxy}-ethoxy)-ethoxy]-ethoxy}-ethoxy)-propionoyl-γ-glutamyl) desB30 human insulin

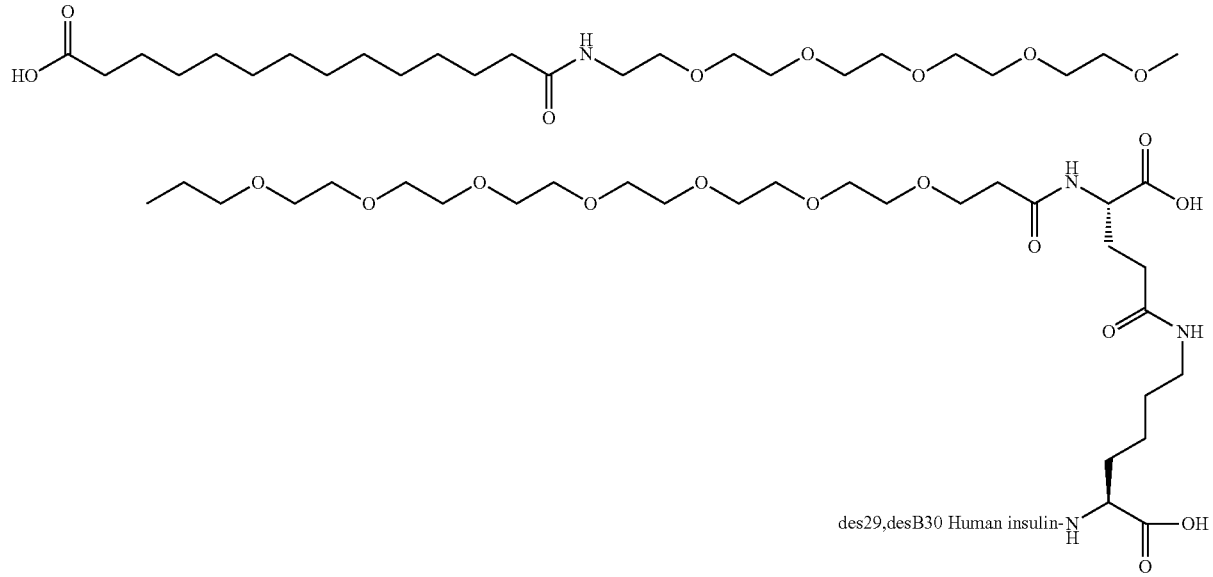

This compound was prepared in analogy with example 1 via reaction of H$_2$N(CH$_2$CH$_2$O)$_{12}$CH$_2$CH$_2$COOH (Quanta Biodesign, OH, USA) with tert-butyl O-succinimidyl tetradecanedioate followed by activation with TSTU, reaction with L-Glu-OtBu, activation with TSTU, coupling with DesB30 human insulin and deprotection by TFA.

LCMS 6676.0, method 6, calculated 6675.8.

Example 15

Synthesis of N$^{\epsilon B29}$-(3-[2-(2-(2-[2-(13-Carboxy-tridecanoylamino)-ethoxy)-ethoxy]-ethoxy)-ethoxy]-propionoyl-γ-glutamyl) desB30 human insulin

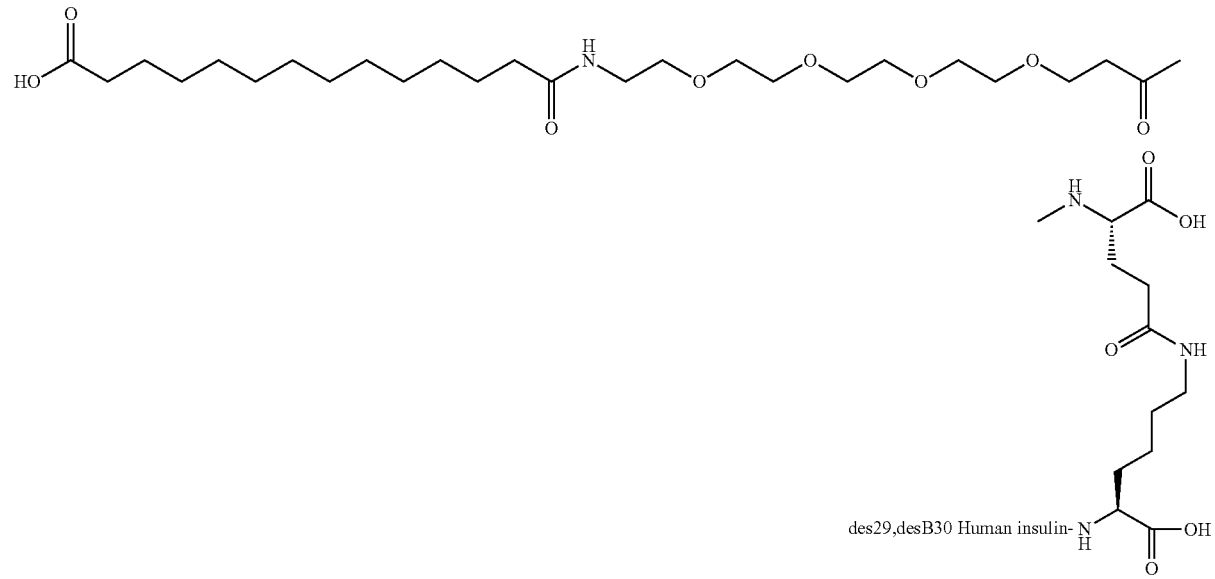

This compound was prepared in analogy with example 1 via reaction of H$_2$N(CH$_2$CH$_2$O)$_4$—CH$_2$CH$_2$COOH (Quanta Biodesign, OH, USA) with tert-butyl O-succinimidyl tetradecanedioate followed by activation with TSTU, reaction with L-Glu-OtBu, activation with TSTU, coupling with DesB30 human insulin and deprotection by TFA.

LCMS 6323.2, (method 6) calculated 6323.3.

Example 16

Synthesis of N$^{\epsilon B29}$-(3-[2-(2-{2-[2-(2-{2-[2-(13-carboxy-tridecanoylamino)-ethoxy]-ethoxy)-ethoxy)-ethoxy]-ethoxy}-ethoxy)-ethoxy]-ethoxy}-propionyl-γ-glutamyl) desB30 human insulin

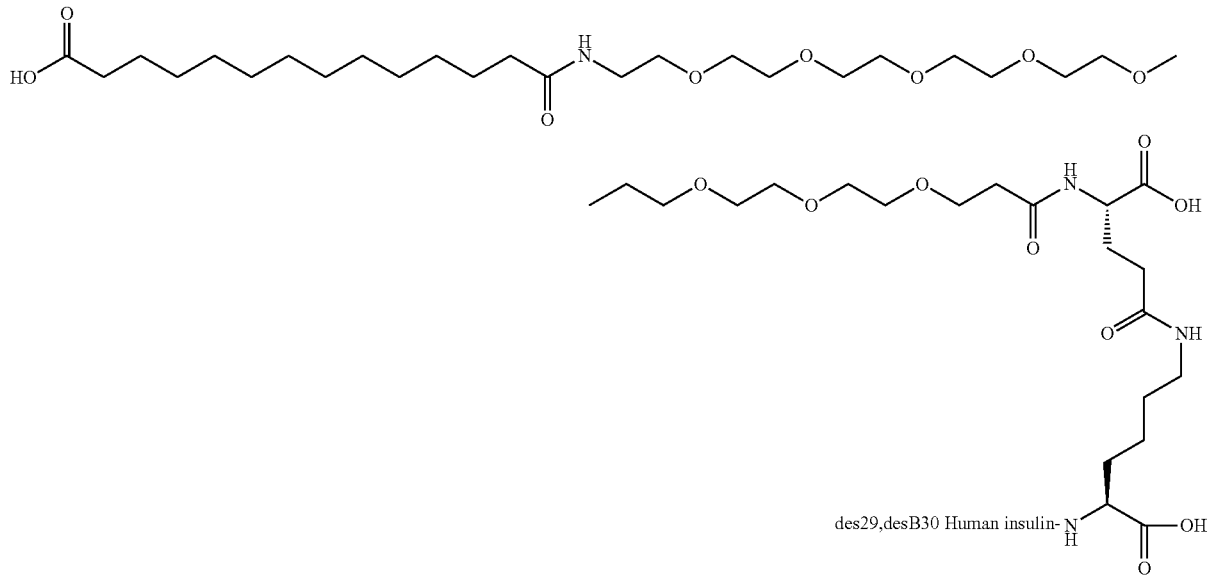

This compound was prepared in analogy with example 1 via reaction of H$_2$N(CH$_2$CH$_2$O)$_8$CH$_2$CH$_2$COOH (Quanta Biodesign, OH, USA) with tert-butyl O-succinimidyl tetradecanedioate followed by activation with TSTU, reaction with L-Glu-OtBu, activation with TSTU, coupling with Des(B30) human insulin and deprotection by TFA.

LCMS 6498.8, method 6, calculated 6499.6.

Example 17

Synthesis of N$^{\epsilon B29}$-(3-(2-{2-[2-(15-Carboxy-pentadecanoylamino)-ethoxy]-ethoxy}-ethylcarbamoyl)-propionyl-γ-glutamyl) desB30 human insulin

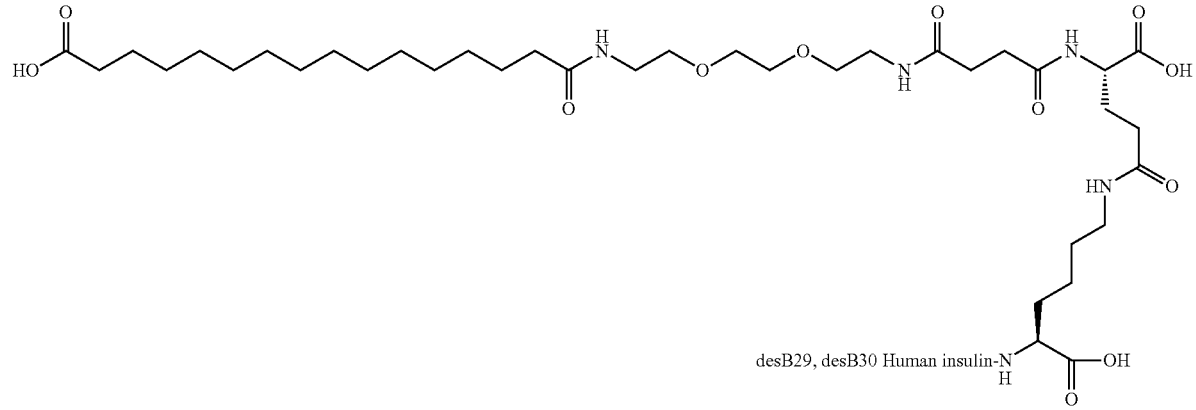

MALDI-TOF MS (matrix:SA): m/z=6336. Calculated: 6334

HPLC (Method 1): Rt=11.71 min.
HPLC (Method 5): R=9.37 min.

Example 18

Synthesis of N^εB29-(3-(3-{2-[2-(3-[15-Carboxypentadecanoylamino]propoxy)ethoxy]-ethoxy}propylcarbamoyl)propionyl-γ-glutamyl) desB30 human insulin

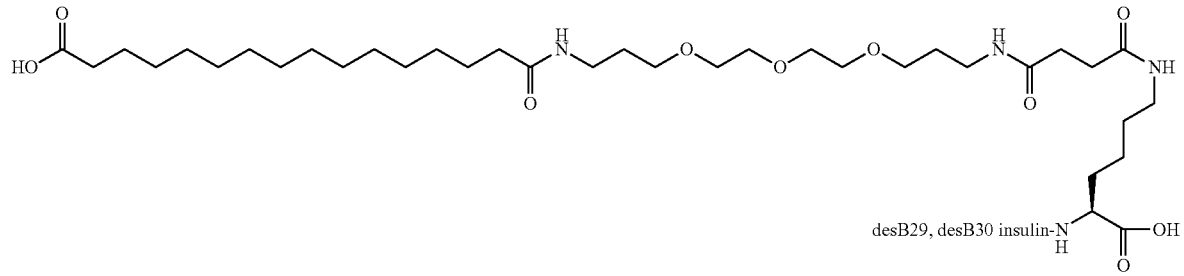

15-{3-[2-(2-{3-[3-(2,5-Dioxopyrrolidin-1-yloxycarbonyl)propionylamino]propoxy}ethoxy)ethoxy]-propylcarbamoyl}pentadecanoic acid tert-butyl ester (crude product 0.196 g, 0.264 mmol) reacted with desB30 insulin (0.132 mmol) as described above resulting in 400 mg precipitate which was Gilson purified, gradient: 0.0-5.0 min 40% A; 5.0-15.0 min 40-80% A, fractions at Rt 15.5-16.0 min were collected and evaporated to dryness.

The resulting mass was subsequently treated with TFA/DCM 1/1 (100 mL) in order to deprotect the carboxy groups. After evaporation the resulting product was purified 3 times on Gilson HPLC on a C18 column (Jones, Kromasil RP18 5 μm 15×225 mm).

Gradient: 0.0-5.0 min 35% A; 5.0-20.0 min 20-90%. Fractions from Rt 15.0-16.0 min collected and evaporated resulting in 23 mg compound.

MALDI-TOF-MS: m/z 6277.15; calc. 6270.
HPLC (method 5): Rt 9.50 min.

ω-{3-[2-(2-{3-[3-(2,5-Dioxopyrrolidin-1-yloxycarbonyl)propionylamino]propoxy}ethoxy)-ethoxy]propylcarbamoyl}pentadecanoic acid tert-butyl ester

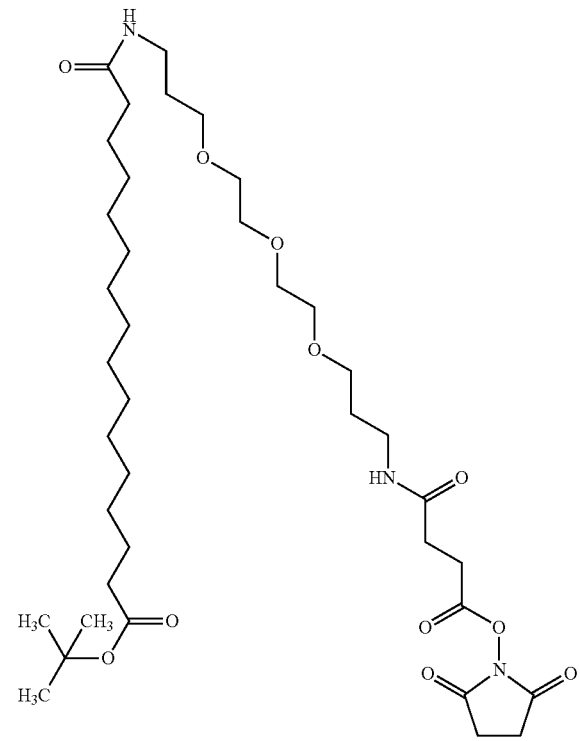 [SMILES: CC(C)(C)OC(=O)CCCCCCCCCCCCCCC(=O)NCCCOCCOCCOCCCNC(=O)CCC(=O)ON1C(=O)CCC1=O]

Preparation from ω-[3-(2-{2-[3-(3-carboxypropionylamino)propoxy]ethoxy}ethoxy) propylcarbamoyl-[pentadecanoic acid tert-butyl ester (0.17 g, 0.264 mmol) and TSTU gave 196 mg crude product which was used without further purification. LCMS Method 6: Rt 7.36 min; m/z (M+1) 742; Calcd.: 742.

ω-[3-(2-{2-[3-(3-carboxypropionylamino)propoxy]ethoxy}ethoxy)-propylcarbamoyl]pentadecanoic acid tert-butyl ester

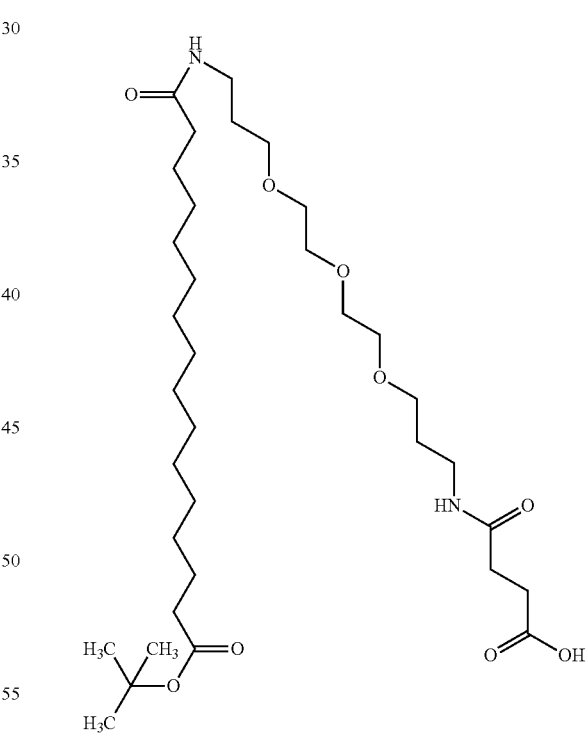

Hexadecanedioic acid tert-butyl ester 2,5-dioxo-pyrrolidin-1-yl ester (0.5 g, 1.13 mmol) and N-(3-{2-[2-(3-aminopropoxy)ethoxy]ethoxy}propyl)succinamic acid (0.36 g, 1.13 mmol) were reacted as described above.

Purification of the crude product on Gilson HPLC on a C18 column (Jones, Kromasil RP18 5 μm 15×225 mm). Gradient: 0.0-1.0 min 50% A; 1.0-30.0 min 50-90%. Fractions with Rt 24.0-26.0 min collected and evaporated resulting in 170 mg of the target product.

LCMS (Method 6): Rt 7.06 min; m/z (M+1) 645; Calcd.: 645.

Example 19

Synthesis of $N^{\epsilon B29}$-(3-(3-{4-[3-(ω-Carboxyundecanoylamino)propoxy]butoxypropylcarbamoyl)-propionyl-γ-glutamyl) desB30 human insulin

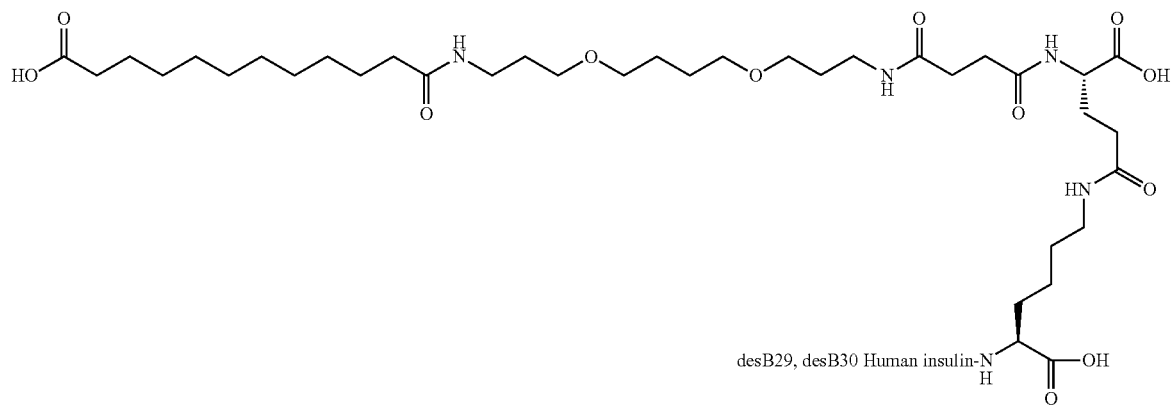

This compound was prepared similarly as described in example 8 using dodecanoic acid mono tert-butyl ester.

Data for the Title Compound:
MALDI-TOF-MS: m/z=6332. Calculated: 6334
HPLC (Method 1): $R_t$=9.57 min.
HPLC (Method 5): $R_t$=7.50 min.
HPLC (Method 6): $R_t$=4.11 min; m/z: 1584 (M+4)/4. Calcd: 1584.

Example 20

$N^{\epsilon B29}$-(3-(3-{4-[3-(ω-Carboxytridecanoylamino)propoxy]butoxypropylcarbamoyl)-propionyl-γ-glutamyl) desB30 human insulin

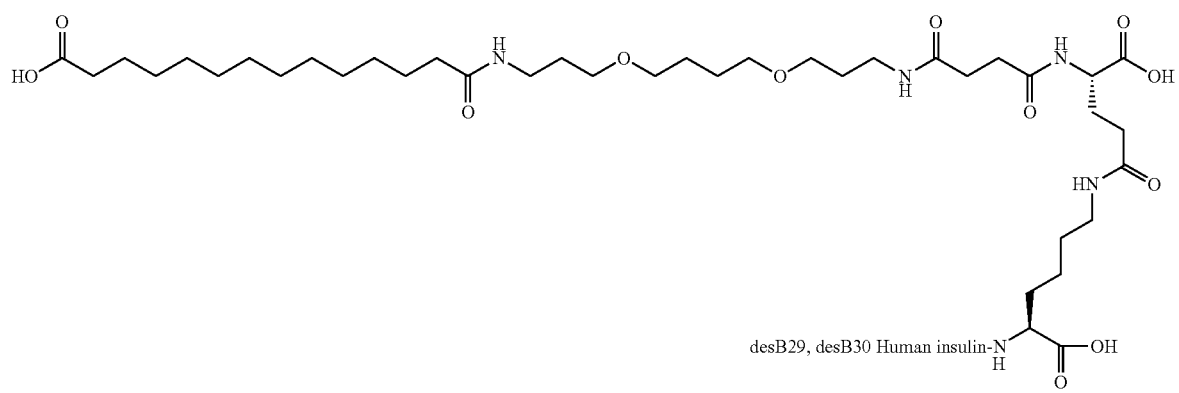

Example 21
N$^{\epsilon B29}$-(3-(2-{2-[2-(ω-Carboxyundecanoylamino)
ethoxy]ethoxy}ethylcarbamoyl)propionyl-γ-
glutamyl) desB30 human insulin
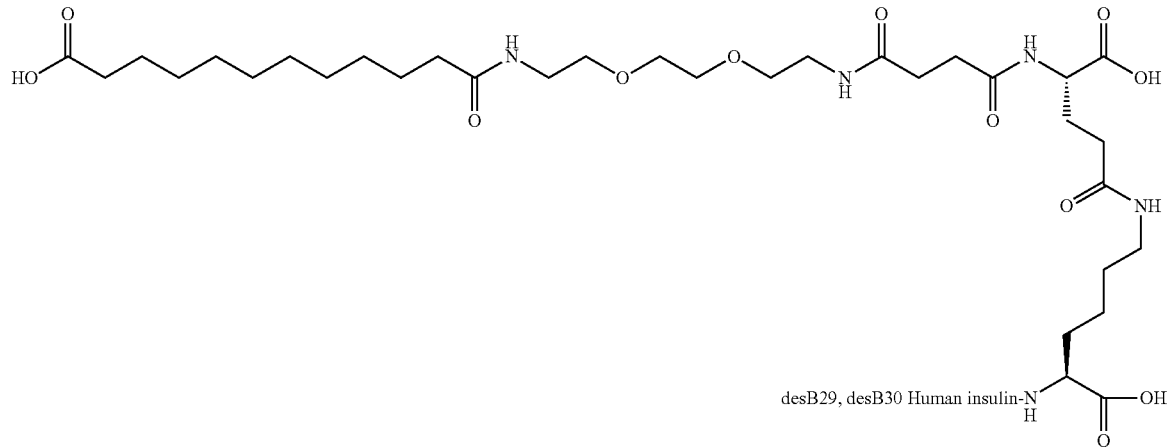
Example 22
N$^{\epsilon B29}$-(3-(2-{2-[2-(ω-carboxytridecanoylamino)
ethoxy]ethoxy}ethylcarbamoyl)propionyl-γ-
glutamyl) desB30 human insulin
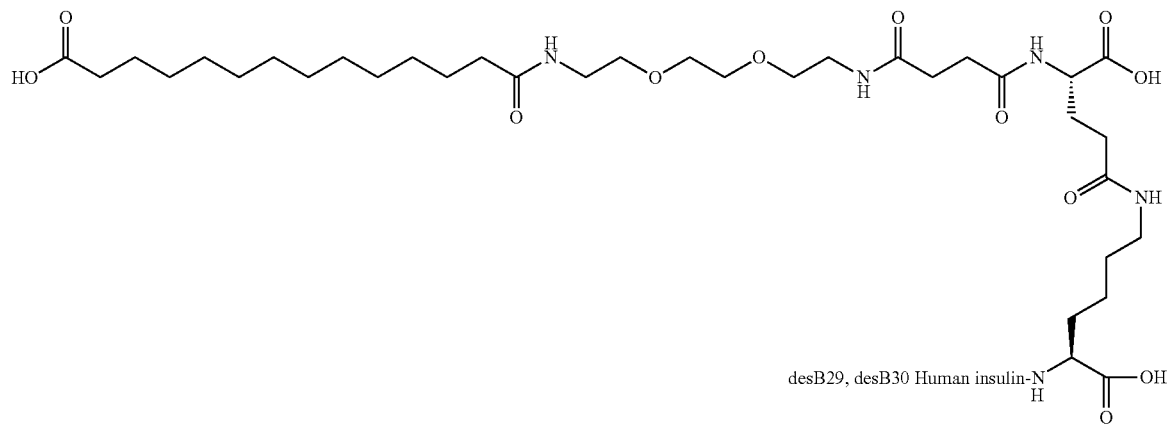

Example 23

N$^{\epsilon B29}$-{3-[2-(2-{2-[2-(ω-Carboxy-pentadecanoy-lamino)ethoxy]ethoxy}ethoxy)ethoxy]propionyl-gamma-γ-D-glutamyl) desB30 human insulin

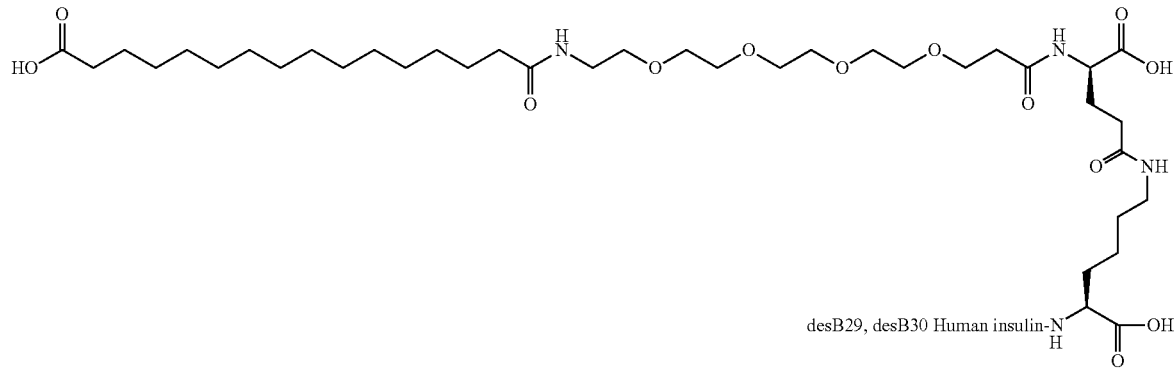

Example 24

N$^{\epsilon B29}$-{3-[2-(2-{2-[2-(7-carboxyheptanoylamino)ethoxy]ethoxy}ethoxy)ethoxy]propionyl-γ-glutamyl} desB30 human insulin

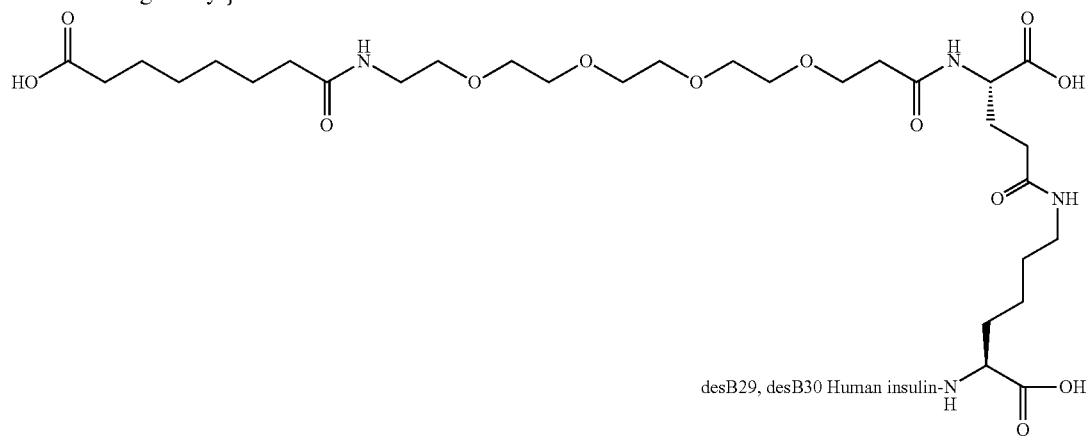

Example 25

N$^{\epsilon B29}$-{3-[2-(2-{2-[2-(9-carboxynonanoylamino)ethoxy]ethoxy}ethoxy)ethoxy]propionyl-γ-glutamyl} desB30 human insulin

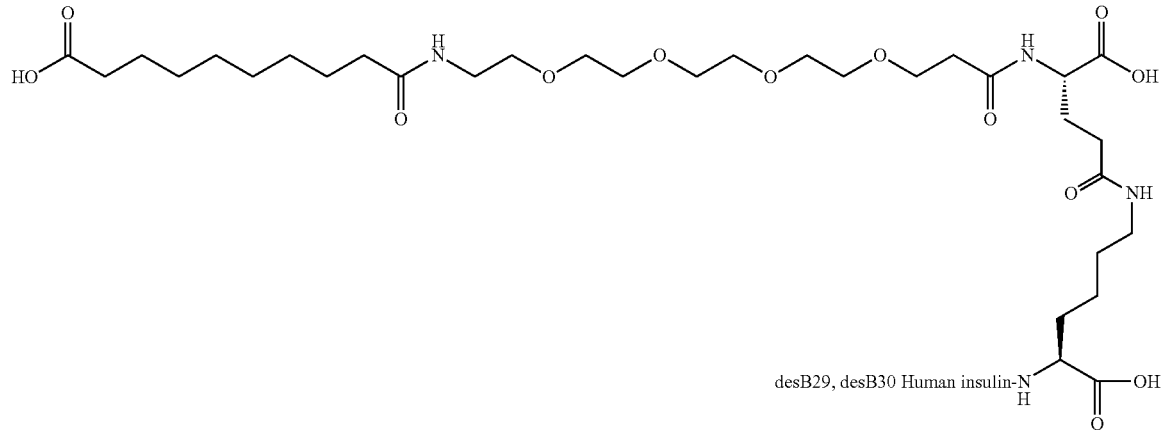

Example 26

N^{εB29}-{3-[2-(2-{2-[2-(11-carboxyundecanoylamino)ethoxy]ethoxy}ethoxy)ethoxy]propionyl-γ-glutamyl} desB30 human insulin

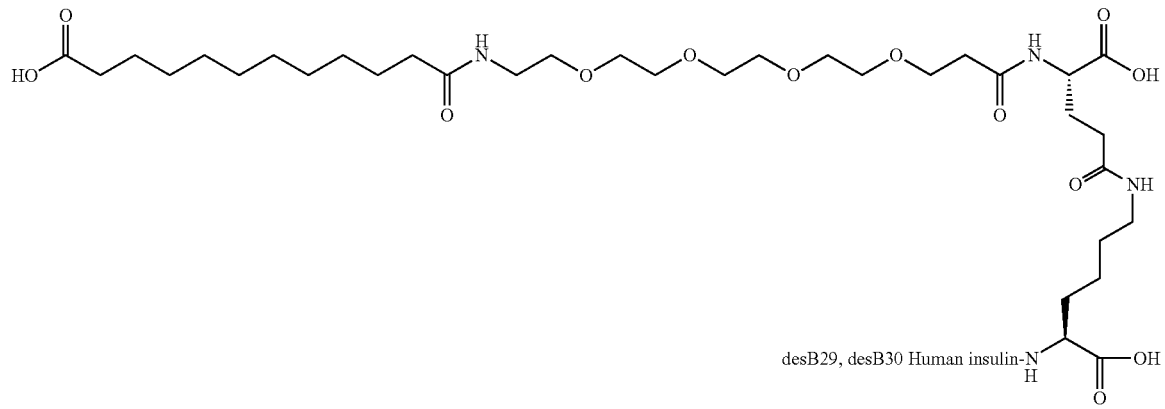

Example 27

N^{εB29}-{3-[2-(2-{2-[2-(13-carboxytridecanoylamino)ethoxy]ethoxy}ethoxy)ethoxy]propionyl-γ-glutamyl} desB30 human insulin

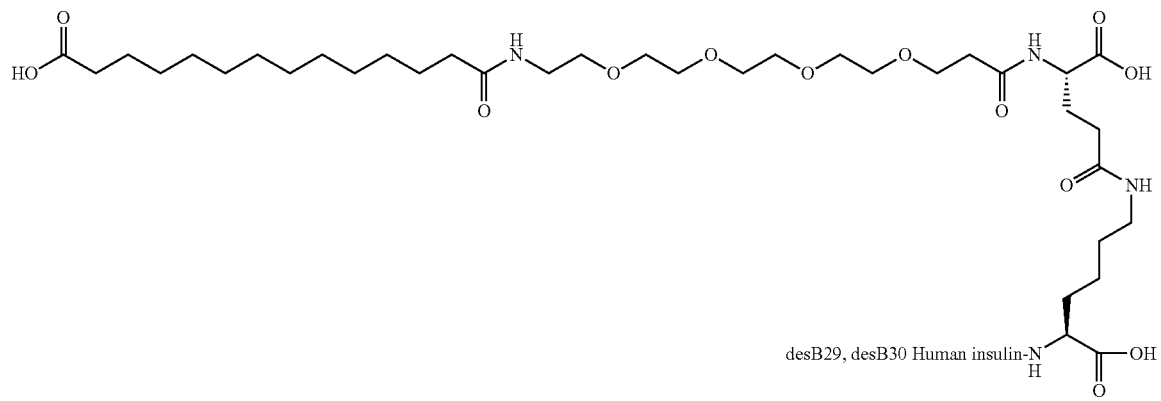

Example 28

Insulin Receptor Binding of the Insulin Derivatives of the Invention

The affinity of the insulin analogues of the invention for the human insulin receptor was determined by a SPA assay (Scintillation Proximity Assay) microtiterplate antibody capture assay. SPA-PVT antibody-binding beads, anti-mouse reagent (Amersham Biosciences, Cat No. PRNQ0017) were mixed with 25 ml of binding buffer (100 mM HEPES pH 7.8; 100 mM sodium chloride, 10 mM MgSO$_4$, 0.025% Tween-20). Reagent mix for a single Packard Optiplate (Packard No. 6005190) is composed of 2.4 μl of a 1:5000 diluted purified recombinant human insulin receptor—exon 11, an amount of a stock solution of A14 Tyr[$^{125}$I]-human insulin corresponding to 5000 cpm per 100 μl of reagent mix, 12 μl of a 1:1000 dilution of F12 antibody, 3 ml of SPA-beads and binding buffer to a total of 12 ml. A total of 100 μl was then added and a dilution series is made from appropriate samples. To the dilution series was then added 100 μl of reagent mix and the samples were incubated for 16 hours while gently shaken. The phases were the then separated by centrifugation for 1 min and the plates counted in a Topcounter. The binding data were fitted using the nonlinear regression algorithm in the GraphPad Prism 2.01 (GraphPad Software, San Diego, Calif.).

Human Serum Albumin Affinity Assay

Relative binding constant of 125I-TyrA14-analogue to human serum albumin immobilised on Minileak particles and measured at 23° C. (detemir=1 in saline buffer)

| Compound | Insulin receptor affinity in relation to human insulin | Albumin affinity in relation to insulin Detemir |
|---|---|---|
| example 1 | 11 | 2.381 |
| example 2 | 12 | 10.649 |
| example 3 | 14 | 4.273 |
| example 4 | 9.2 | 1.201 |
| example 5 | 5.6 | 0.48 |
| example 6 | 8.3 | 3.59 |
| example 7 | 35 | |
| example 8 | 34 | |
| example 9 | 34 | |
| example 10 | 27 | |
| example 11 | 16 | |
| example 12 | 38 | |
| example 13 | 17 | |
| example 14 | 15 | |
| example 15 | 35 | |
| example 16 | 31 | |
| example 17 | 17 | |

Example 29

Pulmonary Delivery of Insulin Derivatives to Rats

The test substance will be dosed pulmonary by the drop instillation method. In brief, male Wistar rats (app. 250 g) are anaesthetized in app. 60 ml fentanyl/dehydrodenzperidol/dormicum given as a 6.6 ml/kg sc priming dose and followed by 3 maintenance doses of 3.3 ml/kg sc with an interval of 30 min. Ten minutes after the induction of anaesthesia, basal samples are obtained from the tail vein (t=−20 min) followed by a basal sample immediately prior to the dosing of test substance (t=0). At t=0, the test substance is dosed intra tracheally into one lung. A special cannula with rounded ending is mounted on a syringe containing the 200 ul air and test substance (1 ml/kg). Via the orifice, the cannula is introduced into the trachea and is forwarded into one of the main bronchi—just passing the bifurcature. During the insertion, the neck is palpated from the exterior to assure intratracheal positioning. The content of the syringe is injected followed by 2 sec pause. Thereafter, the cannula is slowly drawn back. The rats are kept anaesthetized during the test (blood samples for up to 4 hrs) and are euthanized after the experiment.

The invention claimed is:

1. An insulin derivative having a side chain attached either to the α-amino group of the N-terminal amino acid residue of B chain or to an ε-amino group of a Lys residue present in the B chain of the parent insulin molecule via an amide bond wherein said side chain comprises a monodisperse difunctional polyethylene glycol (PEG) group containing independently at each termini a group selected from (a) —NH2 and —COOH; (b) a fatty diacid moiety with from 4 to 22 carbon atoms; (c) 2, 3 or 4 free carboxylic acid groups; and (d) possible linkers which link the individual components in the side chain together via amide or ether bonds, said linkers optionally comprising a free carboxylic acid group.

2. The insulin derivative according to claim 1, wherein the monodisperse difunctional PEG group has from 2 to 20; from 2 to 10 or from 2 to 5 residues of ethyleneglycol.

3. The insulin derivative according to claim 1, wherein the fatty diacid comprises from 4 to 22 carbon atoms in the carbon chain.

4. The insulin derivative according to claim 3, wherein the fatty diacid comprises from 6 to 22, from 8 to 20, from 8 to 18, from 4 to 18, from 6 to 18, from 8 to 16, from 8 to 22, from 8 to 17 or from 8 to 15 carbon atoms in the carbon chain.

5. The insulin derivative according to claim 1, wherein the linker is an amino acid residue, a peptide chain of 2-4 amino acid residues or has the motif α-Asp, β-Asp, α-Glu, γ-Glu, α-hGlu, δ-hGlu, —N(CH$_2$COOH)CH$_2$CO—, —N(CH$_2$CH$_2$COOH)CH$_2$CH$_2$CO—, —N(CH$_2$COOH)CH$_2$CH$_2$CO— or —N(CH$_2$CH$_2$COOH)CH$_2$CO—.

6. The insulin derivative according to claim 1, wherein the Lys residue in the B chain of the parent insulin is in either position B3, B29 or is in one of positions B23-30.

7. The insulin derivative according to claim 1 having the formula

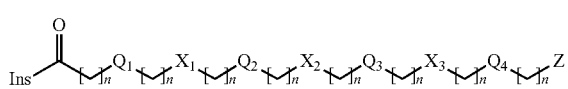

wherein Ins is the parent insulin moiety which via the α-amino group of the N-terminal amino acid residue of the B chain or an ε-amino group of a Lys residue present in the B chain of the insulin moiety is bound to the CO— group in the side chain via an amide bond;
each n is independently 0, 1, 2, 3, 4, 5 or 6;
$Q_1$, $Q_2$, $Q_3$, and $Q_4$ independently of each other can be selected from: (CH$_2$CH$_2$O)$_s$—; where s is 1-20;
—(CH$_2$)$_r$— where r is an integer from 4 to 22; or a divalent hydrocarbon chain comprising 1, 2 or 3 —CH=CH— groups and a number of —CH$_2$— groups sufficient to give a total number of carbon atoms in the chain in the range of 4 to 22;
—(CH$_2$)$_t$— or —(CH$_2$OCH$_2$)$_t$—, where t is an integer from 1 to 6;
—(CR$_1$R$_2$)$_q$—, where R$_1$ and R$_2$ independently of each other can be H, —COOH, and R$_1$ and R$_2$ can be different at each carbon, and q is 1-6;
—((CR$_3$R$_4$)$_{q1}$)$_1$—(NHCO—(CR$_3$R$_4$)$_{q1}$—NHCO)$_{1-2}$—((CR$_3$R$_4$)$_{q1}$)$_1$ or —((CR$_3$R$_4$)$_{q1}$)$_1$—(CONH—(CR$_3$R$_4$)$_{q1}$—CONH)$_{1-2}$—((CR$_3$R$_4$)$_{q1}$—)—, where R$_3$ and R$_4$ independently of each other can be H, —COOH, and R$_3$ and R$_4$ can be different at each carbon, and q$_1$ is 1-6-; and a bond;
with the proviso that $Q_1$-$Q_4$ are different;
$X_1$, $X_2$ and $X_3$ are independently selected from: O; a bond;

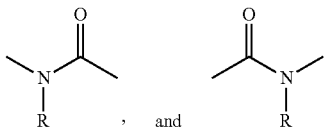

where R is hydrogen or —(CH$_2$)$_p$—COOH, —(CH$_2$)$_p$—SO$_3$H, —(CH$_2$)$_p$—PO$_3$H$_2$, —(CH$_2$)$_p$—O—SO$_3$H; —(CH$_2$)$_p$—O—PO$_3$H$_2$; or —(CH$_2$)$_p$-tetrazolyl, where each p independently of the other p's is an integer in the range of 1 to 6; and
Z is selected from: —COOH; —CO-Asp; —CO-Glu; —CO-Gly; —CO-Sar; —CH(COOH)$_2$; —N(CH$_2$COOH)$_2$; —SO$_3$H; —OSO$_3$H; —OPO3H$_2$, —PO$_3$H$_2$ and -tetrazolyl,
wherein the side chain comprises
a monodisperse difunctional PEG group containing independently at each termini a group selected from —NH$_2$ and —COOH;
a fatty diacid moiety with from 4 to 22 carbon atoms, 2, 3 or 4 free carboxylic acid groups; and
linkers which link the individual components in the side chain together via amide or ether bonds, said linkers comprising a free carboxylic acid group.

8. The insulin derivative according to claim 7, wherein s is in the range from 8 to 20, from 8-18, from 4-18, from 6-18, from 8 to 16, from 8 to 22, from 8 to 17 or from 8 to 15.

9. The insulin derivative according to claim 7, wherein s is from 1-20, from 1-10 or from 1-5.

10. The insulin derivative according to claim 7, wherein Z is —COOH.

11. The insulin derivative according to claim 1, wherein the parent insulin is a desB30 human insulin analogue.

12. The insulin derivative according to claim 1, wherein the parent insulin is selected from the group consisting of human insulin; desB1 human insulin; desB30 human insulin; GlyA21 human insulin; GlyA21 desB30 human insulin; AspB28 human insulin; porcine insulin; LysB28 ProB29 human insulin; GlyA21 ArgB31 ArgB32 human insulin; and LysB3 GluB29 human insulin or AspB28 desB30 human insulin.

13. The insulin derivative according to claim 1 selected from the group consisting of $N^{\epsilon B29}$-(3-[2-{2-(2-[ω-carboxy-pentadecanoyl-γ-glutamyl-(2-amino-ethoxy)]-ethoxy)-ethoxy}-ethoxy]-propinoyl) desB30 human insulin, $N^{\epsilon B29}$-(3-[2-{2-(2-[ω-carboxy-heptadecanoyl-γ-glutamyl-(2-amino-ethoxy)]-ethoxy)-ethoxy}-ethoxy]-propinoyl) desB30 human insulin, $N^{\epsilon B29}$-{3-[2-(2-{2-[2-(ω-carboxy-pentadecanoylamino)-ethoxy]-ethoxy}-ethoxy)-ethoxy]-propionyl-γ-glutamyl desB30 human insulin, $N^{\epsilon B29}$-(ω-[2-(2-{2-[2-(2-carboxy-ethoxy)-ethoxy]-ethoxy}-ethoxy)-ethylcarbamoyl]-heptadecanoyl-α-glutamyl) desB30 human insulin, $N^{\epsilon B29}$-(ω-[2-(2-{2-[2-(2-carboxy-ethoxy)-ethoxy]-ethoxy}-ethoxy)-ethylcarbamoyl]-heptadecanoyl-γ-glutamyl) desB30 human insulin, $N^{\epsilon B29}$-3-[2-(2-{2-[2-(ω-carboxy-heptadecanoylamino)-ethoxy]-ethoxy}-ethoxy)-ethoxy]-propionyl-γ-glutamyl desB30 human insulin, $N^{\epsilon B29}$-(3-(3-{2-[2-(3-[7-carboxyheptanoylamino]propoxy)ethoxy]-ethoxy}propylcarbamoyl)propionyl) desB30 human insulin, $N^{\epsilon B29}$-(3-(3-{4-[3-(7-Carboxyheptanoylamino)propoxy]butoxy}propylcarbamoyl)-propionyl-γ-glutamyl) desB30 human insulin, $N^{\epsilon B29}$-(3-(3-{2-[2-(3-[9-Carboxynonanoylamino]propoxy)ethoxy]ethoxy}-propylcarbamoyl)propionyl) desB30 human insulin, $N^{\epsilon B29}$-(3-(2-{2-[2-(9-carboxynonanoylamino)ethoxy]ethoxy}ethylcarbamoyl)propionyl-γ-glutamyl) desB30 human insulin, $N^{\epsilon B29}$-(3-(3-{4-[3-(9-Carboxynonanoylamino)propoxy]butoxy}-propylcarbamoyl)propionyl-γ-glutamyl) desB30 human insulin, $N^{\epsilon B29}$-(2-[3-(2-(2-{2-(7-carboxyheptanoylamino)ethoxy}ethoxy)-ethylcarbamoyl]propionyl-γ-glutamyl) desB30 human insulin, $N^{\epsilon B29}$-(3-[2-(2-{2-[2-(ω-carboxypentadecanoylamino)ethoxy]ethoxy}ethoxy)-ethoxy]propionyl)) desB30 human insulin, $N^{\epsilon B29}$-(3-(2-{2-[2-(2-{2-[2-(2-{2-[2-(2-{2-[2-(ω-carboxy-tridecanoylamino)-ethoxy]-ethoxy}-ethoxy)-ethoxy]-ethoxy}-ethoxy)-ethoxy]-ethoxy}-ethoxy)-ethoxy]-ethoxy}-ethoxy)-propionoyl-γ-glutamyl) desB30 human insulin, $N^{\epsilon B29}$-(3-[2-(2-{2-[2-(ω-Carboxy-tridecanoylamino)-ethoxy]-ethoxy}-ethoxy)-ethoxy]-propionyl-γ-glutamyl) desB30 human insulin, $N^{\epsilon B29}$-(3-[2-(2-{2-[2-(2-{2-[2-(ω-carboxy-tridecanoylamino)-ethoxy]-ethoxy}-ethoxy)-ethoxy]-ethoxy}-ethoxy)-ethoxy]-ethoxy}-propionyl-γ-glutamyl) desB30 human insulin, $N^{\epsilon B29}$-(3-(2-{2-[2-(ω-Carboxy-pentadecanoylamino)-ethoxy]-ethoxy}-ethylcarbamoyl)-propionyl-γ-glutamyl) desB30 human insulin, $N^{\epsilon B29}$-(3-(3-{2-[2-(3-[ω-Carboxypentadecanoylamino]propoxy)ethoxy]-ethoxy}propylcarbamoyl)propionyl-γ-glutamyl) desB30 human insulin, $N^{\epsilon B29}$-(3-(3-{4-[3-(ω-Carboxyundecanoylamino)propoxy]butoxypropylcarbamoyl)propionyl-γ-glutamyl) desB30 human insulin, $N^{\epsilon B29}$-(3-(3-{4-[3-(ω-carboxytridecanoylamino)propoxy]butoxypropyl-carbamoyl)propionyl-γ-glutamyl) desB30 human insulin, $N^{\epsilon B29}$-(3-(2-{2-[2-(ω-Carboxyundecanoylamino)ethoxy]ethoxy}ethylcarbamoyl)propionyl-γ-glutamyl) desB30 human insulin, $N^{\epsilon B29}$-(3-(2-{2-[2-(ω-carboxytridecanoylamino)ethoxy]ethoxy}-ethylcarbamoyl)propionyl-γ-glutamyl) desB30 human insulin, $N^{\epsilon B29}$-{3-[2-(2-{2-[2-(ω-carboxy-pentadecanoylamino)ethoxy]ethoxy}ethoxy)ethoxy]propionyl-gamma-γ-D-glutamyl) desB30 human insulin, $N^{\epsilon B29}$-{3-[2-(2-{2-[2-(7-carboxyheptanoylamino)ethoxy]-ethoxy}ethoxy)ethoxy]propionyl-γ-glutamyl} desB30 human insulin, $N^{\epsilon B29}$-{3-[2-(2-{2-[2-(9-carboxynonanoylamino)ethoxy]ethoxy}ethoxy)ethoxy]propioniyl-γ-glutamyl} desB30 human insulin, $N^{\epsilon B29}$-{3-[2-(2-{2-[2-(ω-carboxyundecanoylamino)ethoxy]ethoxy}ethoxy)-ethoxy]propionyl-γ-glutamyl} desB30 human insulin, $N^{\epsilon B29}$-{3-[2-(2-{2-[2-(ω-carboxytridecanoylamino)ethoxy]ethoxy}ethoxy)ethoxy]propionyl-γ-glutamyl} desB30 human insulin.

14. A method of treating diabetes in a patient in need of such a treatment, comprising administering to the patient a therapeutically effective amount of an insulin derivative according to claim 1 together with a pharmaceutically acceptable carrier.

15. A method of treating diabetes in a patient in need of such a treatment, comprising administering to the patient a therapeutically effective amount of an insulin derivative according to claim 1 in mixture with an insulin or an insulin analogue which has a rapid onset of action, together with a pharmaceutically acceptable carrier.

* * * * *

UNITED STATES PATENT AND TRADEMARK OFFICE
CERTIFICATE OF CORRECTION

PATENT NO. : 8,859,493 B2  Page 1 of 1
APPLICATION NO. : 13/506292
DATED : October 14, 2014
INVENTOR(S) : Patrick W. Garibay et al.

It is certified that error appears in the above-identified patent and that said Letters Patent is hereby corrected as shown below:

In the Claims:

At column 97, claim number 1, line number 52, replace "–NH2" with -- –NH$_2$ --.

Signed and Sealed this
Seventeenth Day of February, 2015

Michelle K. Lee
*Deputy Director of the United States Patent and Trademark Office*